United States Patent [19]

Markley et al.

[11] Patent Number: 4,824,475

[45] Date of Patent: Apr. 25, 1989

[54] ENHANCED HERBICIDAL TRIAZINE COMPOSITIONS AND METHOD OF USE

[75] Inventors: Lowell D. Markley, Midland, Mich.; Paul S. Zorner, Clayton, Calif.

[73] Assignee: The Dow Chemical Company, Midland, Mich.

[21] Appl. No.: 776,732

[22] Filed: Sep. 16, 1985

[51] Int. Cl.$^4$ .............................................. A01N 43/70
[52] U.S. Cl. .......................................... 71/93; 71/103; 71/DIG. 1
[58] Field of Search ...................... 71/93, 103, DIG. 1

[56] References Cited

U.S. PATENT DOCUMENTS

| | | | |
|---|---|---|---|
| 3,022,150 | 2/1962 | Weed | 71/93 |
| 3,152,882 | 10/1964 | Luckenbaugh | 71/115 |
| 3,551,131 | 12/1970 | Musselman et al. | 71/DIG. 1 |
| 3,900,509 | 8/1975 | Markley | 71/103 |
| 3,954,440 | 4/1976 | Markley | 71/103 |
| 3,997,322 | 12/1976 | Ratledge | 71/DIG. 1 |
| 4,018,801 | 4/1977 | Ozretich | 260/348 R |
| 4,211,549 | 7/1980 | Markley et al. | 549/563 |
| 4,447,257 | 5/1984 | Gernick, III | 71/DIG. 1 |

FOREIGN PATENT DOCUMENTS 0944570 12/1963 United Kingdom .................. 71/113

OTHER PUBLICATIONS

Markley III, "Herbicidal benzenemethanol, etc.", (1975) CA 85:108410c (1976).
Thompson et al., "Foliar and Root Absorption, etc.", Weed Science, 17, pp. 349-351 (1969).
Sieczka et al., "Herbicide Evaluation, etc." (1981), CA 94:133990k (1981).
Smit et al., "Herbicidal Triazine, etc." (1983), CA 99:171335m.

Primary Examiner—Richard L. Raymond
Assistant Examiner—A. A. Owens
Attorney, Agent, or Firm—S. Preston Jones; Ronald G. Brookens

[57] ABSTRACT

The herbicidal action of a herbicidal triazine upon weeds is enchanced upon also applying to the weeds a second herbicidal component, a butyl or pentyl glycol sulfonate or glycol sulfamate having 3, 5 or 3 substituted phenyl in the 2-position of the butyl or pentyl chain. The glycol sulfonate or sulfamate also adds its own herbicidal action to increase effectiveness.

Both components are applied simultaneously as a novel composition which may also contain crop oil or crop oil concentrate. Application is made post-emergently before weeds reach about the 8 leaf stage. Advantageously, in an additional step, triazine alone or in combination with at least some of the sulfonate or sulfamate is also applied at planting or very early postemergently prior to the treatment described.

47 Claims, No Drawings

ENHANCED HERBICIDAL TRIAZINE COMPOSITIONS AND METHOD OF USE

BACKGROUND OF THE INVENTION

The well-known herbicidal triazines have good activity against broadleaf weeds but at lower rates are frequently not sufficiently active in the control of certain grassy weeds and at higher rates are frequently residual in the soil. On the other hand, certain alkyl or aryl sulfonates or sulfamates of 2-phenyl butyl glycol described herein or in U.S. Pat. Nos. 3,900,509 and 3,954,440 are active against troublesome grassy weeds and are well tolerated by corn and sorghum and in some instances by soybeans and cottom but do not control broadleaf weeds as well as would be desired.

FIELD OF THE INVENTION

The invention relates to herbicidal compositions containing one or more herbicidal triazines in which the herbicidal activity of the triazine component is enhanced. The invention also relates to methods of using the herbicidal compositions of enhanced activity as well as to methods of applying one or more herbicidal triazines and a material capable of enhancing the activity of triazines.

DESCRIPTION OF THE PRIOR ART

Many of the butanediol sulfonates or sulfamates or pentanediol sulfonates or sulfamates employed herein and their use as herbicides are described in general in U.S. Pat. Nos. 3,900,509 and 3,954,440.

The numerous herbicidal symmetric triazines, such as atrazine and cyanazine and the asymmetric triazines, such as metribuzin, are well known and their use and properties as selective herbicides are described in numerous publications, e.g., *Herbicide Handbook of the Weed Science Society of America*, 4th Edition, 1979 and in the article by L. Thompson, Jr. and F. W. Slife, "Root and Foliar Absorption of Atrazine Applied Post-emergence of Broadleaf Weeds", Weed Science, 17 251–256 (1969). Representative methods of synthesis are described in U.S. Pat. Nos. 2,909,420; 3,590,040; 3,639,399; 3,671,523; 3,712,976; and 3,963,713. Other patents describing various triazines and their synthesis, formulation or use include 2,508,323; 2,510,564; 2,513,264; 3,658,893; 2,676,150; 2,682,541; 2,720,480; 2,891,855; 2,923,614; 3,451,802; 3,494,759; 3,503,971; 3,505,325; 3,517,003; 3,671,523; 3,961,936; 3,966,715 and 4,036,632.

The symmetric triazines are usually synthesized by trimerizing cyanogen chloride and replacing one or more of the three chlorines on the ring with, e.g., alkylamino, methoxy or alkylthio groups, by nucleophilic displacement with amines, alkoxides or thiols as described in U.S. Pat. No. 2,909,420.

The asymmetric triazine metribuzin can be made by reacting tertiary butyl pyruvic acid with the semi-carbazone of thiophosgene, viz.,

in aqueous reaction medium at reflux temperature whereupon cyclization takes place. Subsequently the sulfur attached to a ring carbon is alkylated by base catalyzed reaction with, e.g., methyl chloride. Methods of preparation of metribuzin and closely related compounds are further described in U.S. Pat. No. 3,671,523 as well as Belgian Pat. No. 697,083.

SUMMARY OF THE INVENTION

It has now been discovered that upon applying to the locus of weedy plants, preferably early post-emergence, but before they reach about the eight leaf stage, a combination of one or more herbicidal triazines and one or more of certain glycol sulfonates and/or sulfamates, hereinafter more fully described, ordinarily admixed with a carrier and optionally with a crop oil or crop oil concentrate, and in ranges of proportions and at application rates and under application conditions set forth hereinafter, there is obtained an unexpected enhancement of the herbicidal effect upon many weedy plants, particularly upon annulas, of any triazine present, while valuable grassy crops such as corn or sorghum, and in some instances soybeans and cotton, when similarly treated, e.g., when in the presence of the treated weeds, are undamaged or affected no more than would result from the use of the triazine(s) alone at the dosage employed according to the invention.

The new herbicidal compositions of the present invention comprise an agriculturally acceptable carrier and aherbicidally effective amount of a mixture containing in the range of, by weight, from about 1 to about 20 parts of a herbicidal triazine or mixture of such triazines, and about 1 to 2 parts of a second herbicidal component, the latter being one or a mixture of compounds each having the following formula:

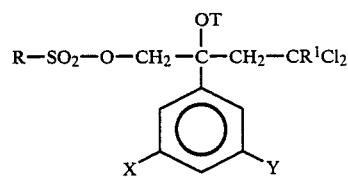

wherein:

R is $C_1$ to $C_{18}$ alkyl; $C_1$ to $C_4$ haloalkyl; $C_3$ to $C_6$ cycloalkyl; phenyl; naphthyl; benzyl; radical of monocyclic heterocyclic ring having ring atoms selected from the group consisting of carbon and at least one of nitrogen, sulfur and oxygen; radical of bicyclic heterocyclic fused ring structure having ring atoms selected from the group consisting of carbon and at least one of nitrogen, sulfur and oxygen; any of phenyl, naphthyl, benzyl, monocyclic heterocyclic radical or bicyclic heterocyclic fused ring radical in which up to three hydrogens on the ring have been replaced by substituent groups which may be the same or different and are selected from the group consisting of methyl, methoxy, methylthio, chloro, bromo, $CF_3$ or nitro; or $NR^2R^3$;

$R^1$ is $CH_3$, Cl, Br, F or

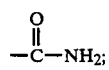

X and Y are the same or different and are Cl, Br, F, $CF_3$ or H, provided X and Y may not both be H; and $R^2$ is H or $C_1$ to $C_4$ alkyl; and $R^3$ is H; $C_1$ to $C_4$ alkyl; phenyl; naphthyl; benzyl; radical of monocyclic heterocyclic ring having ring atoms selected from the group consisting of carbon and at least one of nitrogen, sulfur and oxygen; radical of bicyclic heterocyclic fused ring structure having ring atoms selected from the group consisting of carbon and at least one of nitrogen, sulfur and oxygen; and any of phenyl, naphthyl, benzyl, monocyclic heterocyclic radical or bicyclic heterocyclic fused ring radical in which up to two hydrogens on the ring have been replaced by substituent groups which may be the same or different and are selected from the group consisting of methyl, methoxy, methylthio, chloro, bromo, CF$_3$ or nitro; but when R$^2$ is C$_1$ to C$_4$ alkyl R$^3$ must be H or C$_1$ to C$_4$ alkyl; and T is H,

The composition may be formulated initially, or made up in the tank mix employed, to contain, advantageously, up to 2 parts by weight of crop oil or crop oil concentrate per part of total active herbicidal components.

In all such uses the present compositions are advantageously employed in an amount sufficient to provide at least about 5/8 (i.e., 0.625) lb/acre and preferably at least 1.25 lb/acre in total of active components in the composition but less than an amount which is phytotoxic to any valuable crops growing in the plot under treatment, generally up to about 3 lb/acre.

The composition conveniently adapts itself to pre-emergent and postemergent applications to valuable field crops such as corn or sorghum, and in the selective control of a grood spectrum of both annual grassy weeds and annual broadleaf weeds in the presence of such crops. While the sulfonate or sulfamate compounds are not completely non-harmful to crops, such as corn or sorghum, glycol sulfonate or sulfamate compounds and triazines which are somewhat harmful to grassy crops and some braodleaf crops can frequently be employed in the present composition and the composition applied to control weeds in grassy crops or in cotton, pineapple or other plantation crops using methods of application which minimize exposure of the foliage of the crop to the composition spray droplets, such as directed spray methods.

Among compounds of this invention, while phenyl substituted butyl or pentyl glycol sulfonates and sulfamates disubstituted at ring positions 3 and 5 generally show good to excellent selectivity for crops such as corn and sorghum at operable dosages at which good weed control is obtained, phenyl substituted glycol sulfonates and sulfamates monosubstituted at right position 3 are generally somewhat less well tolerated when applied alone but appear to be better tolerated when in combination with a triazine herbicide. Also, s-triazines having an alkylthio, i.e., —S-alkyl, group on the ring are less well tolerated by such crops than those having a chloro group.

The glycol sulfonates and glycol sulfamates utilized according to the present invention have now been found to form an epoxy compound under some circumstances, such as within plant tissues, and in solution in some solvents or aqueous compositions, as illustrated by the following transformation:

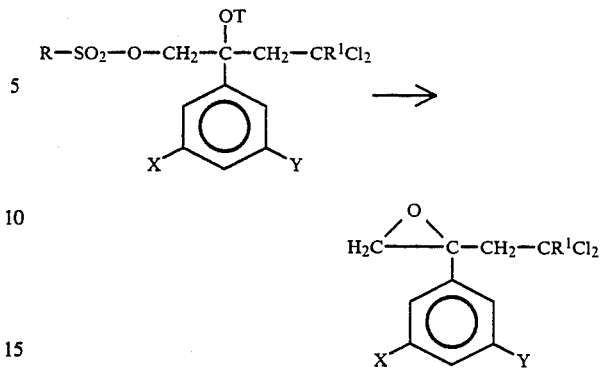

wherein R, R$^1$, X, Y and T are as defined above. The resulting oxirane compound falls within the group of compounds taught and claimed in U.S. Pat. Nos. 4,211,549 and 4,018,801 or are closely related thereto. Such compounds are taught in copending application Ser. No. 445,300, filed Nov. 29, 1982, to enhance the activity of the herbicidal triazines.

It has now been found that the present composition has the particular advantage that the glycol sulfonate or sulfamate component not only contributes its herbicidal characteristics to the composition but also increases the activity of the triazine component, resulting in greater than additive weed control. It is not desired to be bound by any particular theory, but the mode of action is believed to be, and physiological studies indicate, that the glycol sulfonate or sulfamate compounds utilized according to the invention, whether or not entirely converted to an oxirane compound, inhibit the activity of plant enzymes such as glutathione-S-transferase.

This enzyme is present at various levels in many triazine tolerant plants, particularly weedy grasses and valuable crops such as corn and sorghum and will detoxify triazine herbicides such as chloro-triazines and thioalkyl-triazines through enzyme dependent conjugation with the tripeptide glutathione. This enzyme dependent conjugation appears to be a primary factor responsible for plant tolerance to the triazine herbicides, e.g., corn tolerance to atrazine. By slowing or inhibiting for a time the above-described detoxificiation of a triazine or triazine blend with a glycol sulfonate or sulfamate compound, the triazine component is retained in a herbicidally effective form and amount within plant tissues for a longer period of time resulting in enhanced activity and increased effectiveness. The mode of action is not entirely understood but appears to differ from and produce a greater effect than would result simply from use of an equimolar amount of oxirane compound in the composition applied. Moreover, the glycol sulfonates and sulfamates are substantially less volatile than the oxiranes and a higher proportion of the present compounds enters the foliar structures of plants when applied thereto.

Crops tolerant to the glycol sulfonates or sulfamates and to triazines in admixture are believed to have capacity to detoxify the glycol sulfonate or sulfamate component and/or have sufficient triazine detoxification capability, e.g., glutathione-S-transferase activity, to overcome the inhibitory effect. A similar plant response to believed to take place in the slightly larger and more resistant grassy and broadleaf weeds which are controlled by the present composition when applied at an earlier stage.

Thus, the present composition is found to be more effective in weed control when applied up to about two to four weeks after seending the field crop, whereas the enhancement of the triazine activity diminishes considerably when the weeds reach the seven to eight leaf stage, generally four or more weeks after the crop is planted. Preferably application is made postemergently when weedy plants are between the two and four to six leaf stages, but applications can also be made effectively even earlier, such as, preemergently.

While it is generally more economical to make a single application of both active components in combination, consistent with the believed basis for the enhancement effect, greater enhancement is observed when the triazine has had greater opportunity to enter and accumulate in the plant tissues. This is often aided by increasing the time available for triazine uptake, particularly that which may be taken up from soil, by applications in which the triazine component is applied separately and prior to application of the glycol sulfonate or sulfamate component. Thus, the present invention also contemplates sequential treatments in which the triazine may be applied preemergently or very early postemergently, and the glycol sulfonate or sulfamate applied alone, but preferably admixed with at least a small amount of additional triazine, as an early postemergent application. If desired, some glycol sulfonate or glycol sulfamate may be admixed with the triazine in the initial application though no particular advantage appears to arise from such practice.

In sequential applications the triazines may be usefully applied preemergently or very early post-emergently up to about four weeks, depending on conditions such as temperature, soil moisture and soil type, before applying the glycol sulfonate or sulfamate component early postemergently, normally in combination with the same or different triazine.

In order to achieve the desired enhancement of the triazine component or blend used, it is essential to use sufficient glycol sulfonate or sulfamate. While the dosage required for optimum enhancement is affected by the particular choice of glycol sulfonate or sulfamate and triazine employed, and the tolerance of the particular plant species to be controlled, the compositions are normally advantageously employed in applications in which the glycol sulfonate or sulfamate compound is supplied at a dosage of at least 0.125 lb/acre and preferably about 0.25 to 0.5 lb/acre with the triazine component at dosage ratios stipulated hereinabove.

In conventional preemergent applications, e.g., to corn, the triazines are applied at a rate in the range of about 1 to 4 pounds (lbs) per acre, the exact rate being selected with a view to the two most important but separate factors, viz., soil moisture and soil type. If soil moisture is low, more triazine is required to achieve weed control and also the triazine requirement is increased if the soil contains a high level of organic matter.

In applying a triazine separately according to the invention, the tirazine is applied preemergently or very early postemergently at a rate appropriate for the safety of the crop to be planted and with a view to the factors above mentioned, the rate being in the range of about 0.5 to about 4 lbs per acre and preferably about 1 to 3 lbs per acre.

Then, after the crop germinates, the glycol sulfonate or sulfamate component utilized according to the present invention is applied early postemergently when the majority of the weeds present in the cropland are at the 2 to 6 leaf stage, preferably at the 2 to 4 leaf stage. The glycol sulfonate or sulfamate may be applied alone but is preferably applied in combination with additional triazine at a rate in the range of about 0.125 to 0.5 lb per acre, and preferably about 0.25 to 0.5 lb per acre of the glycol sulfonate or sulfamate plus from about 0.5 to about 1.5 lb per acre of the triazine. Where 2 lbs per acre triazine has been applied preemergently, satisfactory weed control is usually achieved by using about 0.5 to 1 lb per acre of traizine in combination with about 0.25 to 0.5 lb per acre of the glycol sulfonate or sulfamate in the sequential postemergent treatment.

If desired, the postemergent treatment may also be divided and applied as a split treatment about 7 to 14 days apart.

The composition comprising the present mixture of herbicides is sufficiently increased in effectiveness so as to permit the effective utilization of reduced amounts of each of the active components while achieving good broad spectrum weed control of both grassy weeds and broadleaf weeds with little or no damage to the tolerant crops, such as corn or sorghum, or damage from normally less selective triazines or glycol sulfonate or sulfamates may be avoided by employing application procedures, which minimize exposure of the crop plants. The crop yields obtained and the control achieved of weeds on the cropland are generally much superior to that obtained when either of the active constituents of the mixture is employed alone. Thus, the practice of the present invention provides for a desirable economic advantage for the agriculturist having both components available.

DETAILED DESCRIPTION OF THE INVENTION

The terms triazine component and glycol sulfonate or sulfamate component, respectively, refer to a single triazine or blend of two or more triazines, on the one hand, or a single glycol sulfonate or glycol sulfamate of the class described or a blend of two or more such compounds, on the other hand.

The herbicidal triazines employed in the composition and method of the present invention are selected both from the herbicidal asymmetric triazines and the so-called symmetrical triazines.

The suitable symmetrical triazines are selected from the herbicidal triazines of the formula:

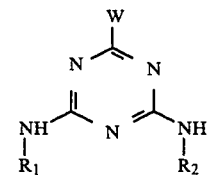

wherein
W is Cl, SCH$_3$ or SC$_2$H$_5$ and
R$_1$ and R$_2$ are each independently selected from methyl, ethyl, n-propyl, isopropyl, cyclopropyl, 2-cyano-2-methylethyl, sec-butyl, tert-butyl and propoxymethyl.

Suitable asymmetric triazines are described in U.S. Pat. Nos. 3,671,523; 3,961,936; 3,966,715 and 4,036,632.

Suitable asymmetric triazines are particularly to be selected from 4-amino-3-alkylthio-as-triazin-5(4H)-ones with substituents in the 6 position selected from alkyl, haloalkyl, halo, nitro or alkoxy as shown in the following formula

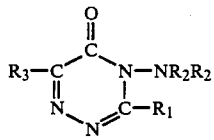

wherein:

$R_1$ is lower alkylmercapto of 1 to 4 carbons, each $R_2$ is independently hydrogen or loweralkyl of 1 to 3 carbons; and $R_3$ is lower alkyl of 1 to 4 carbons, haloalkyl of 1 to 4 carbons, halo, nitro or alkoxy of 1 to 4 carbons.

The compound metribuzin wherein $R_1$ is —SCH$_3$, both of $R_2$ are hydrogen and $R_3$ is tertiary butyl is most preferred among the asymmetric triazines.

Specific examples of herbicidal triazines suitable for use according to the present invention are: ametryn, atrazine, cyanazine, cyprazine, desmetryn, dipropetryn, prometryn, propazine, simazine, symetryne, terbutryn and metribuzin. Preferred triazines used in the composition and method of the invention are ametryn, atrazine, cyanazine, propazine, simazine, symetryne and metribuzin. The most preferred triazines are atrazine and cyanazine or a blend or co-mixture thereof.

The glycol sulfonate or sulfamate compounds, carrying a mono or disubstituted phenyl, used in the present compositions are nearly all white crystalline solids, freely soluble in most organic solvents, melting at about 90° to 115° C. with some melting as low as about 60° C. and others as high as about 150° C., while the triazines are white crystalline solids, usually fairly high melting and freely soluble in polar organic solvents such as acetone, methanol or dimethylformamide, but rather low to sparingly soluble in water or aliphatic hydrocarbons such as pentane.

The triazines, accordingly, are best formulated as a flowable concentrate, a wettable powder, or a water dispersible granule, whether formulated alone or in combination with the glycol sulfonate or sulfamate compounds. The glycol sulfonate or sulfamate compounds may be separately formulated, e.g., as an emulsifiable concentrate and the active ingredients separately dispersed in water and then combined in suitable proportions hereinafter described to form a tank mix, or the respective concentrates may be used to make up a single tank mix directly. Care must be taken, however, in the choice of the medium in which the glycol compound is taken up as a number of these compounds may convert to the corresponding oxirane compound while dissolved in a polar solvent. For example, 4,4,4-trichloro-2-(3,5-dichlorophenyl)-2-hydroxybutyl-(2,5-dichlorophenyl)-sulfonate and 4,4,4-trichloro-2-(3,5-dichlorophenyl)-2-hydroxybutyl-4-methylsulfonate each convert, within several hours, in major proportion, to the corresponding oxirane compound in polar organic solvent media and in aqueous media when emulsified with an aniionic surfactant such as dodecylbenzene sulfonate.

On the other hand, it is convenient to combine both active ingredients together in a concentrate in the form of a suspension-emulsion concentrate, a flowable suspension concentrate, a wettable powder, or a dispersible granule having the active ingredients in desired relative proportions. Such combination concentrate is dispersed in water to form a tank mix ready for field use.

While the triazines have been most generally applied preemergently for weed control in croplands, it is known to utilize crop oil in preparing spray mixes of the triazines for postemergent applications. The crop oils are phytobland, i.e., non-phytotoxic, oils which facilitate penetration by the triazines of the leaf structure of plants but are usually not harmful to field crops such as corn or sorghum when used at conventional rates. Generally, according to established practices, about 0.2 to 2.0 parts of crop oil have been employed per part of triazine used alone. Similar proportions of crop oil may be used in the tank mixes of the present composition, based on the total amount of active ingredients present.

The optional crop oil component of the tank mix composition of the present invention is a petroleum distillate containing primarily paraffinic and naphthenic hydrocarbons and generally containing less than 25 percent by weight aromatics. Such crop oils are known compounds which are disclosed in U.S. Pat. No. 3,997,322 which is incorporated herein by reference. Crop oils are non-phytotoxic and generally have the following range of properties:

| | |
|---|---|
| Gravity, °API/60° F. | 31.0–36.0 |
| Viscosity, SUS/100° F. | 60–120 |
| Viscosity, SUS/210° F. | 34–38 |
| Flash point, °F. | 300–400 |
| Fire point, °F. | 375–400 |
| Pour temperature, °F. | −10 to +20 |
| Unsulfonated residue, wt. percent (ASTM) | 75.5–99.9 |
| Refractive index, 25° C. | 1.4660–1.4690 |
| Gel Aromatics, wt. percent, max. | 25.0 |
| Distillation range at 10 mm. Hg (ASTM D-1160) °F. | 300–500 |

Other crop oils are mainly aliphatic petroleum liquids having an average of from about seven to about nine carbon atoms per molecule, and a boiling temperature in the range of about 95° to 150° C. Crop oils of vegetable or animal origin are also sometimes used.

The term "crop oil" when used herein is meant to encompass crop oil concentrates. A crop oil concentrate is a crop oil which contains a greater proportion of surfactants or emulsifiers that a "crop oil". A crop oil concentrate typically contains surfactants or emulsifiers in amounts of up to about 30 percent by weight while a crop oil generally contains less than 5 percent by weight of surfactants or emulsifiers.

Crop oils are well known tank mix additives and are commercially available. Examples of suitable crop oils employed in the practice of the present invention, including crop oils, crop oil concentrates and blends of crop oils with an emulsifying agent are: Sun ® 11-E; Atpulse ® 411-F; Booster ® Plus E; Agri-Oil ® Plus; Agri Dex ®; Agrodex;200 ; Herb-Oil ® Plus; U.S.S. Spray Adjuvant ®; Agicide Activator ®; Prime Oil ®; Crop Surf ® Spray Oil; Adjucide ®; Mor-Act ®; Sunoco ® Superior Spray Oils; Orchex ® 696; Paramid ® 100; Sun ® Superior Spray Oils; and a vegetable oil, such as Bio-Veg. (The symbol ® is used to signify registered trademarks.)

The present herbicidal compositions in concentrate form are necessarily in the form of one of an emulsion, a suspension, a dispersible granule or a wettable powder, according to intended use. All application forms must contain the active components in fine distribution, i.e., either in an emulsion or finely suspended in a liquid carrier or finely distributed in a wettable powder form carrier or a water dispersible granule.

If it should be desired to employ the present mixed active components for total destruction of vegetative growth, as in fallow land, the herbicidal effect of the components can be increased by the use of carriers which are per se phytotoxic, e.g., high boiling mineral oils or chlorohydrocarbons. Mineral oil fractions such as kerosene or diesel oil or coal tar oil may be used as solvent for solutions which can be sprayed onto plants for eradication of plant growth. The active components are added to such oils or liquids directly or after first dissolving in a suitable auxiliary solvent such as xylene.

For the preferred uses described herein, the active ingredients may be dissolved in, preferably, a paraffinic high boiling solvent such as Isopar M solvent or in an isoparaffinic phytobland crop oil, or, in a glycol ether such as propylene glycol monomethyl ether, diethylene glycol n-butyl ether or dipropylene glycol monomethyl ether, and combined with one or more suitable emulsifiers for the production of emulsion concentrates which can be diluted with water to form a tank mix in the form of an aqueous emulsion.

The active ingredients are not freely soluble in the paraffinic solvents and it may be found preferable, in order to conserve solvent volume where a paraffinic solvent is employed, to disperse the active ingredient in finely-divided and suspensed form in the paraffinic solvent forming a flowable suspension rather than an emulsion concentrate, or, to increase solvency of the paraffinic solvent by the addition thereto of a chlorinated hydrocarbon such as tetrachloroethane, ethylene chloride or monochlorobenzene, or of any of xylene or xylene fraction petroleum distillate, tetrahydronaphthalene or alkylated naphthalene, or an alcohol, such as a $C_6$ to $C_8$ alcohol exemplified by butanol or isooctanol or a cyclic ketone such as cyclohexanone, or, dimethylformamide or dimethylsulfoxide may be used, or a mixture of any of these additional solvents. Any of the additional solvents may be used as the sole or primary solvent in most cases but the use of one or more of the paraffinic solvents or glycol ethers as the sole or primary solvent is preferred.

Examples of cation active emulsifiers or dispersing agents are quaternary ammonium compounds. Examples of anion active emulsifying agents are soap, soft soap, long chain aliphatic sulfuric acid monoesters, araliphatic sulfonic acids, and long chain alkoxyacetic acids, including, ethoxylated monohydric sulfated alcohol salts of sodium, potassium, alkaline earth metals, ammonium, alkyl amines, alkanolamines or blends thereof (also designated in the art as alkyl polyether alcohol sulfates); ethoxylated sulfated alkylphenol salts of sodium, potassium, alkaline earth metals, ammonium, alkyl amines, or alkanolamines or blends thereof (also designated in the art as alkylaryl polyether alcohol sulfates); and the sodium, potassium, alkaline earth metal, or ammonium salts of alkyl phenoxybenzene disulfonates.

Examples of nonionic emulsifiers are polyglycol ethers of fatty alcohols and polyethylene oxide or polypropylene oxide condensation products and include ethoxylated alkyl phenols (also designated in the art as alkylaryl polyether alcohols); ethoxylated aliphatic alcohols (or alkyl polyether alcohols); ethoxylated fatty acids (or polyoxyethylene fatty acid esters); ethoxylated anhydrosorbitol esters (or polyethylene sorbitan fatty acid esters); ethoxylated polyoxypropylene glycols (polyalkylene oxide block copolymers); ethoxylated polyoxypropylene monohydric alcohols (polyalkylene oxide blocks copolymers of monohydric alcohols); and ethoxylated polyoxypropylene alkyl phenols (polyalkylene oxide block copolymers of alkyl phenols).

Many specific suitable emulsifiers of the types referred to herein are listed in McCutcheon, "Detergents and Emulsifiers 1970 Annual" (1970) Allured Publishing Company, Ridgewood, N.J., especially at pp. 38, 78, 177, 232 and 243.

Emulsion concentrates are most usually made up by taking up the triazine and the epoxy butane compound in an emulsifier with or without dispersing agent added, and if necessary, solvent. The emulsifier and/or dispersing agent are selected as understood in the art to provide a homogeneous concentrate which is capable of being dispersed in water to form, preferably, a stable emulsion in water for use in the field as a tank mix so as to avoid the need for frequent mixing of the tank mix. See the discussion hereinafter regarding hydrophobic-hydrophilic balance values in selecting emulsifiers and blends thereof.

The present herbicidal mixture may also be made up into an emulsifiable concentrate following the procedures and utilizing the emulsifiers and surfactants and solvent aids described in U.S. Pat. No. 3,986,862. The patent describes the preparation of emulsifiable concentrates of metribuzin and alachlor by first taking up the active components and an appropriate emulsifying agent in a small amount of chlorobenzene.

However, since the triazines have such a limited solubility in water, and the solvents which must be used to make up an emulsion concentrate are relatively expensive and the concentrates achievable nonetheless do not contain more than about 10 to 30 percent active ingredient, it is much preferred for other than small scale uses to prepare the present concentrate compositions (1) as a suspension emulsion in which the triazine or triazine blend is suspended in an emulsion of the glycol sulfonate or sulfamate compound or compounds, (2) as a wettable powder, (3) as a water dispersible granule product or (4) as an oil-based suspension concentrate whereby both active components are suspended in an oil, i.e., organic and typically paraffinic solvent.

Suspension-emulsion type concentrates are made up by grinding the solid triazine component together with one or more suitable emulsifiers and/or dispersing agent, a clay gellant, and a little solvent in which the triazine is insoluble or very-sparingly soluble. The glycol sulfonate or sulfamate compound or compounds may be added before commencing the grinding operation but is preferably added as grinding is being concluded. The emulsifiers and/or dispersing agents are selected with a hydrophobic-hydrophilic balance value in the range of about 10 to about 17 and preferably between about 13 to about 15, as well understood in the art, to provide a stable uniform suspension-emulsion concentrate holding the insoluble triazine component in suspension and the glycol sulfonate or sulfamate component emulsified. The concentrate must be capable of holding the triazine in suspension and the glycol sulfonate or sulfamate in emulsified form upon dilution to a tank mix for use in the field.

Additional teaching regarding flowable concentrates, in general, is found in the chapter "Properties of Suspension Concentrates" by H. Schaller and H. Niessen in the text Pesticide Chemistry, Vol. V, Gordon and Breach, Science Publishes, New York, N.Y. 1972, pp. 441-452. See also U.S. Pat. No. 3,948,636 for the description of relatively stable suspension concentrates of triazines and method of preparation.

The suspension emulsion of the invention preferably contains ingredients and proportions as follows:

| Ingredient | Weight % |
| --- | --- |
| glycol sulfonate or glycol sulfamate | 12-16 |
| triazine(s) | 32-36 |
| sulfonated naphthalene formaldehyde condensate, such as Daxad 11 or Morwet D425 or lignosulfonate salt, such as Polyfon H or Marosperse CBO-3 | 0.5-4 |
| clay gellant, such as Bentone 34 or Attagel 50 | 0.2-0.8 |
| alkaryl alkoxylate nonionic emulsifier, such as, Triton X-100, T-Det N15 or Polyglycol 26-3; alkyl ethoxylate such as Emulsogen M or sorbitan oleate such as Tween 85 | 2-6 |
| calcium salt or blended amine salts of alkaryl sulfonate anionic emulsifier, such as, Witconate P1220 or Sponto AC31-2 | 2-4 |
| solvent: xylene range petroleum distillate, such as, Tenneco 500-100 or Aromatic 100 and/or a paraffinic oil | balance |

Such composition is preferably made up by wet milling the triazine component alone or with most of the additaments and subsequently blending in the glycol sulfonate or sulfamate component in admixture with an emulsifier and at least part of the solvent. The suspension emulsion may also be prepared by wet grinding the entire composition.

The oil-based flowable compositions, used as concentrates, are made up in a similar manner to the suspension emulsions except that both active ingredients, or both types if more than one triazine or sulfonate or sulfamate is included in the composition, are suspended. Suspension is achieved by milling the active ingredients alone or together and with the additaments such as surfactants, though the latter are sometimes simply blended into the milled mixture, all being ground and/or blended and suspended exclusively is an oil-based solvent suitable for dispersion into a tank mix for spray applications as well as understood in the art. An example of a suitable oil-based vehicle is sold under the brand name Isopar M.

Wettable powders are prepared by mixing and blended with or without grinding, as may be indicated, the triazine component in finely-ground form with a suitable solid such as finely-ground talcum, diatomaceous earth, kaolin, bentonite, calcium carbonate, boric acid, tricalcium phosphate, sawdust, powdered cork, charcoal or other dried ground material of vegetable origin. Sometimes it is desirable to first take up the triazine(s) and the glycol sulfonate or sulfamate compound(s) in a volatile solvent therefor to assist in the uniform and thorough dispersion throughout the solid carrier. The solvent may be removed and then resulting powder used as a dust. In any event, the triazine(s) should be reduced to an average particle size of less than 20 microns, preferably less than 10 microns and even more preferably in the range of 1 to 5 microns.

More preferably, an emulsifier and/or dispersant is added to the mixture of active components and solid carrier during the mixing or grinding steps to provide a wettable powder capable of dispersion in water to provide a sprayable composition for field use. To provide for improved properties of the present compositions in water-dispersed tank mix form obtained on dilution of a concentrate with water it may be desirable to incorporate in the concentrate a protective colloid such as a clay gellant, typically a gum. An example of a suitable gum is a xanthan gum having an average molecular weight of at least 200,000. See also the teachings of U.S. Pat. No. 3,796,562 illustrating the making of a wettable powder from a triazine and a liquid herbicide.

The wettable powders of the invention preferably contain, by weight, about 70 to 80 percent of the combined active ingredients, with the triazine(s) in finely-divided form but generally reduced to the fineness described hereinabove by hammer milling or air milling the entire composition or a part thereof before final blending.

In addition, the composition contains from a total of 2 to about 10 percent of anionic and nonionic surface-active agents or emulsifiers which may also be selected from dispersants. A more preferred range is 2 to about 6 percent in the aggregate and most preferred is about 4 to 6 percent.

Additional aids such as antifoaming agents may be included in minor amounts, if desired, and the balance of approximately 10 to about 25 percent of a solid carrier, preferably synthetic precipitated hydrated silica, or, a ball clay, a kaolin clay, a diatomite or a silicate material.

In general, a water dispersible granular product is made by granulating or agglomerating most any wettable powder formulation that is basically suitable for the active ingredients. Agglomeration is carried out in a conventional manner, e.g., conveniently by use of a pan agglomerator. Illustrative water dispersible granular products are described in U.S. Pat. No. 3,954,439 which formulations are readily adapted to the present combination of herbicidal active ingredients. British Pat. No. 1,583,499 also describes suitable components and techniques for accomplishing agglomeration in the production of a water dispersible granule product.

The various forms of application can be adapted to the intended use in the usual way by the addition of substances which improve the distribution, the adhesive properties to foliar structure, or resistance to rain or resorption. Such substances include fatty acids, resins, wetting agents, glue, casein and algivates. The biological activity can also be modified or broadened by the addition of bactericides, fungicides, compatible complementary plant growth modifiers, as well as fertilizers, or insecticides if desired. The compositions may also be modified, if desired, by the addition of 0.1 to 5 percent by weight of an anti-foaming agent and/or a freezing point depressant. Also a minor amount of a bactericide may be added for the protection of the composition per se.

The alkyl and arylglycol sulfonates and sulfamates utilized according to the invention may be made in any of several ways as described in U.S. Pat. Nos. 3,900,509 and 3,954,440, utilizing an appropriate alpha-methylstyrene derivative prepared as described in U.S. Pat. No. 3,373,011.

An appropriate alpha-methylstyrene derivative is one of the following formula:

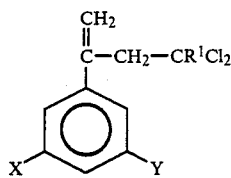

in which:

R¹ is as indicated hereinabove, CH₃, Cl, Br, F or

and X and Y are each independently H, Cl, Br, F, CF₃ or NO₂ but when X is H, Y must be other than H; and R² is H or C₁ to C₄ alkyl; and R³ is H, C₁ to C₄ alkyl; benzyl; naphthyl; benzyl; radical of monocyclic heterocyclic ring having ring atoms selected from the group consisting of carbon and at least one of nitrogen, sulfur and oxygen; radical of bicyclic heterocyclic fused ring structure having ring atoms selected from the group consisting of carbon and at least one of nitrogen, sulfur and oxygen; and any of phenyl, naphthyl, benzyl, monocyclic heterocyclic radical or bicyclic heterocyclic fused ring radical in which up to two hydrogens on the ring have been replaced by substituent groups which may be the same or different and are selected from the group consisting or methyl, methoxy, methylthio, chloro, bromo, CF₃ or nitro, provided that when R² is H or C₁ to C₄ alkyl, R³ must be H or C₁ to C₄ alkyl.

Method A

The alpha-methylstyrene derivative is reacted with a peracid such as peracetic acid or perbenzoic acid, generally by mixing the alpha-methylstyrene derivative with glacial acetic acid and adding concentrated sulfuric acid and the peracid thereto generally with the peracid in an excess amount. The resulting mixture is usually heated for an extended period at a temperature of about 25° to 65° C. Following the reaction period the reaction mixture is diluted with water and a solvent such as methylene chloride. The solvent layer is separated, washed, neutralized, dried and the solvent removed in vacuo. The resulting product, a carbinol, is mixed with methanol and a small amount of p-toluenesulfonic acid and the mixture refluxed for about 4 to 24 hours, and the diol product isolated as before. The following reactions are illustrative.

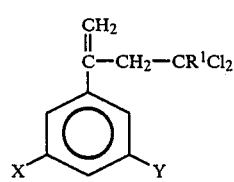

+ 40% CH₃COOOH ⟶

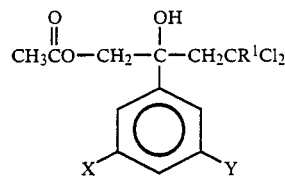

↓ CH₃OH

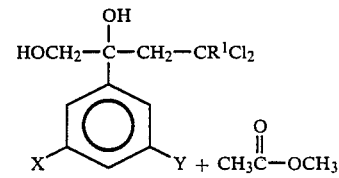

+ CH₃C—OCH₃
     ‖
     O

R¹, X and Y are as identified hereinabove.

Method B

The diol may also be prepared from the appropriate substituted oxiran compound, representative of the latter being described and their preparation shown in U.S. Pat. No. 4,211,549. An appropriate oxirane of the following formula

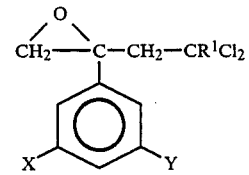

Wherein R¹, X and Y are as identified hereinabove, is treated with sodium acetate in acetic acid, forming the glycol acetate in high yield and purity and then converting the latter to the diol, i.e., glycol, with methanol and a catalytic amount of p-toluenesulfonic acid according to the following general equations wherein, again, R¹, X and Y are as defined hereinabove.

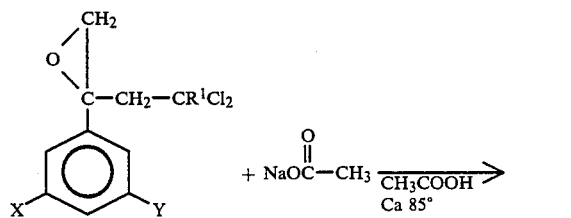

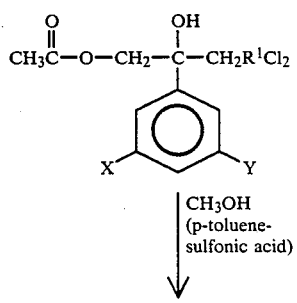

-continued

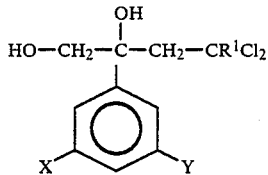

The diol, or glycol, prepared by either Method A or Method B is then reacted with the appropriate sulfonyl chloride in the presence of a suitable amine in benzene medium. A suitable amine usable in all such preparations is pyridine which may also be used as the reaction medium in place of benzene.

Method C

In a preferred one step method of preparation from the appropriate oxirane compound, two equivalents of the requisite sulfonic acid monohydrate are dissolved in benzene and heated at reflux until the water of hydration is removed. Then one equivalent of pyridine along with the one equivalent of the appropriate oxirane is added to the solution remaining after the drying operation and the mixture is refluxed for about 4 hours. Thereafter the reaction mixture is allowed to cool, and is washed with water containing a base such as sodium bicarbonate to remove excess sulfonic acid. The organic layer is separated and dried and the solvents present removed under vacuum. The residue is recrystallized from a suitable solvent such as methyl cyclohexane, providing desired glycol sulfonate or sulfamate product in good yield and purity in one step where the requisite oxirane is available.

Method D

In another preferred one-step method of preparation, at least one equivalent of the requisite sulfonic acid monohydrate is dissolved in benzene and heated at reflux until the water of hydration is removed. Then one equivalent of a weak base such as dimethylformamide is added so that an equilibrium system is created involving the free sulfonic acid and weak base on the one hand and the resulting respective deprotonated sulfonic acid and protonated weak base on the other. One equivalent of the appropriate oxirane is reacted with the equilibrium system and the reaction mixture is heated at about 20° to about 120° C. for about 1 to about 6 hours. Thereafter, the reaction mixture is allowed to cool and the desired sulfonate can be isolated and purified as described in Method C.

The esters are prepared rather simply by reaction of the glycol sulfonae or sulfamate with about 3 moles of acetic anhydride per mol of glycol sulfonate or sulfamate in the presence of about an equimolar amount of 4-dimethylaminopyridine in an aprotic solvent medium such as benzene. Reaction usually takes place with constant stirring at about room temperature in about 1 to 2 hours. The reaction mixture may be worked up in good yield and purity by washing it sequentially with water, dilute hydrochloric acid containing methanol, and a solution of aqueous sodium hydroxide, after which the organic layer is dried over anhydrous sodium sulfate and the solvent removed in vacuo leaving a crystalline product. Recrystallization from methylcyclohexane may be carried out, if desired, to further improve purity.

As indicated hereinabove, it is believed the glycol sulfonate or sulfamate component of the composition of the invention functions in a special way by inhibiting certain protective mechanisms of susceptible weeds, typically an enzymatic detoxification of the triazine component within the plant tissues. This is particularly evident in susceptible weeds at early growth stages. In addition to inhibiting the detoxification mechanism towards triazines, by, for example, interfering with the action at plant enzymes such as glutathione-S-transferase in the case of grassy weeds, the glycol sulfonate or sulfamate component also contributes inherent herbicidal activity by inhibiting or slowing plant growth. The mechanism of action of the present composition with respect to broadleaf weeds has not been delineated, but the end result observed in terms of enhanced activity is substantially the same as with grassy weeds.

The mechanisms for detoxification of the triazines within plant tissues have been described. See the text "Metabolism of Herbicides In Higher Plants", K. K. Hatzios and D. Penner, Burgess Publishing Company, Minneapolis, Minn. 1982, pp. 43–49. The inhibition by glycol sulfonates or sulfamates and their oxirane metabolites of the detoxification reaction within grassy weeds has only now been observed. While physiological investigations show that the detoxification of triazines may occur at quite low levels of glycol sulfonate or sulfamate the surprisingly enhanced effectiveness of the triazine component is often not observable upon gross observations of plant growth if the glycol sulfonate or sulfamate component is applied in admixture at rates below about 0.125 lb/acre. This is because other factors affecting growth of weed plants are ofent of sufficient magnitude to have equal or greater significance. Thus, as a practical matter, it is usually of advantage to use sufficient of the present composition to provide at least 0.125 lb/acre and preferably at least 0.25 to 0.5 lb/acre of the glycol sulfonate or sulfamate to assuredly obtain marked enhancement of the triazine activity while also contributing the herbicidal effect of the glycol sulfonate or sulfamate.

These limits could arise in part because of differing rates of metabolism of the glycol sulfonate or sulfamate component and triazine component within plant tissues. While the oxiranes described in said copending application Ser. No. 445,300 are significantly volatile, the glycol sulfonates and glycol sulfamates employed in the present invention are not nearly so volatile and when properly formulated and employed convert to oxirane compounds only within plant tissues where volatility is not a problem.

Weeds that are not susceptible by virtue of innate characteristics or by virtue of having matured to a stage, such as about the 8 to 10 leaf stage, appear to generate protective detoxifying enzyme material in an amount which overcomes the inhibition by the glycol sulfonate or sulfamate. This is clearly the case with tolerant crops, e.g., corn or sorghum.

The herbicidal mixture of the present invention, in which the activity of the triazine component is enhanced, exhibits more than an additive effect in the control of grassy weeds, especially yellow foxtail and giant foxtail, i.e., Setaria species, and crabgrass, shattercane, proso millet, johnsongrass and barnyard grass, as well as broadleaf weeds such as cocklebur, velvetleaf, jimsonweed, coffeeweed, teaweed and sicklepod when applied postemergently at a dose in the range of about ⅝ (i.e., 0.625) to about 3 pounds per acre of active ingredients wherein the individual components are present within the critical range of ratios of about 1 to about 20 parts by weight of the triazine component to 1 to 2 parts of the glycol sulfonate or sulfamate compound, but in which there is provided at least about 0.125 lb/acre and preferably about 0.25 to 0.5 lb/acre of such compound. It is more preferred that said ratio is about 1 to about 8 parts triazine component per part of glycol sulfonate or sulfamate compound within the limits set forth as follows.

The total amount of active material applied is preferably about ⅝ (i.e., 0.625) to about 3 pounds per acre, and most preferably about 1.25 to about 2.5 lbs/acre, preferably of the mixture of any one or more of atrazine or cyanazine with any of 4,4,4-trichloro-2-(3,5-dichlorophenyl)-2-hydroxybutyl-1-(4-methylphenyl)sulfonate; 4,4,4-trichloro-2-(3,5-dibromophenyl)-2-hydroxybutyl-1-(4-methylphenyl)sulfonate; 4,4,4-trichloro-2-(3-chlorophenyl)-2-hydroxybutyl-1-(4-methylphenyl)sulfonate; and 4,4,4-trichloro-2-(3,5-dichlorophenyl)-2-hydroxybutyl-1-(2,5-dichlorophenyl)sulfonate; and most preferably with 4,4,4-trichloro-2-(3,5-dichlorophenyl-2-hydroxybutyl-1-(4-methylphenyl)sulfonate. Such combinations are most preferred for controlling weeds in corn and sorghum.

Where crop oil is used, it may be employed at the rate of approximately 0.2 parts to about 2.0 parts crop oil per part of combined active ingredients, but more preferably about 1 to 2 parts crop oil per part of the most preferred triazine-glycol sulfonate or sulfamate combinations. Wherein the herbicide concentrate employed does not contain crop oil, the same may be added during preparation of the tank mix for field use.

In formulating the present herbicidal compositions, it is essential to maintain the relative proportions specified hereinabove and to provide an effective amount of the active components in the finished tank mix composition in order to obtain the desired enhanced herbicidal effect. The concentration of the active components considered together in liquid formulations employed to supply the desired dosage for field application generally is from about 0.00001 to about 50 percent by weight although compositions employing as high as a 90 percent concentration may be employed depending on the type of concentrate and the concentration achievable therein and generally at a concentration of at least 0.01 percent by weight.

In compositions to be employed as concentrates, the mixture of herbicidal components may be present in admixture in a carrier therefor at a concentration of from about 5 to about 90 percent by weight, although concentrations of suspension emulsions containing significantly more than about 50 percent by weight combined active ingredients are not readily prepared, and generally the practical upper limit for most wettable powder formulations of the invention is about 80 percent by weight of total active components, while a water dispersible granule product may be made to contain as high as about 90 percent by weight active ingredients.

The triazine component may be supplied separately, if desired, as any of a flowable suspension concentrate, a wettable powder, a dispersible granule type formulation or an emulsifiable concentrate, while the glycol sulfonate or sulfamate compound may be conveniently supplied as an emulsion concentrate, wettable powder or water dispersible granular material, and the two combined in appropriate amounts in aqueous medium in a tank mix containing the two active components in the range of weight ratios recited hereinabove for field application. An emulsion concentrate wettable powder or water dispersible granule containing the glycol sulfonate or sulfamate may be made up into a tank mix together with most any of the commercially supplied concentrates of the herbicidal triazines.

The herbicidal triazines are presently marketed in wettable powder form, in the form of a water dispersible granule and as a flowable suspension concentrate. These are prepared basically as described hereinabove for the combination concentrate of the invention, by grinding the components together and granulating in the case of the granular product.

The glycol sulfonates or sulfamates when supplied separately are expected to be in the form of emulsion concentrates rather readily prepared from the technical grade crystalline form of unmodified active ingredient. See the discussion hereinabove of emulsion concentrates.

A suitable emulsion concentrate of glycol sulfonate or sulfamate compound contains, by weight, 43 percent of the glycol compound, 3.25 percent of Sponto P10-20P alkaryl sulfonate salt, 1.75 percent of a blend of Makon 30 and Makon 14 alkylphenol ethoxylates and the balance Tenneco 500-100 solvent and inerts.

As indicated hereinabove, the present herbicidal combination is tolerated well by crops, such as corn and sorghum or certain broadleaf and plantation crops while controlling in an enhanced manner a number of grassy weeds and broadleaf weeds occurring in such crops and also controlling other weeds, albeit in an effective, but not necessarily surprising enhanced manner. The specified weeds are not each controlled in an enhanced manner by each specified herbicide combination throughout the specified application rates broadly specified herein, but substantially throughout the range of rates. The range of effective dosage rates for each combination may readily be determined by those skilled in the art with the present teachings at hand. Accordingly, the present composition is useful throughout the range of compositions set forth and described herein. At lower ratios of triazine to glycol sulfonate or sulfamate compound enhanced activity of the components towards many grassy and broadleaf weeds is exhibited, while at higher ratios, enhancement is exhibited towards many grassy weeds but activity towards many broadleaf weeds, though excellent, tends not to evidence enhancement.

The triazines in general are not at all well tolerated by such crops as sugar beets, tobacco, oats or many vegetable crops and this property seems unaffected by the other components utilized in the present composition, but as indicated above, weeds are nonetheless controllable in those crops that are either inherently tolerant or are amenable to methods which minimize direct exposure to the present composition.

The enhanced action referred to herein is most definitely and advantageously exhibited upon making a postemergent application to the foliage of the noxious weeds while in about the 2 to 6 leaf stage, preferably 2 to 4 leaf stage, and in the presence of the tolerant crop.

DESCRIPTION OF ILLUSTRATIVE EMBODIMENTS

The following examples illustrate the novel herbicidal compositions of the invention and the method of their use, but as such should not be construed as limitations upon the overall scope of the invention herein contemplated.

EXAMPLE 1

Method A

A wettable powder containing both herbicidal triazine and glycol sulfonate or sulfamate is made up as follows:

Atrazine is air milled or hammer milled to less than 20 micron volume or mass median diameter, preferably to less than 10 microns and optimally to a size in the 1 to 5 micron range. The comminuted atrazine is blended thoroughly with 4,4,4-trichloro-2-(3,5-dichlorophenyl)-2-hydroxybutyl-1-(4-methylphenyl)sulfonate, and with a surfactant and a dispersant, antifoaming additive and a precipitated hydrated silica according to the following composition:

| Components | Weight % |
| --- | --- |
| 4,4,4-trichloro-2-(3,5-dichlorophenyl)-2-hydroxybutyl-1-(4-methylphenyl)sulfonate | 20 |
| Atrazine | 60 |
| Morwet DB (alkylaryl sulfonate) | 4 |
| Polyfon H (lignosulfonate) | 2 |
| Dow Corning Antifoam A (dimethoxysiloxane) | 0.1 |
| Hi Sil 233 (ppt hydrated silica and inerts) | 13.9 |

Method B

The entire composition set forth immediately above is air milled until the atrazine reaches the requisite fineness.

On dispersing either of the foregoing compositions in water at the respective rates of 2, 3, 4 and 5 lbs. of the wettable powder in, respectively, 10 and 20 gallons of water, a series of tank mixes is obtained in which the atrazine is uniformly suspended and the glycol sulfonate is uniformly dispersed in either emulsified form or in suspended form sorbed on the carrier particles and the tank mixes are readily sprayable in postemergent applications.

EXAMPLE 2

A wettable powder of atrazine and glycol sulfonate is made up in a manner similar to that described in Example 1 but having the following composition:

| Components | Weight % |
| --- | --- |
| 4,4,4-trichloro-2-(3,5-dibromophenyl)-2-hydroxybutyl-1-(4-methylphenyl)sulfonate | 26.6 |
| Atrazine | 53.2 |
| Makon 10 (alkylphenol ethoxylate) | 3.0 |
| Daxad #27 (polymerized alkylaryl sulfonate) | 3.0 |
| Hi Sil 233 | 7.0 |
| Barden clay (kaolin) and inert | 7.0 |

A portion of the blended material is made up in a series of tank mixes as in Example 1 and the same fine results are observed.

Other portions of the blended wettable powder are pan agglomerated on the addition of, respectively 20, 30 and 40 percent by weight water and carrying out conventional agglomeration techniques and thereafter drying the resulting particles to a moisture content in the range of about 1.5 to about 3 percent by weight. The resulting products are each water dispersible granular products which form excellent stable, sprayable tank mixes when mixed with water at the same rates as set forth for the wettable powders of Example 1.

Similar fine results are obtained when the silica and Barden clay of Examples 1 and 2 are replaced with other carriers such as the ball and kaolin clays, diatomites and silicates. Both nonionic and anionic surface-active agents may be used alternatively in the concentration range of about 2 to 10 percent by weight, preferably 2 to 6 percent and most preferably about 4 to about 6 percent.

EXAMPLE 3

A suspension-emulsion concentrate is prepared from atrazine and from 4,4,4-trichloro-2-(3-chlorophenyl)-2-hydroxybutyl-1-(4-methylphenyl)sulfonate. The atrazine is first wet milled in a xylene range petroleum distillate, Tenneco 500-100, or in a phytobland crop oil to a fineness in the range described in Example 1 and thereafter the requisite amounts of glycol sulfonate and surface-active materials are added to suspend the atrazine and emulsify the glycol compound, producing a suspension emulsion having, in respective runs, the following compositions:

| Components | Weight % |
| --- | --- |
| Composition A | |
| 4,4,4-trichloro-2-(3-chlorophenyl)-2-hydroxybutyl-1-(4-methylphenyl)sulfonate | 16 |
| Atrazine | 36 |
| Daxad 11 sulfonated naphthalene formaldehyde condensate | 4 |
| Bentone 34 clay gellant | 0.8 |
| Triton X-100 alkylaryl alkoxylate | 3 |
| Tenneco 500-100 solvent | balance |
| Composition B | |
| 4,4,4-trichloro-2-(3-chlorophenyl)-2-hydroxybutyl-1-(4-methylphenyl)sulfonate | 16 |
| Atrazine | 36 |
| Polyfon H lignosulfonate | 2 |
| Bentone 34 clay gellant | 0.4 |
| Triton X-100 alkylaryl alkoxylate | 3 |
| Tween 85 sorbitan trioleate | 3 |
| Sun Spray 11 N crop oil | 10 |
| Tenneco 500-100 petroleum distillate | balance |
| Composition C | |
| 4,4,4-trichloro-2-(3-chlorophenyl)-2-hydroxybutyl-1-(4-methylphenyl)sulfonate | 16 |
| Atrazine | 36 |
| Bentone 34 clay gellant | 0.8 |
| Triton X-100 alkylaryl alkoxylate | 3 |
| Witconate P-1220 alkylaryl sulfonate calcium salt | 3 |
| Tenneco 500-100 solvent | balance |

The resulting suspension-emulsion concentrates obtained in each case hold the atrazine smoothly suspended and the glycol sulfonate emulsified in the concentrate as well as in the tank mix obtained in blending the concentrate with water at the rate of 3 pounds per 30 gallons of water and the tank mix is readily sprayable.

Similar excellent concentrates are obtained when compositions are made up containing, by weight, from 12 to 16 percent of the glycol sulfonate or sulfamate and from 32 to 36 percent atrazine with ratios between the actives in accordance with the present invention, and on using from 4 to 6 percent of the Daxad 11 or Morwet D425 sulfonated naphthalene-formaldehyde condensate, 4 to 6 percent of Polyfon H or Marosperse CBO-3 lignosulfonate, from 2 to 8 percent Bentone BE or Attagel 50 clay gellant, from 2 to 4 percent of Witconate P1220 or Sponto AC31-2 alkylaryl sulfonate as the calcium salt or mixed amine salts, from 2 to 6 percent of Triton X-100 or T-Det N-15 alkylaryl alkoxylate, or Polyglycol 26-3, and the balance Tenneco 500-100 or Aromatic 100 xylene range petroleum distillate or other phytobland oil.

EXAMPLE 4

An oil-based flowable suspension concentrate is prepared from atrazine and from 4,4,4-trichloro-2-(3,5-dichlorophenyl)-2-hydroxybutyl-1-(1-methylethyl)sulfamate. The atrazine and the sulfamate are first wet milled together in a portion of the crop oil concentrate Sunspray 11N to a fineness in the range described in Example 1 and thereafter the requisite amounts of surface-active materials and the balance of the crop oil concentrate are added to suspend the finely-ground and milled active ingredients and produce the following composition:

| Components | Weight % |
|---|---|
| Glycol Sulfamate | 16 |
| Atrazine | 36 |
| Polyfon H lignosulfonate | 2 |
| Emulsogen M alkyl ethoxylate | 6 |
| Sunspray 11N crop oil concentrate | balance |

EXAMPLE 5

Method A 0.125 Gallons of an emulsion concentrate containing, by weight, 43 percent of 4,4,4-trichloro-2(3,5-dichlorophenyl)-2-hydroxybutyl-1-(4-methylphenyl)sulfonate, 3.2 percent of Sponto P10-20P calcium dodecylbenzene sulfonic acid, 1.75 percent of nonionic surfactants consisting of nonyl phenol condensed with from 14 to 30 moles of ethylene oxide, about 46 percent petroleum distillate and the balance inerts is thoroughly dispersed in 10 gallons of water.

3.5 Pounds of a commercial flowable suspension concentrate of atrazine triazine herbicide containing, by weight 43 percent of the triazine in addition to surfactants and/or dispersants and solid suspension aids is thoroughly dispersed in 10 gallons of water.

10 Gallons of the dispersed glycol sulfonate and 10 gallons of the suspended triazine are thoroughly mixed together to provide a tank mix containing, by weight, 0.3 percent of the glycol sulfonate and 0.9 percent of the triazine. On applying 20 gallons per acre to cropland there is provided 0.5 pounds per acre of the glycol sulfonate compound and 1.5 pounds per acre of the triazine.

Method B

The atrazine flowable suspension concentrate and the emulsion concentrate of glycol sulfonate are thoroughly mixed together initially in about 7 to 10 gallons of water and the balance of 20 gallons of water, i.e., 13 to 10 gallons of additional water is combined with the initial aqueous dispersion to form a tank mix with the same characteristics as described using Method A.

EXAMPLE 6

In a series of test carried out to demonstrate the enhancement of the triazine herbicidal activity obtained on applying combinations of several different glycol sulfonates in combination, respectively, with one of the herbicidal triazines, viz., atrazine, for weed control, giant foxtail plants that had been grown in light sandy soil in the greenhouse to a height of about 3 to 3½ inches and were at the 4 to 4½ leaf stage were treated postemergently as follows.

Each of the compounds 4,4,4-trichloro-2-(3,5-dichlorophenyl)-2-hydroxybutyl-1-methylsulfonate (Compound A); 4,4,4-trichloro-2-(3,5-dichlorophenyl)-2-hydroxybutyl-1-ethylsulfonate (Compound B); and 4,4,4-trichloro-2-(3,5-dichlorophenyl)-2-hydroxybutyl-1-(1-methylethyl)sulfonate (Compound C) were made up as an emulsion concentrate consisting of, by weight, 12 percent of compound under test, 5% of Atlox 3403F and 5% Atlox 3404F surfactants, each a proprietary blend of calcium dodecyl benzene sulfonate, aryl ethoxylates and ethoxylated sorbitans, and the balance xylene. Various dilutions of the emulsion concentrates were made up in aqueous sprayable mixes each containing 1 percent by weight of Atplus 411F crop oil concentrate, a commercial product consisting of 17 percent by weight of Atplus 300F surfactant and the balance a non-phytotoxic paraffinic oil of a type suitable to use in spraying dormant fruit trees. Atplus 300F surfactant is a proprietary blend of calcium dodecyl benzene sulfonate and TWEEN 85, a sorbitan trioleate, plus polyoxyethylsorbitan fatty acid esters.

The requisite amounts of each glycol sulfonate compound concentrate were used to provide spray mixes containing, respectively, 0.05; 0.027; 0.0125; and 0.0065 lb of compound per gallon, corresponding to field rates of about 1.6 lb; 0.8 lb; 0.4 lb and 0.2 lb/acre when applied with a track sprayer at a rate of 30 gal/acre.

Atrazine was provided in the form of the commercial product AATREX 4L flowable concentrate containing by weight, 42 percent atrazine, and surfactant plus suspension aids. The requisite amounts of flowable concentrate were thoroughly and vigorously mixed with water containing 1 percent by weight Atplus 411F crop oil concentrate to provide a series of spray mixes containing 0.4; 0.2; 0.1; and 0.05 percent by weight atrazine, thus providing for application rates of 1; 0.5; 0.25 and 0.125 lb/acre of atrazine when sprayed at the rate of 30 gal/acre.

Additional spray mixes were made up containing the respective test compounds in descending order of concentrations as set forth above together with atrazine in the descending order of concentrations set forth above, thus providing serial dilutions of compositions containing both types of active ingredients in combination.

The giant foxtail seedlings had been grown in pots and the soil was then shielded with about 0.5 inch of vermiculite while the plants were treated in respective groups of about 12 to 15 plants with 2 replicates of each group. Each of the 28 tank mixes described plus an aqueous surfactant blank were applied to respective sets of replicated groups of giant foxtail plants by spraying thereon at the rate of 30 gal/acre and then removing the vermiculite immediately. The plants were then maintained under good growing conditions in the greenhouse for two days and then were examined to ascertain the extent of control, i.e., reduction in growth, obtained and scored on the basis of 0 to 100 where 100 represents kill of the plants and 0 represents no reduction in growth.

The plants were examined again after 12 days and the extent of control ascertained.

The results of these runs including both evaluations are summarized in Tables 1 and 2 wherein the percent control readings are averaged for each set for replicates.

Also shown in Tables 1 and 2 is the extent of increased control over expected control. The expected control was calculated according to the well know equation:

$$\text{Expected Control} = a + b - \frac{a \times b}{100}$$

where a = % control by atrazine alone and b = % control by glycol sulfonate alone.

TABLE 1

Control of Giant Foxtail (Evaluation After 2 Days)

| Run Number | Aztrazine Dosage lb/acre | Glycol Sulfonate Compound | Sulfonate Dosage, lb mol/acre × 1000 | Approx. Wt. Ratio, Atrazine to Sulfonate | Expected Control % | Actual Control % | Percent Increase Over Expected Control |
|---|---|---|---|---|---|---|---|
| 1 | 1 | — | — | — | — | 50 | — |
| 2 | 0.5 | — | — | — | — | 30 | — |
| 3 | 0.25 | — | — | — | — | 10 | — |
| 4 | 0.125 | — | — | — | — | 0 | — |
| 5 | — | A | 3.12 | — | — | 20 | — |
| 6 | — | A | 1.56 | — | — | 10 | — |
| 7 | — | A | 0.78 | — | — | 0 | — |
| 8 | — | A | 0.39 | — | — | 0 | — |
| 9 | — | B | 3.12 | — | — | 10 | — |
| 10 | — | B | 1.56 | — | — | 0 | — |
| 11 | — | B | 0.78 | — | — | 0 | — |
| 12 | — | B | 0.39 | — | — | 0 | — |
| 13 | — | C | 3.12 | — | — | 20 | — |
| 14 | — | C | 1.56 | — | — | 20 | — |
| 15 | — | C | 0.78 | — | — | 20 | — |
| 16 | — | C | 0.39 | — | — | 10 | — |
| 17 | 1 | A | 3.12 | 1 to 1.6 | 60 | 70 | 17 |
| 18 | 0.5 | A | 1.56 | 1 to 1.6 | 37 | 70 | 89 |
| 19 | 0.25 | A | 0.78 | 1 to 1.6 | 10 | 40 | 300 |
| 20 | 0.125 | A | 0.39 | 1 to 1.6 | 0 | 30 | ∞ |
| 21 | 1 | B | 3.12 | 1 to 1.6 | 55 | 50 | −9 |
| 22 | 0.5 | B | 1.56 | 1 to 1.6 | 30 | 50 | 67 |
| 23 | 0.25 | B | 0.78 | 1 to 1.6 | 10 | 40 | 300 |
| 24 | 0.125 | B | 0.39 | 1 to 1.6 | 0 | 20 | ∞ |
| 25 | 1 | C | 3.12 | 1 to 1.6 | 60 | 70 | 17 |
| 26 | 0.5 | C | 1.56 | 1 to 1.6 | 44 | 60 | 36 |
| 27 | 0.25 | C | 0.78 | 1 to 1.6 | 28 | 60 | 114 |
| 28 | 0.125 | C | 0.39 | 1 to 1.6 | 10 | 30 | 200 |

Compound A = 4,4,4-trichloro-2-(3,5-dichlorophenyl)-2-hydroxybutyl-1-methylsulfonate
Compound B = 4,4,4-trichloro-2-(3,5-dichlorophenyl)-2-hydroxybutyl-1-ethylsulfonate
Compound C = 4,4,4-trichloro-2-(3,5-dichlorophenyl)-2-hydroxybutyl-1-(1-methylethyl)-sulfonate

TABLE 2

Control of Giant Foxtail (Evaluation After 12 Days)

| Run Number | Aztrazine Dosage lb/acre | Glycol Sulfonate Compound | Sulfonate Dosage, lb mol/acre × 1000 | Approx. Wt. Ratio, Atrazine to Sulfonate | Expected Control % | Actual Control % | Percent Increase Over Expected Control |
|---|---|---|---|---|---|---|---|
| 1 | 1 | — | — | — | — | 30 | — |
| 2 | 0.5 | — | — | — | — | 10 | — |
| 3 | 0.25 | — | — | — | — | 0 | — |
| 4 | 0.125 | — | — | — | — | 0 | — |
| 5 | — | A | 3.12 | — | — | 0 | — |
| 6 | — | A | 1.56 | — | — | 0 | — |
| 7 | — | A | 0.78 | — | — | 0 | — |
| 8 | — | A | 0.39 | — | — | 0 | — |
| 9 | — | B | 3.12 | — | — | 10 | — |
| 10 | — | B | 1.56 | — | — | 0 | — |
| 11 | — | B | 0.78 | — | — | 0 | — |
| 12 | — | B | 0.39 | — | — | 0 | — |
| 13 | — | C | 3.12 | — | — | 10 | — |
| 14 | — | C | 1.56 | — | — | 0 | — |
| 15 | — | C | 0.78 | — | — | 0 | — |
| 16 | — | C | 0.39 | — | — | 0 | — |
| 17 | 1 | A | 3.12 | 1 to 1.6 | 30 | 40 | 33 |
| 18 | 0.5 | A | 1.56 | 1 to 1.6 | 10 | 40 | 300 |
| 19 | 0.25 | A | 0.78 | 1 to 1.6 | 0 | 30 | ∞ |
| 20 | 0.125 | A | 0.39 | 1 to 1.6 | 0 | 0 | 0 |
| 21 | 1 | B | 3.12 | 1 to 1.6 | 37 | 40 | 8 |
| 22 | 0.5 | B | 1.56 | 1 to 1.6 | 10 | 30 | 200 |
| 23 | 0.25 | B | 0.78 | 1 to 1.6 | 0 | 30 | ∞ |
| 24 | 0.125 | B | 0.39 | 1 to 1.6 | 0 | 0 | 0 |

TABLE 2-continued

Control of Giant Foxtail (Evaluation After 12 Days)

| Run Number | Aztrazine Dosage lb/acre | Glycol Sulfonate Compound | Sulfonate Dosage, lb mol/acre × 1000 | Approx. Wt. Ratio, Atrazine to Sulfonate | Expected Control % | Actual Control % | Percent Increase Over Expected Control |
| --- | --- | --- | --- | --- | --- | --- | --- |
| 25 | 1 | C | 3.12 | 1 to 1.6 | 37 | 40 | 8 |
| 26 | 0.5 | C | 1.56 | 1 to 1.6 | 10 | 40 | 300 |
| 27 | 0.25 | C | 0.78 | 1 to 1.6 | 0 | 40 | ∞ |
| 28 | 0.125 | C | 0.39 | 1 to 1.6 | 0 | 10 | 0 |

Compound A = 4,4,4-trichloro-2-(3,5-dichlorophenyl)-2-hydroxybutyl-1-methylsulfonate
Compound B = 4,4,4-trichloro-2-(3,5-dichlorophenyl)-2-hydroxybutyl-1-ethylsulfonate
Compound C = 4,4,4-trichloro-2-(3,5-dichlorophenyl)-2-hydroxybutyl-1-(1-methylethyl)-sulfonate

EXAMPLE 7

Additional glycol sulfonate compounds as well as a glycol sulfamate compound were made up as emulsion concentrates and each further made into spray mixes of the same concentrates together with crop oil concentrate and a similar manner as described in Example 6. AATREX 4L commercial atrazine flowable concentrate was used to make up a spray mix containing 0.3 percent by weight atrazine providing 0.75 lb/acre atrazine when sprayed at the rate of 30 gal/acre.

The glycol sulfonate and sulfamate emulsion concentrates were also made up into spray mixes together with atrazine at the same concentrations as described in Example 6 but with the same concentration of atrazine, 0.3 percent by weight, at each level of dilution of the glycol sulfonate or sulfamate.

Greenhouse grown giant foxtail seedlings 3 inches tall and at the 3 to 3½ leaf stage were sprayed as in Example 6 (replicate pots of about 12 to about 15 plants each for each treatment) while the soil was shielded with vermiculite and the vermiculite promptly removed after spraying.

The plants were kept under good growing conditions and the results evaluated after 13 days. The extent of control on a 0 to 100 scale was recorded and is tabulated in Table 3.

Some of the same compounds were subjected to the same testing procedure on giant foxtail at the 3 leaf stage, alone and in combination with atrazine, the latter at a constant 0.75 lb/acre rate. Again, crop oil concentrate was added to each mix as described in Example 6. The results were evaluated after 12 days and are tabulated in Table 4.

The compounds tested are identified in the footnote to Table 3.

TABLE 3

Control of Giant Foxtail

| Run Number | Aztrazine Dosage lb/acre | Glycol Sulfonate Compound | Sulfonate Dosage, lb mol/acre × 1000 | Approx. Wt. Ratio, Atrazine to Sulfonate | Expected Control % | Actual Control % | Percent Increase Over Expected Control |
| --- | --- | --- | --- | --- | --- | --- | --- |
| 29 | 0.75 | — | — | — | — | 37 | — |
| 30 | — | D | 3.12 | — | — | 10 | — |
| 31 | — | D | 1.56 | — | — | 0 | — |
| 32 | — | D | 0.78 | — | — | 0 | — |
| 33 | — | E | 3.12 | — | — | 5 | — |
| 34 | — | E | 1.56 | — | — | 0 | — |
| 35 | — | E | 0.78 | — | — | 0 | — |
| 36 | — | F | 3.12 | — | — | 20 | — |
| 37 | — | F | 1.56 | — | — | 0 | — |
| 38 | — | F | 0.78 | — | — | 0 | — |
| 39 | — | G | 3.12 | — | — | 0 | — |
| 40 | — | G | 1.56 | — | — | 0 | — |
| 41 | — | G | 0.78 | — | — | 0 | — |
| 42 | — | H | 3.12 | — | — | 0 | — |
| 43 | — | H | 1.56 | — | — | 0 | — |
| 44 | — | H | 0.78 | — | — | 0 | — |
| 45 | 0.75 | D | 3.12 | 1 to 2 | 43 | 80 | 86 |
| 46 | 0.75 | D | 1.56 | 1 to 1 | 37 | 80 | 116 |
| 47 | 0.75 | D | 0.78 | 2 to 1 | 37 | 50 | 35 |
| 48 | 0.75 | E | 3.12 | 1 to 2 | 40 | 100 | 150 |
| 49 | 0.75 | E | 1.56 | 1 to 1 | 37 | 90 | 143 |
| 50 | 0.75 | E | 0.78 | 2 to 1 | 37 | 50 | 35 |
| 51 | 0.75 | F | 3.12 | 1 to 2 | 50 | 90 | 80 |
| 52 | 0.75 | F | 1.56 | 1 to 1 | 37 | 85 | 130 |
| 53 | 0.75 | F | 0.78 | 2 to 1 | 37 | 50 | 35 |
| 54 | 0.75 | G | 3.12 | 1 to 2 | 37 | 50 | 35 |
| 55 | 0.75 | G | 1.56 | 1 to 1 | 37 | 60 | 62 |
| 56 | 0.75 | G | 0.78 | 2 to 1 | 37 | 55 | 49 |
| 57 | 0.75 | (H*) | 3.12 | 1 to 2 | 37 | 60 | 62 |
| 58 | 0.75 | (H*) | 1.56 | 1 to 1 | 37 | 70 | 89 |

TABLE 3-continued

Control of Giant Foxtail

| Run Number | Aztrazine Dosage lb/acre | Glycol Sulfonate Compound | Sulfonate Dosage, lb mol/acre × 1000 | Approx. Wt. Ratio, Atrazine to Sulfonate | Expected Control % | Actual Control % | Percent Increase Over Expected Control |
|---|---|---|---|---|---|---|---|
| 59 | 0.75 | (H*) | 0.78 | 2 to 1 | 37 | 60 | 62 |

*Compound H is a glycol sulfamate
Compound D = 4,4,4-trichloro-2-(3,5-dichlorophenyl)-2-hydroxybutyl-1-(2-methoxycarbonylphenyl)sulfonate
Compound E = 4,4,4-trichloro-2-(3,5-dichlorophenyl)-2-hydroxybutyl-1-(4-methylphenyl)-sulfonate
Compound F = 4,4,4-trichloro-2-(3,5-dichlorophenyl)-2-hydroxybutyl-1-phenylmethylsulfonate
Compound G = 4,4,4-trichloro-2-(3,5-dichlorophenyl)-2-hydroxybutyl-1-chloromethylsulfonate
Compound H = 4,4,4-trichloro-2-(3,5-dichlorophenyl)-2-hydroxybutyl-1-(1-methylethyl)sulfamate

TABLE 4

Control of Giant Foxtail

| Run Number | Atrazine Dosage lb/acre | Glycol Sulfonate Compound | Sulfonate Dosage, lb mol/acre × 1000 | Approx. Wt. Ratio, Atrazine to Sulfonate | Expected Control % | Actual Control % | Percent Increase Over Expected Control |
|---|---|---|---|---|---|---|---|
| 60 | 0.75 | — | — | — | — | 48 | — |
| 61 | — | G | 3.12 | — | — | 0 | — |
| 62 | — | G | 1.56 | — | — | 0 | — |
| 63 | — | G | 0.78 | — | — | 0 | — |
| 64 | — | H | 3.12 | — | — | 0 | — |
| 65 | — | H | 1.56 | — | — | 0 | — |
| 66 | — | H | 0.78 | — | — | 0 | — |
| 67 | 0.75 | G | 3.12 | 1 to 2 | 48 | 50 | 4 |
| 68 | 0.75 | G | 1.56 | 1 to 1 | 48 | 60 | 25 |
| 69 | 0.75 | G | 0.78 | 2 to 1 | 48 | 55 | 15 |
| 70 | 0.75 | H | 3.12 | 1 to 2 | 48 | 60 | 25 |
| 71 | 0.75 | H | 1.56 | 1 to 1 | 48 | 70 | 46 |
| 72 | 0.75 | H | 0.78 | 2 to 1 | 48 | 60 | 25 |

Compound G = 4,4,4-trichloro-2-(3,5-dichlorophenyl)-2-hydroxybutyl-1-chloromethylsulfonate
Compound H = 4,4,4-trichloro-2-(3,5-dichlorophenyl)-2-hydroxybutyl-1-(1-methylethyl)sulfamate

EXAMPLE 8

Two of the compounds tested according to Examples 6 and 8 were further tested against greenhouse grown crabgrass and johnsongrass, both at the 3 leaf stage. The spray compositions were made up as described in Example 6 except that each contained 0.6 percent atrazine, providing 1.5 lbs/acre atrazine when sprayed at the rate of 30 gal/acre.

The tests were evaluated after 15 days. The results on crabgrass are tabulated in Table 5, while the results on johnsongrass are tabulated in Table 6.

Expected control and enhancement (as percent increase over expected control) were calculated as described in Example 6.

TABLE 5

Control of Crabgrass

| Run Number | Atrazine Dosage lb/acre | Glycol Sulfonate Compound | Sulfonate Dosage, lb mol/acre × 1000 | Approx. Wt. Ratio, Atrazine to Sulfonate | Expected Control % | Actual Control % | Percent Increase Over Expected Control |
|---|---|---|---|---|---|---|---|
| 73 | 1 | — | — | — | — | 60 | — |
| 76 | — | C | 3.12 | — | — | 35 | — |
| 77 | — | C | 1.56 | — | — | 15 | — |
| 78 | — | C | 0.78 | — | — | 0 | — |
| 79 | — | G | 3.12 | — | — | 45 | — |
| 80 | — | G | 1.56 | — | — | 30 | — |
| 81 | — | G | 0.78 | — | — | 10 | — |
| 82 | 1 | C | 3.12 | 1 to 1.6 | 74 | 90 | 22 |
| 83 | 1 | C | 1.56 | 1.25 to 1 | 66 | 90 | 21 |
| 84 | 1 | C | 0.78 | 2.5 to 1 | 60 | 90 | 50 |
| 85 | 1 | G | 3.12 | 1 to 1.6 | 78 | 100 | 28 |
| 86 | 1 | G | 1.56 | 1.25 to 1 | 72 | 95 | 32 |
| 87 | 1 | G | 0.78 | 2.5 to 1 | 64 | 100 | 56 |

Compound C = 4,4,4-trichloro-2-(3,5-dichlorophenyl)-2-hydroxybutyl-1-(1-methylethyl)sulfonate
Compound G = 4,4,4-trichloro-2-(3,5-dichlorophenyl)-2-hydroxybutyl-1-chloromethylsulfonate

TABLE 6

Control of Johnsongrass

| Run Number | Atrazine Dosage lb/acre | Glycol Sulfonate Compound | Sulfonate Dosage, lb mol/acre × 1000 | Approx. Wt. Ratio, Atrazine to Sulfonate | Expected Control % | Actual Control % | Percent Increase Over Expected Control |
|---|---|---|---|---|---|---|---|
| 88 | 1 | — | — | — | — | 20 | — |
| 89 | — | C | 3.12 | — | — | 5 | — |
| 90 | — | C | 1.56 | — | — | 0 | — |
| 91 | — | C | 0.78 | — | — | 0 | — |
| 92 | 1 | C | 3.12 | 1 to 1.6 | 24 | 90 | 275 |
| 93 | 1 | C | 1.56 | 1.25 to 1 | 20 | 80 | 300 |
| 94 | 1 | C | 0.78 | 2.5 to 1 | 20 | 70 | 250 |
| 95 | — | G | 3.12 | — | — | 30 | — |
| 96 | — | G | 1.56 | — | — | 10 | — |
| 97 | — | G | 0.78 | — | — | 0 | — |
| 98 | 1 | G | 3.12 | 1 to 1.6 | 26 | 95 | 265 |
| 99 | 1 | G | 1.56 | 1.25 to 1 | 22 | 70 | 218 |
| 100 | 1 | G | 0.78 | 2.5 to 1 | 20 | 55 | 175 |

Compound C = 4,4,4-trichloro-2-(3,5-dichlorophenyl)-2-hydroxybutyl-1-(1-methylethyl)sulfonate
Compound G = 4,4,4-trichloro-2-(3,5-dichlorophenyl)-2-hydroxybutyl-1-chloromethylsulfonate

EXAMPLE 9

Additional glycol sulfonates were utilized according to the invention and also tested alone using the procedure of Example 6 as modified in carrying out Example 7, except atrazine, in each case where used, was applied at 1 lb/acre. Also, some warming (to less than 150° F.) was used in preparing the emulsifiable concentrates.

The spray compositions were applied with soil shielding to crabgrass 3½ to 4 inches tall and at the 4½ to 5½ leaf stage and also to giant foxtail 2 to 2½ inches tall and at the 4 leaf stage.

The results were observed and recorded after 3 days and again after 14 days. The tests on crabgrass are tabulated in Tables 7 and 9. The results on johnsongrass are tabulated in Tables 8 and 10.

The compounds tested are identified in the footnote to Table 7.

TABLE 7

Control of Crabgrass
(3 day evaluation)

| Run Number | Atrazine Dosage lb/acre | Glycol Sulfonate Compound | Sulfonate Dosage, lb mol/acre × 1000 | Approx. Wt. Ratio, Atrazine to Sulfonate | Expected Control % | Actual Control % | Percent Increase Over Expected Control |
|---|---|---|---|---|---|---|---|
| 103 | 1 | — | — | — | — | 0 | — |
| 104 | — | E | 3.12 | — | — | 5 | — |
| 105 | — | E | 1.56 | — | — | 5 | — |
| 106 | — | E | 0.78 | — | — | 0 | — |
| 107 | 1 | E | 3.12 | 1 to 1.6 | 5 | 55 | 1000 |
| 108 | 1 | E | 1.56 | 1.25 to 1 | 5 | 45 | 800 |
| 109 | 1 | E | 0.78 | 2.5 to 1 | 0 | 20 | ∞ |
| 110 | — | I | 3.12 | — | — | — | — |
| 111 | — | I | 1.56 | — | — | — | — |
| 112 | — | I | 0.78 | — | — | — | — |
| 113 | 1 | I | 3.12 | 1 to 1.6 | 5 | 40 | 700 |
| 114 | 1 | I | 1.56 | 1.25 to 1 | 0 | 40 | ∞ |
| 115 | 1 | I | 0.78 | 2.5 to 1 | 0 | 15 | ∞ |
| 116 | — | J | 3.12 | — | — | 5 | — |
| 117 | — | J | 1.56 | — | — | 0 | — |
| 118 | — | J | 0.78 | — | — | 0 | — |
| 119 | 1 | J | 3.12 | 1 to 1.6 | 5 | 35 | 600 |
| 120 | 1 | J | 1.56 | 1.25 to 1 | 0 | 40 | ∞ |
| 121 | 1 | J | 0.78 | 2.5 to 1 | 0 | 15 | ∞ |
| 122 | — | K | 3.12 | — | — | 5 | — |
| 123 | — | K | 1.56 | — | — | 0 | — |
| 124 | — | K | 0.78 | — | — | 0 | — |
| 125 | 1 | K | 3.12 | 1 to 1.6 | 5 | 35 | 600 |
| 126 | 1 | K | 1.56 | 1.25 to 1 | 0 | 30 | ∞ |
| 127 | 1 | K | 0.78 | 2.5 to 1 | 0 | 25 | ∞ |

Compound E = 4,4,4-trichloro-2-(3,5-dichlorophenyl)-2-hydroxybutyl-1-(4-methylphenyl)sulfonate
Compound I = 4,4,4-trichloro-2-(3,5-dichlorophenyl)-2-hydroxybutyl-1-(3-trifluoromethylphenyl)sulfonate
Compound J = 4,4,4-trichloro-2-(3,5-dichlorophenyl)-2-hydroxybutyl-1-(4-chlorophenyl)sulfonate
Compound K = 4,4,4-trichloro-2-(3,5-dichlorophenyl)-2-hydroxybutyl-1-(2,4,6-trimethylphenyl)sulfonate

TABLE 8

Control of Giant Foxtail
(3 day evaluation)

| Run Number | Atrazine Dosage lb/acre | Glycol Sulfonate Compound | Sulfonate Dosage, lb mol/acre × 1000 | Approx. Wt. Ratio, Atrazine to Sulfonate | Expected Control % | Actual Control % | Percent Increase Over Expected Control |
|---|---|---|---|---|---|---|---|
| 128 | 1 | — | — | — | — | 15 | — |
| 129 | — | E | 3.12 | — | — | 5 | — |
| 130 | — | E | 1.56 | — | — | 0 | — |
| 131 | — | E | 0.78 | — | — | 0 | — |
| 132 | 1 | E | 3.12 | 1 to 1.6 | 19 | 75 | 295 |
| 133 | 1 | E | 1.56 | 1.25 to 1 | 15 | 85 | 467 |
| 134 | 1 | E | 0.78 | 2.5 to 1 | 15 | 85 | 467 |
| 135 | — | I | 3.12 | — | — | 5 | — |
| 136 | — | I | 1.56 | — | — | 0 | — |
| 137 | — | I | 0.78 | — | — | 0 | — |
| 138 | 1 | I | 3.12 | 1 to 1.6 | 19 | 85 | 347 |
| 139 | 1 | I | 1.56 | 1.25 to 1 | 15 | 80 | 433 |
| 140 | 1 | I | 0.78 | 2.5 to 1 | 15 | 40 | 167 |
| 141 | — | J | 3.12 | — | — | 5 | — |
| 142 | — | J | 1.56 | — | — | 0 | — |
| 143 | — | J | 0.78 | — | — | 0 | — |
| 144 | 1 | J | 3.12 | 1 to 1.6 | 19 | 90 | 374 |
| 145 | 1 | J | 1.56 | 1.25 to 1 | 15 | 55 | 267 |
| 146 | 1 | J | 0.78 | 2.5 to 1 | 15 | 60 | 300 |
| 147 | — | K | 3.12 | — | — | 5 | — |
| 148 | — | K | 1.56 | — | — | 0 | — |
| 149 | — | K | 0.78 | — | — | 0 | — |
| 150 | 1 | K | 3.12 | 1 to 1.6 | 19 | 80 | 321 |
| 151 | 1 | K | 1.56 | 1.25 to 1 | 15 | 65 | 333 |
| 153 | 1 | K | 0.78 | 2.5 to 1 | 15 | 55 | 266 |

Compound E = 4,4,4-trichloro-2-(3,5-dichlorophenyl)-2-hydroxybutyl-1-(4-methylphenyl)sulfonate
Compound I = 4,4,4-trichloro-2-(3,5-dichlorophenyl)-2-hydroxybutyl-1-(3-trifluoromethylphenyl)sulfonate
Compound J = 4,4,4-trichloro-2-(3,5-dichlorophenyl)-2-hydroxybutyl-1-(4-chlorophenyl)sulfonate
Compound K = 4,4,4-trichloro-2-(3,5-dichlorophenyl)-2-hydroxybutyl-1-(2,4,6-trimethylphenyl)sulfonate

TABLE 9

Control of Crabgrass
(14 day evaluation)

| Run Number | Atrazine Dosage lb/acre | Glycol Sulfonate Compound | Sulfonate Dosage, lb mol/acre × 1000 | Approx. Wt. Ratio, Atrazine to Sulfonate | Expected Control % | Actual Control % | Percent Increase Over Expected Control |
|---|---|---|---|---|---|---|---|
| 154 | 1 | — | — | — | — | 90 | — |
| 155 | — | E | 3.12 | — | — | 55 | — |
| 156 | — | E | 1.56 | — | — | 20 | — |
| 157 | — | E | 0.78 | — | — | 0 | — |
| 158 | 1 | E | 3.12 | 1 to 1.6 | 96 | 60 | neg. |
| 159 | 1 | E | 1.56 | 1.25 to 1 | 92 | 30 | neg. |
| 160 | 1 | E | 0.78 | 2.5 to 1 | 90 | 20 | neg. |
| 161 | — | I | 3.12 | — | — | 80 | — |
| 162 | — | I | 1.56 | — | — | 20 | — |
| 163 | — | I | 0.78 | — | — | 0 | — |
| 164 | 1 | I | 3.12 | 1 to 1.6 | 95 | 50 | neg. |
| 165 | 1 | I | 1.56 | 1.25 to 1 | 95 | 45 | neg. |
| 166 | 1 | I | 0.78 | 2.5 to 1 | 95 | 45 | neg. |
| 167 | — | J | 3.12 | — | — | 50 | — |
| 168 | — | J | 1.56 | — | — | 20 | — |
| 169 | — | J | 0.78 | — | — | 0 | — |
| 170 | 1 | J | 3.12 | 1 to 1.6 | 95 | 50 | neg. |
| 171 | 1 | J | 1.56 | 1.25 to 1 | 97 | 65 | neg. |
| 172 | 1 | J | 0.78 | 2.5 to 1 | 90 | 0 | neg. |
| 173 | — | K | 3.12 | — | — | 45 | — |
| 174 | — | K | 1.56 | — | — | 0 | — |
| 175 | — | K | 0.78 | — | — | 0 | — |
| 176 | 1 | K | 3.12 | 1 to 1.6 | 95 | 45 | neg. |
| 177 | 1 | K | 1.56 | 1.25 to 1 | 93 | 25 | neg. |
| 178 | 1 | K | 0.78 | 2.5 to 1 | 95 | 45 | neg. |

Compound E = 4,4,4-trichloro-2-(3,5-dichlorophenyl)-2-hydroxybutyl-1-(4-methylphenyl)sulfonate
Compound I = 4,4,4-trichloro-2-(3,5-dichlorophenyl)-2-hydroxybutyl-1-(3-trifluoromethylphenyl)sulfonate
Compound J = 4,4,4-trichloro-2-(3,5-dichlorophenyl)-2-hydroxybutyl-1-(4-chlorophenyl)sulfonate
Compound K = 4,4,4-trichloro-2-(3,5-dichlorophenyl)-2-hydroxybutyl-1-(2,4,6-trimethylphenyl)sulfonate

TABLE 10

Control of Giant Foxtail
(14 day evaluation)

| Run Number | Atrazine Dosage lb/acre | Glycol Sulfonate Compound | Sulfonate Dosage, lb mol/acre × 1000 | Approx. Wt. Ratio, Atrazine to Sulfonate | Expected Control % | Actual Control % | Percent Increase Over Expected Control |
|---|---|---|---|---|---|---|---|
| 179 | 1 | — | — | — | — | 75 | — |
| 180 | — | E | 3.12 | — | — | 20 | — |
| 181 | — | E | 1.56 | — | — | 0 | — |
| 182 | — | E | 0.78 | — | — | 0 | — |
| 183 | 1 | E | 3.12 | 1 to 1.6 | 80 | 90 | 13 |
| 184 | 1 | E | 1.56 | 1.25 to 1 | 75 | 90 | 20 |
| 185 | 1 | E | 0.78 | 2.5 to 1 | 75 | 95 | 27 |
| 186 | — | I | 3.12 | — | — | 10 | — |
| 187 | — | I | 1.56 | — | — | 0 | — |
| 188 | — | I | 0.78 | — | — | 0 | — |
| 189 | 1 | I | 3.12 | 1 to 1.6 | 78 | 95 | 22 |
| 190 | 1 | I | 1.56 | 1.25 to 1 | 75 | 85 | 13 |
| 191 | 1 | I | 0.78 | 2.5 to 1 | 75 | 40 | neg. |
| 192 | — | J | 3.12 | — | — | 15 | — |
| 193 | — | J | 1.56 | — | — | 0 | — |
| 194 | — | J | 0.78 | — | — | 0 | — |
| 195 | 1 | J | 3.12 | 1 to 1.6 | 79 | 100 | 27 |
| 196 | 1 | J | 1.56 | 1.25 to 1 | 75 | 60 | neg. |
| 197 | 1 | J | 0.78 | 2.5 to 1 | 75 | 70 | neg. |
| 198 | — | K | 3.12 | — | — | 10 | — |
| 199 | — | K | 1.56 | — | — | 0 | — |
| 200 | — | K | 0.78 | — | — | 0 | — |
| 201 | 1 | K | 3.12 | 1 to 1.6 | 78 | 90 | 15 |
| 202 | 1 | K | 1.56 | 1.25 to 1 | 75 | 85 | 13 |
| 203 | 1 | K | 0.78 | 2.5 to 1 | 75 | 40 | neg. |

Compound E = 4,4,4-trichloro-2-(3,5-dichlorophenyl)-2-hydroxybutyl-1-(4-methylphenyl)sulfonate
Compound I = 4,4,4-trichloro-2-(3,5-dichlorophenyl)-2-hydroxybutyl-1-(3-trifluoromethylphenyl)sulfonate
Compound J = 4,4,4-trichloro-2-(3,5-dichlorophenyl)-2-hydroxybutyl-1-(4-chlorophenyl)sulfonate
Compound K = 4,4,4-trichloro-2-(3,5-dichlorophenyl)-2-hydroxybutyl-1-(2,4,6-trimethylphenyl)sulfonate

EXAMPLE 10

Additional testing was carried out in a manner similar to that used in Example 9 except that (a) all spray compositions contained sufficient crop oil concentrate to provide 1 quart/acre crop oil, and (b) all atrazine-containing compositions contained 0.3 percent atrazine to provide 0.75 lb/acre of that active ingredient. The compositions were sprayed on giant foxtail seedlings which were at the 4 leaf stage and 3 inches tall.

The extent of control was determined after 8 days and 14 days respectively. The results after 8 days are tabulated in Table 11 while the results after 14 days are tabulated in Table 12.

In both tables, the enhancement over the results with atrazine alone are tabulated and shown.

TABLE 11

Control of Giant Foxtail
(Evaluation After 8 Days)

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 204 | 0.75 | — | — | — | 44 | — |
| 205 | — | E | 3.12 | — | 10 | — |
| 206 | — | E | 1.56 | — | 0 | — |
| 207 | — | E | 0.78 | — | 0 | — |
| 208 | — | E | 0.39 | — | 0 | — |
| 209 | 0.75 | E | 3.12 | 1 to 2 | 85 | 93 |
| 210 | 0.75 | E | 1.56 | 1 to 1 | 90 | 105 |
| 211 | 0.75 | E | 0.78 | 2 to 1 | 65 | 48 |
| 212 | 0.75 | E | 0.39 | 4 to 1 | 45 | 11 |
| 213 | — | L | 3.12 | — | 0 | — |
| 214 | — | L | 1.56 | — | 0 | — |
| 215 | — | L | 0.78 | — | 0 | — |
| 216 | — | L | 0.39 | — | 0 | — |
| 217 | 0.75 | L | 3.12 | 1 to 2 | 65 | 48 |
| 218 | 0.75 | L | 1.56 | 1 to 1 | 50 | 14 |
| 219 | 0.75 | L | 0.78 | 2 to 1 | 65 | 48 |
| 220 | 0.75 | L | 0.39 | 4 to 1 | 75 | 70 |
| 221 | — | M | 3.12 | — | 10 | — |
| 222 | — | M | 1.56 | — | 0 | — |
| 223 | — | M | 0.78 | — | 0 | — |
| 224 | — | M | 0.39 | — | 0 | — |
| 225 | 0.75 | M | 3.12 | 1 to 2 | 90 | 105 |
| 226 | 0.75 | M | 1.56 | 1 to 1 | 95 | 116 |
| 227 | 0.75 | M | 0.78 | 2 to 1 | 75 | 70 |

TABLE 11-continued

Control of Giant Foxtail
(Evaluation After 8 Days)

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 228 | 0.75 | M | 0.39 | 4 to 1 | 65 | 48 |
| 229 | — | N | 3.12 | — | 10 | — |
| 230 | — | N | 1.56 | — | 0 | — |
| 231 | — | N | 0.78 | — | 0 | — |
| 232 | — | N | 0.39 | — | 0 | — |
| 233 | 0.75 | N | 3.12 | 1 to 2 | 70 | 59 |
| 234 | 0.75 | N | 1.56 | 1 to 1 | 70 | 59 |
| 235 | 0.75 | N | 0.78 | 2 to 1 | 45 | 2 |
| 236 | 0.75 | N | 0.39 | 4 to 1 | 60 | 36 |

Compound E = 4,4,4-trichloro-2-(3,5-dichlorophenyl)-2-hydroxybutyl-1-(4-methylphenyl)-sulfonate
Compound L = 4,4,4-trichloro-2-(3,5-dichlorophenyl)-2-hydroxybutyl-1-(2,4,6-tri(1-methyl-ethyl)phenyl)sulfonate
Compound M = 4,4,4-trichloro-2 (3,5-dichlorophenyl)-2-hydroxybutyl-1-(2,5-dichlorophenyl)-sulfonate
Compound N = 4,4,4-trichloro-2-(3,5-dichlorophenyl)-2-hydroxybutyl-1-(4-methoxyphenyl)-sulfonate

TABLE 12

Control of Giant Foxtail
(Evaluation After 14 Days)

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 237 | 0.75 | — | — | — | 34 | — |
| 238 | — | E | 3.12 | 1 to 2 | 0 | — |
| 239 | — | E | 1.56 | 1 to 1 | 0 | — |
| 240 | — | E | 0.78 | 2 to 1 | 0 | — |
| 241 | — | E | 0.39 | 4 to 1 | 0 | — |
| 242 | 0.75 | E | 3.12 | 1 to 2 | 98 | 188 |
| 243 | 0.75 | E | 1.56 | 1 to 1 | 98 | 188 |
| 244 | 0.75 | E | 0.78 | 2 to 1 | — | — |
| 245 | 0.75 | E | 0.39 | 4 to 1 | 65 | 91 |
| 246 | — | L | 3.12 | — | 0 | — |
| 247 | — | L | 1.56 | — | 0 | — |
| 248 | — | L | 0.78 | — | 0 | — |
| 249 | — | L | 0.39 | — | 0 | — |
| 250 | 0.75 | L | 3.12 | 1 to 2 | 65 | 91 |
| 251 | 0.75 | L | 1.56 | 1 to 1 | 45 | 32 |
| 252 | 0.75 | L | 0.78 | 2 to 1 | 80 | 135 |
| 253 | 0.75 | L | 0.39 | 4 to 1 | 73 | 115 |
| 254 | — | M | 3.12 | — | 0 | — |
| 255 | — | M | 1.56 | — | 0 | — |
| 256 | — | M | 0.78 | — | 0 | — |
| 257 | — | M | 0.39 | — | 0 | — |
| 258 | 0.75 | M | 3.12 | 1 to 2 | 100 | 194 |
| 259 | 0.75 | M | 1.56 | 1 to 1 | 98 | 188 |
| 260 | 0.75 | M | 0.78 | 2 to 1 | 95 | 179 |
| 261 | 0.75 | M | 0.39 | 4 to 1 | 65 | 91 |
| 262 | — | N | 3.12 | — | 0 | — |
| 263 | — | N | 1.56 | — | 0 | — |
| 264 | — | N | 0.78 | — | 0 | — |
| 265 | — | N | 0.39 | — | 0 | — |
| 266 | 0.75 | N | 3.12 | 1 to 2 | 65 | 91 |
| 267 | 0.75 | N | 1.56 | 1 to 1 | 85 | 150 |
| 268 | 0.75 | N | 0.78 | 2 to 1 | 85 | 150 |
| 269 | 0.75 | N | 0.39 | 4 to 1 | 78 | 121 |

See footnote to Table 11 for identification of compounds.

EXAMPLE 11

A number of different glycol sulfonates were made up into emulsion concentrates in a manner similar to that described in Example 6 except that a glycol ether solver was added to the solvent mixture employed.

Also, all atrazine containing compositions were made up to contain 0.3 percent by weight atrazine and provide 0.75 lb/acre atrazine when applied to the test plants.

The test plants were giant foxtail seedlings at the 4 leaf stage and 2½ to 3 inches tall.

Application was made as in Example 6 except that none of the glycol sulfonate compounds were applied except in combination with atrazine.

The extent of control of the giant foxtail was determined after 3 days and again after 6 days, and still further, after 15 days. The results are tabulated in Tables 13, 14 and 15, respectively. The compounds tested are identified in the footnote to Table 13.

In each of the tables, the enhancement over the results with atrazine alone are tabulated and shown.

TABLE 13

Control of Giant Foxtail (Evaluation After 3 Days)

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 270 | 0.75 | — | — | — | 7 | — |
| 271 | 0.75 | O | 1.56 | 1 to 1 | 45 | 540 |
| 272 | 0.75 | O | 0.78 | 2 to 1 | 30 | 330 |
| 273 | 0.75 | O | 0.39 | 4 to 1 | 15 | 114 |
| 274 | 0.75 | O | 0.20 | 8 to 1 | 10 | 43 |
| 275 | 0.75 | P | 1.56 | 1 to 1 | 40 | 470 |
| 276 | 0.75 | P | 0.78 | 2 to 1 | 35 | 400 |
| 277 | 0.75 | P | 0.39 | 4 to 1 | 15 | 114 |
| 278 | 0.75 | P | 0.20 | 8 to 1 | 10 | 43 |
| 279 | 0.75 | Q | 1.56 | 1 to 1 | 40 | 470 |
| 280 | 0.75 | Q | 0.78 | 2 to 1 | 30 | 330 |
| 281 | 0.75 | Q | 0.39 | 4 to 1 | 20 | 185 |
| 294 | 0.75 | T | 0.20 | 8 to 1 | 5 | ~0 |
| 295 | 0.75 | J | 1.56 | 1 to 1 | 25 | 260 |
| 296 | 0.75 | J | 0.78 | 2 to 1 | 20 | 185 |
| 297 | 0.75 | J | 0.39 | 4 to 1 | 10 | 43 |
| 298 | 0.75 | J | 0.20 | 8 to 1 | 5 | ∞0 |
| 299 | 0.75 | K | 1.56 | 1 to 1 | 30 | 330 |
| 300 | 0.75 | K | 0.78 | 2 to 1 | 35 | 400 |
| 301 | 0.75 | K | 0.39 | 4 to 1 | 10 | 43 |
| 302 | 0.75 | K | 0.20 | 8 to 1 | 5 | ~0 |
| 303 | 0.75 | A | 1.56 | 1 to 1 | 40 | 470 |
| 304 | 0.75 | A | 0.78 | 2 to 1 | 25 | 260 |
| 305 | 0.75 | A | 0.39 | 4 to 1 | 20 | 185 |
| 306 | 0.75 | A | 0.20 | 8 to 1 | 10 | 43 |
| 307 | 0.75 | L | 1.56 | 1 to 1 | 20 | 185 |
| 308 | 0.75 | L | 0.78 | 2 to 1 | 20 | 185 |
| 309 | 0.75 | L | 0.39 | 4 to 1 | 15 | 114 |
| 310 | 0.75 | L | 0.20 | 8 to 1 | 10 | 43 |
| 311 | 0.75 | M | 1.56 | 1 to 1 | 50 | 615 |
| 312 | 0.75 | M | 0.78 | 2 to 1 | 35 | 400 |
| 313 | 0.75 | M | 0.39 | 4 to 1 | 20 | 185 |
| 314 | 0.75 | M | 0.20 | 8 to 1 | 5 | ~0 |
| 315 | 0.75 | N | 1.56 | 1 to 1 | 35 | 400 |
| 316 | 0.75 | N | 0.78 | 2 to 1 | 35 | 400 |
| 317 | 0.75 | N | 0.39 | 4 to 1 | 30 | 330 |
| 318 | 0.75 | N | 0.20 | 8 to 1 | 20 | 185 |
| 319 | 0.75 | E | 1.56 | 1 to 1 | 30 | 330 |
| 320 | 0.75 | E | 0.78 | 2 to 1 | 35 | 400 |
| 321 | 0.75 | E | 0.39 | 4 to 1 | 20 | 185 |
| 322 | 0.75 | E | 0.20 | 8 to 1 | 25 | 260 |
| 323 | 0.75 | C | 1.56 | 1 to 1 | 40 | 470 |
| 324 | 0.75 | C | 0.78 | 2 to 1 | 40 | 470 |
| 325 | 0.75 | C | 0.39 | 4 to 1 | 20 | 185 |
| 326 | 0.75 | C | 0.20 | 8 to 1 | 15 | 114 |
| 327 | 0.75 | G | 1.56 | 1 to 1 | 40 | 470 |
| 328 | 0.75 | G | 0.78 | 2 to 1 | 20 | 185 |
| 329 | 0.75 | G | 0.39 | 4 to 1 | 15 | 114 |
| 330 | 0.75 | G | 0.20 | 8 to 1 | 5 | ~0 |

Compound O = 4,4,4-trichloro-2-(3,5-dichlorophenyl)-2-hydroxybutyl-1-phenylsulfonate
Compound P = 4,4,4-trichloro-2-(3,5-dichlorophenyl)-2-hydroxybutyl-1-(2,5-dimethylphenyl)sulfonate
Compound Q = 4,4,4-trichloro-2-(3,5-dichlorophenyl)-2-hydroxybutyl-1-(3,4-dichlorophenyl)sulfonate
Compound R = 4,4,4-trichloro-2-(3,5-dichlorophenyl)-2-hydroxybutyl-1-(3,4-dimethylphenyl)sulfonate
Compound S = 4,4,4-trichloro-2-(3,5-dichlorophenyl)-2-hydroxybutyl-1-n-butylsulfonate
Compound T = 4,4,4-trichloro-2-(3,5-dichlorophenyl)-2-hydroxybutyl-1-(2,4-dimethylphenyl)sulfonate
Compound J = 4,4,4-trichloro-2-(3,5-dichlorophenyl)-2-hydroxybutyl-1-(4-chlorophenyl)sulfonate
Compound K = 4,4,4-trichloro-2-(3,5-dichlorophenyl)-2-hydroxybutyl-1-(2,4,6-trimethylphenyl)sulfonate
Compound A = 4,4,4-trichloro-2-(3,5-dichlorophenyl)-2-hydroxybutyl-1-methylsulfonate
Compound L = 4,4,4-trichloro-2-(3,5-dichlorophenyl)-2-hydroxybutyl-1-(2,4,6-tri(1-methylethyl)phenyl)sulfonate
Compound M = 4,4,4-trichloro-2-(3,5-dichlorophenyl)-2-hydroxybutyl-1-(2,5-dichlorophenyl)sulfonate
Compound N = 4,4,4-trichloro-2-(3,5-dichlorophenyl)-2-hydroxybutyl-1-(4-methoxyphenyl)sulfonate
Compound E = 4,4,4-trichloro-2-(3,5-dichlorophenyl)-2-hydroxybutyl-1-(4-methylphenyl)sulfonate
Compound C = 4,4,4-trichloro-2-(3,5-dichlorophenyl)-2-hydroxybutyl-1-(1-methylethyl)sulfonate
Compound G = 4,4,4-trichloro-2-(3,5-dichlorophenyl)-2-hydroxybutyl-1-chloromethylsulfonate

TABLE 14

Control of Giant Foxtail (Evaluation After 6 Days)

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 331 | 0.75 | — | — | — | 24 | — |

TABLE 14-continued

Control of Giant Foxtail
(Evaluation After 6 Days)

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 332 | 0.75 | O | 1.56 | 1 to 1 | 90 | 275 |
| 333 | 0.75 | O | 0.78 | 2 to 1 | 75 | 210 |
| 334 | 0.75 | O | 0.39 | 4 to 1 | 65 | 170 |
| 335 | 0.75 | O | 0.20 | 8 to 1 | 70 | 190 |
| 336 | 0.75 | P | 1.56 | 1 to 1 | 85 | 255 |
| 337 | 0.75 | P | 0.78 | 2 to 1 | 80 | 230 |
| 338 | 0.75 | P | 0.39 | 4 to 1 | 55 | 130 |
| 339 | 0.75 | P | 0.20 | 8 to 1 | 35 | 46 |
| 340 | 0.75 | Q | 1.56 | 1 to 1 | 85 | 255 |
| 341 | 0.75 | Q | 0.78 | 2 to 1 | 85 | 255 |
| 342 | 0.75 | Q | 0.39 | 4 to 1 | 80 | 230 |
| 343 | 0.75 | Q | 0.20 | 8 to 1 | 50 | 110 |
| 344 | 0.75 | R | 1.56 | 1 to 1 | 70 | 190 |
| 345 | 0.75 | R | 0.78 | 2 to 1 | 50 | 110 |
| 346 | 0.75 | R | 0.39 | 4 to 1 | 75 | 210 |
| 347 | 0.75 | R | 0.20 | 8 to 1 | 55 | 130 |
| 348 | 0.75 | S | 1.56 | 1 to 1 | 60 | 150 |
| 349 | 0.75 | S | 0.78 | 2 to 1 | 70 | 190 |
| 350 | 0.75 | S | 0.39 | 4 to 1 | 75 | 210 |
| 351 | 0.75 | S | 0.20 | 8 to 1 | 60 | 150 |
| 352 | 0.75 | T | 1.56 | 1 to 1 | 70 | 190 |
| 353 | 0.75 | T | 0.78 | 2 to 1 | 55 | 130 |
| 354 | 0.75 | T | 0.39 | 4 to 1 | 70 | 190 |
| 355 | 0.75 | T | 0.20 | 8 to 1 | 45 | 88 |
| 356 | 0.75 | J | 1.56 | 1 to 1 | 80 | 230 |
| 357 | 0.75 | J | 0.78 | 2 to 1 | 70 | 190 |
| 358 | 0.75 | J | 0.39 | 4 to 1 | 75 | 210 |
| 359 | 0.75 | J | 0.20 | 8 to 1 | 60 | 150 |
| 360 | 0.75 | K | 1.56 | 1 to 1 | 60 | 150 |
| 361 | 0.75 | K | 0.78 | 2 to 1 | 90 | 275 |
| 362 | 0.75 | K | 0.39 | 4 to 1 | 60 | 150 |
| 363 | 0.75 | K | 0.20 | 8 to 1 | 40 | 67 |
| 364 | 0.75 | A | 1.56 | 1 to 1 | 60 | 150 |
| 365 | 0.75 | A | 0.78 | 2 to 1 | 55 | 130 |
| 366 | 0.75 | A | 0.39 | 4 to 1 | 70 | 190 |
| 367 | 0.75 | A | 0.20 | 8 to 1 | 65 | 170 |
| 368 | 0.75 | L | 1.56 | 1 to 1 | 40 | 67 |
| 369 | 0.75 | L | 0.78 | 2 to 1 | 40 | 67 |
| 370 | 0.75 | L | 0.39 | 4 to 1 | 40 | 67 |
| 371 | 0.75 | L | 0.20 | 8 to 1 | 45 | 88 |
| 372 | 0.75 | M | 1.56 | 1 to 1 | 90 | 275 |
| 373 | 0.75 | M | 0.78 | 2 to 1 | 80 | 230 |
| 374 | 0.75 | M | 0.39 | 4 to 1 | 80 | 230 |
| 375 | 0.75 | M | 0.20 | 8 to 1 | 45 | 88 |
| 376 | 0.75 | N | 1.56 | 1 to 1 | 55 | 130 |
| 377 | 0.75 | N | 0.78 | 2 to 1 | 50 | 110 |
| 378 | 0.75 | N | 0.39 | 4 to 1 | 80 | 230 |
| 379 | 0.75 | N | 0.20 | 8 to 1 | 70 | 190 |
| 380 | 0.75 | E | 1.56 | 1 to 1 | 55 | 130 |
| 381 | 0.75 | E | 0.78 | 2 to 1 | 60 | 150 |
| 382 | 0.75 | E | 0.39 | 4 to 1 | 55 | 130 |
| 383 | 0.75 | E | 0.20 | 8 to 1 | 70 | 190 |
| 384 | 0.75 | C | 1.56 | 1 to 1 | 65 | 170 |
| 385 | 0.75 | C | 0.78 | 2 to 1 | 55 | 130 |
| 386 | 0.75 | C | 0.39 | 4 to 1 | 45 | 88 |
| 387 | 0.75 | C | 0.20 | 8 to 1 | 70 | 190 |
| 388 | 0.75 | G | 1.56 | 1 to 1 | 75 | 210 |
| 389 | 0.75 | G | 0.78 | 2 to 1 | 50 | 110 |
| 390 | 0.75 | G | 0.39 | 4 to 1 | 45 | 88 |
| 391 | 0.75 | G | 0.20 | 8 to 1 | 50 | 110 |

See footnote to Table 13 for identification of compounds.

TABLE 15

Control of Giant Foxtail (Evaluation After 15 Days)

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 392 | 0.75 | — | — | — | 10 | — |
| 393 | 0.75 | O | 1.56 | 1 to 1 | 90 | 800 |
| 394 | 0.75 | O | 0.78 | 2 to 1 | 55 | 450 |

TABLE 15-continued

Control of Giant Foxtail (Evaluation After 15 Days)

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 395 | 0.75 | O | 0.39 | 4 to 1 | 55 | 450 |
| 396 | 0.75 | O | 0.20 | 8 to 1 | 50 | 400 |
| 397 | 0.75 | P | 1.56 | 1 to 1 | 70 | 600 |
| 398 | 0.75 | P | 0.78 | 2 to 1 | 65 | 550 |
| 399 | 0.75 | P | 0.39 | 4 to 1 | 50 | 400 |
| 400 | 0.75 | P | 0.20 | 8 to 1 | 55 | 450 |
| 401 | 0.75 | Q | 1.56 | 1 to 1 | 75 | 650 |
| 402 | 0.75 | Q | 0.78 | 2 to 1 | 70 | 600 |
| 403 | 0.75 | Q | 0.39 | 4 to 1 | 50 | 400 |
| 404 | 0.75 | Q | 0.20 | 8 to 1 | 30 | 200 |
| 405 | 0.75 | R | 1.56 | 1 to 1 | 55 | 450 |
| 406 | 0.75 | R | 0.78 | 2 to 1 | 30 | 200 |
| 407 | 0.75 | R | 0.39 | 4 to 1 | 65 | 550 |
| 408 | 0.75 | R | 0.20 | 8 to 1 | 20 | 100 |
| 409 | 0.75 | S | 1.56 | 1 to 1 | 50 | 400 |
| 410 | 0.75 | S | 0.78 | 2 to 1 | 60 | 500 |
| 411 | 0.75 | S | 0.39 | 4 to 1 | 35 | 250 |
| 412 | 0.75 | S | 0.20 | 8 to 1 | 35 | 250 |
| 413 | 0.75 | T | 1.56 | 1 to 1 | 55 | 450 |
| 414 | 0.75 | T | 0.78 | 2 to 1 | 40 | 300 |
| 415 | 0.75 | T | 0.39 | 4 to 1 | 30 | 200 |
| 416 | 0.75 | T | 0.20 | 8 to 1 | 20 | 100 |
| 417 | 0.75 | J | 1.56 | 1 to 1 | 50 | 400 |
| 418 | 0.75 | J | 0.78 | 2 to 1 | 60 | 500 |
| 419 | 0.75 | J | 0.39 | 4 to 1 | 55 | 450 |
| 420 | 0.75 | J | 0.20 | 8 to 1 | 20 | 100 |
| 421 | 0.75 | K | 1.56 | 1 to 1 | 40 | 300 |
| 422 | 0.75 | K | 0.78 | 2 to 1 | 80 | 700 |
| 423 | 0.75 | K | 0.39 | 4 to 1 | 40 | 300 |
| 424 | 0.75 | K | 0.20 | 8 to 1 | 30 | 200 |
| 425 | 0.75 | A | 1.56 | 1 to 1 | 40 | 300 |
| 426 | 0.75 | A | 0.78 | 2 to 1 | 50 | 400 |
| 427 | 0.75 | A | 0.39 | 4 to 1 | 50 | 400 |
| 428 | 0.75 | A | 0.20 | 8 to 1 | 65 | 550 |
| 429 | 0.75 | L | 1.56 | 1 to 1 | 30 | 200 |
| 430 | 0.75 | L | 0.78 | 2 to 1 | 45 | 350 |
| 431 | 0.75 | L | 0.39 | 4 to 1 | 25 | 150 |
| 432 | 0.75 | L | 0.20 | 8 to 1 | 30 | 200 |
| 433 | 0.75 | M | 1.56 | 1 to 1 | 98 | 880 |
| 434 | 0.75 | M | 0.78 | 2 to 1 | 95 | 850 |
| 435 | 0.75 | M | 0.39 | 4 to 1 | 95 | 850 |
| 436 | 0.75 | M | 0.20 | 8 to 1 | 25 | 150 |
| 437 | 0.75 | N | 1.56 | 1 to 1 | 45 | 350 |
| 438 | 0.75 | N | 0.78 | 2 to 1 | 40 | 300 |
| 439 | 0.75 | N | 0.39 | 4 to 1 | 80 | 700 |
| 440 | 0.75 | N | 0.20 | 8 to 1 | 50 | 400 |
| 441 | 0.75 | E | 1.56 | 1 to 1 | 40 | 300 |
| 442 | 0.75 | E | 0.78 | 2 to 1 | 55 | 450 |
| 443 | 0.75 | E | 0.39 | 4 to 1 | 40 | 300 |
| 444 | 0.75 | E | 0.20 | 8 to 1 | 70 | 600 |
| 445 | 0.75 | C | 1.56 | 1 to 1 | 70 | 600 |
| 446 | 0.75 | C | 0.78 | 2 to 1 | 60 | 500 |
| 447 | 0.75 | C | 0.39 | 4 to 1 | 40 | 300 |
| 448 | 0.75 | C | 0.20 | 8 to 1 | 70 | 600 |
| 449 | 0.75 | G | 1.56 | 1 to 1 | 75 | 650 |
| 450 | 0.75 | G | 0.78 | 2 to 1 | 40 | 300 |
| 451 | 0.75 | G | 0.39 | 4 to 1 | 40 | 300 |
| 452 | 0.75 | G | 0.20 | 8 to 1 | 50 | 400 |

See footnote to Table 13 for identification of compounds.

EXAMPLE 12

Two of the glycol sulfonates previously tested were again made up and tested in a manner similar to that of Example 7 except that all atrazine spray compositions contained 0.6 percent by weight atrazine providing 1.5 lb/acre when sprayed, the glycol sulfonates were tested only in combination with atrazine, and the test plants were giant foxtail and maize (corn) tested side by side.

The giant foxtail seedlings were 5 to 6 inches tall and at the 4 to 4½ leaf stage while the maize seedlings were 7 to 11 inches tall and at the 4 leaf stage.

The extent of control of the test plants was determined 13 days after treatment and the results are tabulated in Table 16.

TABLE 16

Control of Giant Foxtail in Presence of Corn

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone | Control of Corn |
|---|---|---|---|---|---|---|---|
| 453 | 1.5 | — | — | — | 33 | — | 0 |
| 454 | 1.5 | E | 2.34 | 1.25 to 1 | 100 | 200 | 20 |
| 455 | 1.5 | E | 1.17 | 2.5 to 1 | 100 | 200 | 0 |
| 456 | 1.5 | E | 0.59 | 5 to 1 | 100 | 200 | 0 |
| 457 | 1.5 | M | 2.34 | 1.25 to 1 | 100 | 200 | 0 |
| 458 | 1.5 | M | 1.17 | 2.5 to 1 | 98 | 195 | 0 |
| 459 | 1.5 | M | 0.59 | 5 to 1 | 100 | 200 | 0 |

Compound E = 4,4,4-trichloro-2-(3,5-dichlorophenyl)-2-hydroxybutyl-1-(4-methylphenyl)sulfonate
Compound M = 4,4,4-trichloro-2-(3,5-dichlorophenyl)-2-hydroxybutyl-1-(2,5-dichlorophenyl)sulfonate

EXAMPLE 13

The same two glycol sulfonates employed in Example 12 were again used in tests carried out in a manner similar to that used in Example 7, except that in some runs the soil was shielded with vermiculite during spraying of the test plants while in other tests upon the same plant species using the same glycol sulfonates soil shielding was omitted to demonstrate the effect of root uptake of the atrazine.

Additionally, some atrazine containing spray compositions contained 0.6 percent atrazine while others contained 0.4 percent atrazine.

The glycol sulfonates were tested only in combination with atrazine. A compatibility agent was added to the combinations to bring the atrazine component into solution.

The test plants were giant foxtail seedlings at the 3 to 3½ leaf stage, green foxtail seedlings at the 3 leaf stage, and johnsongrass seedlings at the 2 to 2½ leaf stage.

The tests upon giant foxtail plants are tabulated in Table 17; the tests upon green foxtail seedlings are tabulated in Table 18; while the tests upon johnsongrass are tabulated in Table 19.

The glycol sulfonates used are identified in the footnote to Table 16.

TABLE 17

Control of Giant Foxtail and Soil Shielding Effect

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone | Soil Shielding |
|---|---|---|---|---|---|---|---|
| 460 | 1 | — | — | — | 48 | — | Yes |
| 461 | 1 | E | 1.56 | 1.25 to 1 | 90 | 88 | Yes |
| 462 | 1 | E | 0.78 | 2.5 to 1 | 75 | 56 | Yes |
| 463 | 1 | E | 0.39 | 5 to 1 | 88 | 83 | Yes |
| 464 | 1 | M | 1.56 | 1.25 to 1 | 95 | 98 | Yes |
| 465 | 1 | M | 0.78 | 2.5 to 1 | 95 | 98 | Yes |
| 466 | 1 | M | 0.39 | 5 to 1 | 95 | 98 | Yes |
| 467 | 1 | — | — | — | 95 | — | No |
| 468 | 1 | E | 1.56 | 1.25 to 1 | 90 | ~0 | No |
| 469 | 1 | E | 0.78 | 2.5 to 1 | 100 | ~0 | No |
| 470 | 1 | E | 0.39 | 5 to 1 | 95 | ~0 | No |
| 471 | 1 | M | 1.56 | 1.25 to 1 | 100 | 5 | No |
| 472 | 1 | M | 0.78 | 2.5 to 1 | 100 | 5 | No |
| 473 | 1 | M | 0.39 | 5 to 1 | 100 | 5 | No |
| 474 | 1.5 | — | — | — | 47 | — | Yes |
| 475 | 1.5 | E | 1.56 | 1.25 to 1 | 100 | 113 | Yes |
| 476 | 1.5 | E | 0.78 | 2.5 to 1 | 100 | 113 | Yes |
| 477 | 1.5 | E | 0.39 | 5 to 1 | 100 | 113 | Yes |
| 478 | 1.5 | M | 1.56 | 1.25 to 1 | 90 | 91 | Yes |
| 479 | 1.5 | M | 0.78 | 2.5 to 1 | 95 | 102 | Yes |
| 480 | 1.5 | M | 0.39 | 5 to 1 | 95 | 102 | Yes |

See footnote to Table 16 for identification of compounds.

TABLE 18

Control of Green Foxtail and Soil Shielding Effect

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone | Soil Shielding |
|---|---|---|---|---|---|---|---|
| 481 | 1 | — | — | — | 89 | — | Yes |
| 482 | 1 | E | 1.56 | 1.25 to 1 | 85 | ~0 | Yes |
| 483 | 1 | E | 0.78 | 2.5 to 1 | 85 | ~0 | Yes |
| 484 | 1 | E | 0.39 | 5 to 1 | 65 | neg. | Yes |
| 485 | 1 | M | 1.56 | 1.25 to 1 | 95 | 7 | Yes |
| 486 | 1 | M | 0.78 | 2.5 to 1 | 100 | 12 | Yes |
| 487 | 1 | M | 0.39 | 5 to 1 | 90 | ~0 | Yes |

TABLE 18-continued

Control of Green Foxtail and Soil Shielding Effect

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone | Soil Shielding |
| --- | --- | --- | --- | --- | --- | --- | --- |
| 488 | 1 | — | — | — | 100 | — | No |
| 489 | 1 | E | 1.56 | 1.25 to 1 | 100 | 0 | No |
| 490 | 1 | E | 0.78 | 2.5 to 1 | 100 | 0 | No |
| 491 | 1 | E | 0.39 | 5 to 1 | 100 | 0 | No |
| 492 | 1 | M | 1.56 | 1.25 to 1 | 100 | 0 | No |
| 493 | 1 | M | 0.78 | 2.5 to 1 | 100 | 0 | No |
| 494 | 1 | M | 0.39 | 5 to 1 | 100 | 0 | No |
| 495 | 1.5 | — | — | — | 87 | — | Yes |
| 496 | 1.5 | E | 1.56 | 1.25 to 1 | 100 | 15 | Yes |
| 497 | 1.5 | E | 0.78 | 2.5 to 1 | 100 | 15 | Yes |
| 498 | 1.5 | E | 0.39 | 5 to 1 | 100 | 15 | Yes |
| 499 | 1.5 | M | 1.56 | 1.25 to 1 | 100 | 15 | Yes |
| 500 | 1.5 | M | 0.78 | 2.5 to 1 | 100 | 15 | Yes |
| 501 | 1.5 | M | 0.39 | 5 to 1 | 100 | 15 | Yes |

See footnote to Table 16 for identification of compounds.

TABLE 19

Control of Johnsongrass and Soil Shielding Effect

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone | Soil Shielding |
| --- | --- | --- | --- | --- | --- | --- | --- |
| 502 | 1 | — | — | — | 13 | — | Yes |
| 503 | 1 | E | 1.56 | 1.25 to 1 | 30 | 130 | Yes |
| 504 | 1 | E | 0.78 | 2.5 to 1 | 30 | 130 | Yes |
| 505 | 1 | E | 0.39 | 5 to 1 | 30 | 130 | Yes |
| 506 | 1 | M | 1.56 | 1.25 to 1 | 75 | 475 | Yes |
| 507 | 1 | M | 0.78 | 2.5 to 1 | 60 | 360 | Yes |
| 508 | 1 | M | 0.39 | 5 to 1 | 35 | 170 | Yes |
| 509 | 1 | — | — | — | 10 | — | No |
| 510 | 1 | E | 1.56 | 1.25 to 1 | 100 | 900 | No |
| 511 | 1 | E | 0.78 | 2.5 to 1 | 100 | 900 | No |
| 512 | 1 | E | 0.39 | 5 to 1 | 100 | 900 | No |
| 513 | 1 | M | 1.56 | 1.25 to 1 | 100 | 900 | No |
| 514 | 1 | M | 0.78 | 2.5 to 1 | 100 | 900 | No |
| 515 | 1 | M | 0.39 | 5 to 1 | 100 | 900 | No |
| 516 | 1.5 | — | — | — | 10 | — | Yes |
| 517 | 1.5 | E | 1.56 | 1.25 to 1 | 90 | 800 | Yes |
| 518 | 1.5 | E | 0.78 | 2.5 to 1 | 75 | 650 | Yes |
| 519 | 1.5 | E | 0.39 | 5 to 1 | 70 | 600 | Yes |
| 520 | 1.5 | M | 1.56 | 1.25 to 1 | 98 | 880 | Yes |
| 521 | 1.5 | M | 0.78 | 2.5 to 1 | 50 | 400 | Yes |
| 522 | 1.5 | M | 0.39 | 5 to 1 | 55 | 450 | Yes |

See footnote to Table 16 for identification of compounds.

EXAMPLE 14

Additional glycol sulfonates were made up and tested in a manner similar to that described in Example 7 except that the glycol sulfonates were tested only in combination with atrazine, atrazine was applied at the rate of 1.25 lb/acre in all applications, and the plant species were morningglory at the 1½ leaf stage, velvet leaf at the 1½ leaf stage, johnsongrass at the 2 leaf stage and giant foxtail at the leaf stage.

The extent of weed control was ascertained after 2 days and after 9 days.

The morningglory plants were 100% controlled in all tests of atrazine alone or in combination with glycol sulfonates. The johnsongrass was controlled only to the extent of 10% by atrazine after 2 days and no control was evident after 9 days. The glycol sulfonate-triazine combinations, except for compound E which provided 10 to 50% control, evidenced almost no control after either 2 days or 9 days.

The results for control of velvet leaf after 9 days are tabulated in Table 20, while the results upon giant foxtail after 9 days are tabulated in Table 21.

TABLE 20

Control of Velvet Leaf (Evaluation After 9 Days)

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
| --- | --- | --- | --- | --- | --- | --- |
| 577 | 1.25 | — | — | — | 50 | — |
| 578 | 1.25 | E | 1.56 | 1.5 to 1 | 100 | 100 |

TABLE 20-continued

Control of Velvet Leaf (Evaluation After 9 Days)

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 579 | 1.25 | E | 0.78 | 3 to 1 | 99 | 98 |
| 580 | 1.25 | E | 0.39 | 6 to 1 | 97 | 94 |
| 581 | 1.25 | M | 1.56 | 1.5 to 1 | 40 | neg. |
| 582 | 1.25 | M | 0.78 | 3 to 1 | 70 | 40 |
| 583 | 1.25 | M | 0.39 | 6 to 1 | 45 | neg. |
| 584 | 1.25 | T | 1.56 | 1.5 to 1 | 98 | 96 |
| 585 | 1.25 | T | 0.78 | 3 to 1 | 69 | 38 |
| 586 | 1.25 | T | 0.39 | 6 to 1 | 74 | 48 |
| 587 | 1.25 | A | 1.56 | 1.5 to 1 | 90 | 80 |
| 588 | 1.25 | A | 0.78 | 3 to 1 | 90 | 80 |
| 589 | 1.25 | A | 0.39 | 6 to 1 | 90 | 80 |
| 590 | 1.25 | U | 1.56 | 1.5 to 1 | 60 | 20 |
| 591 | 1.25 | U | 0.78 | 3 to 1 | 50 | 0 |
| 592 | 1.25 | U | 0.39 | 6 to 1 | 50 | 0 |
| 593 | 1.25 | C | 1.56 | 1.5 to 1 | 99 | 98 |
| 594 | 1.25 | C | 0.78 | 3 to 1 | 99 | 98 |
| 595 | 1.25 | C | 0.39 | 6 to 1 | 100 | 100 |
| 596 | 1.25 | H* | 1.56 | 1.5 to 1 | 94 | 88 |
| 597 | 1.25 | H* | 0.78 | 3 to 1 | 88 | 76 |
| 598 | 1.25 | H* | 0.39 | 6 to 1 | 88 | 76 |

*H is a sulfamate compound. See footnote to Table 3.
Compound U = 4,4,4-trichloro-2-(3,5-dichlorophenyl)-2-acetyloxybutyl-1-(1-methylethyl)sulfonate
Other compounds are identified in Table 13.

TABLE 21

Control of Giant Foxtail (Evaluation After 9 Days)

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 599 | 1.25 | — | — | | 35 | — |
| 600 | 1.25 | E | 1.56 | 1.5 to 1 | 80 | 130 |
| 601 | 1.25 | E | 0.78 | 3 to 1 | 70 | 100 |
| 602 | 1.25 | E | 0.39 | 6 to 1 | 60 | 71 |
| 603 | 1.25 | M | 1.56 | 1.5 to 1 | 45 | 29 |
| 604 | 1.25 | M | 0.78 | 3 to 1 | 40 | 14 |
| 605 | 1.25 | M | 0.39 | 6 to 1 | 55 | 57 |
| 606 | 1.25 | T | 1.56 | 1.5 to 1 | 75 | 115 |
| 607 | 1.25 | T | 0.78 | 3 to 1 | 75 | 115 |
| 608 | 1.25 | T | 0.39 | 6 to 1 | 50 | 43 |
| 609 | 1.25 | A | 1.56 | 1.5 to 1 | 30 | neg. |
| 610 | 1.25 | A | 0.78 | 3 to 1 | 55 | 57 |
| 611 | 1.25 | A | 0.39 | 6 to 1 | 30 | neg. |
| 612 | 1.25 | U | 1.56 | 1.5 to 1 | 50 | 43 |
| 613 | 1.25 | U | 0.78 | 3 to 1 | 40 | 14 |
| 614 | 1.25 | U | 0.39 | 6 to 1 | 40 | 14 |
| 615 | 1.25 | C | 1.56 | 1.5 to 1 | 50 | 43 |
| 616 | 1.25 | C | 0.78 | 3 to 1 | 45 | 29 |
| 617 | 1.25 | C | 0.39 | 6 to 1 | 60 | 71 |
| 618 | 1.25 | H* | 1.56 | 1.5 to 1 | 85 | 143 |
| 619 | 1.25 | H* | 0.78 | 3 to 1 | 45 | 29 |
| 620 | 1.25 | H* | 0.39 | 6 to 1 | 75 | 115 |

*H is a sulfamate compound. See footnote to Table 3.
Other compounds are identified in footnotes to Tables 13 and 20.

EXAMPLE 15

Some of the glycol sulfonates previously tested and additional glycol sulfonates were made up into sprayable compositions and applied in a manner similar to that described in Example 7 except that the compounds were first admixed with crop oil concentrate rather than being made up initially as emulsion concentrates. A minute quantity of dimethylsulfoxide was added to each composition to help take up the glycol sulfonate.

In each composition containing atrazine the atrazine concentration was 0.5 percent by weight, providing 1.25 lb/acre atrazine when sprayed.

The plant species tested were giant foxtail.

Evaluations of extent control were made after 10 days and after 14 days and the results tabulated in Tables 22 and 23, respectively.

The compounds tested are tabulated in a footnote at the end of Table 22.

TABLE 22

Control of Giant Foxtail (Evaluation After 10 Days)

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 621 | 1.25 | — | — | — | 30 | — |
| 622 | 1.25 | J | 1.56 | 1.5 to 1 | 85 | 185 |
| 623 | 1.25 | J | 0.78 | 3 to 1 | 50 | 67 |
| 624 | 1.25 | J | 0.39 | 6 to 1 | 70 | 133 |
| 625 | 1.25 | I | 1.56 | 1.5 to 1 | 92 | 210 |
| 626 | 1.25 | I | 0.78 | 3 to 1 | 85 | 185 |
| 627 | 1.25 | I | 0.39 | 6 to 1 | 75 | 150 |
| 628 | 1.25 | E | 1.56 | 1.5 to 1 | 70 | 133 |
| 629 | 1.25 | E | 0.78 | 3 to 1 | 90 | 200 |
| 630 | 1.25 | E | 0.39 | 6 to 1 | 85 | 185 |
| 631 | 1.25 | V | 1.56 | 1.5 to 1 | 60 | 100 |
| 632 | 1.25 | V | 0.78 | 3 to 1 | 80 | 165 |
| 633 | 1.25 | V | 0.39 | 6 to 1 | 40 | 33 |
| 634 | 1.25 | W | 1.56 | 1.5 to 1 | 70 | 133 |
| 635 | 1.25 | W | 0.78 | 3 to 1 | 70 | 133 |
| 636 | 1.25 | W | 0.39 | 6 to 1 | 70 | 133 |
| 637 | 1.25 | X | 1.56 | 1.5 to 1 | 75 | 150 |
| 638 | 1.25 | X | 0.78 | 3 to 1 | 85 | 185 |
| 639 | 1.25 | X | 0.39 | 6 to 1 | 85 | 185 |
| 640 | 1.25 | Y | 1.56 | 1.5 to 1 | 55 | 83 |
| 641 | 1.25 | Y | 0.78 | 3 to 1 | 75 | 150 |
| 642 | 1.25 | Y | 0.39 | 6 to 1 | 45 | 50 |
| 643 | 1.25 | Z | 1.56 | 1.5 to 1 | 80 | 165 |
| 644 | 1.25 | Z | 0.78 | 3 to 1 | 50 | 67 |
| 645 | 1.25 | Z | 0.39 | 6 to 1 | 50 | 67 |
| 646 | 1.25 | AA | 1.56 | 1.5 to 1 | 90 | 200 |
| 647 | 1.25 | AA | 0.78 | 3 to 1 | 90 | 200 |
| 648 | 1.25 | AA | 0.39 | 6 to 1 | 70 | 133 |

Compound J = 4,4,4-trichloro-2-(3,5-dichlorophenyl)-2-hydroxybutyl-1-(4-chlorophenyl)sulfonate
Compound I = 4,4,4-trichloro-2-(3,5-dichlorophenyl)-2-hydroxybutyl-1-(3-(trifluoromethyl)phenyl)sulfonate
Compound E = 4,4,4-trichloro-2-(3,5-dichlorophenyl)-2-hydroxybutyl-1-(4-methylphenyl)sulfonate
Compound V = 4,4,4-trichloro-2-(3,5-dichlorophenyl)-2-hydroxybutyl-1-(4-bromophenyl)sulfonate
Compound W = 4,4,4-trichloro-2-(3,5-dichlorophenyl)-2-hydroxybutyl-1-hexadecylsulfonate
Compound X = 4,4,4-trichloro-2-(3,5-dichlorophenyl)-2-hydroxybutyl-1-(4-fluorophenyl)sulfonate
Compound Y = 4,4,4-trichloro-2-(3,5-dichlorophenyl)-2-trifluoroacetyloxybutyl-1-(4-methylphenyl)sulfonate
Compound Z = 4,4,4-trichloro-2-(3,5-dichlorophenyl)-2-propionyloxybutyl-1-(4-methylphenyl)sulfonate
Compound AA = 4,4,4-trichloro-2-(3,5-dichlorophenyl)-2-trifluoroacetyloxybutyl-1-(2,5-dichlorophenyl)sulfonate

TABLE 23

Control of Giant Foxtail (Evaluation After 14 Days)

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 649 | 1.25 | — | — | — | 20 | — |
| 650 | 1.25 | J | 1.56 | 1.5 to 1 | 70 | 250 |
| 651 | 1.25 | J | 0.78 | 3 to 1 | 30 | 50 |
| 652 | 1.25 | J | 0.39 | 6 to 1 | 40 | 100 |
| 653 | 1.25 | I | 1.56 | 1.5 to 1 | 97 | 385 |
| 654 | 1.25 | I | 0.78 | 3 to 1 | 60 | 200 |
| 655 | 1.25 | I | 0.39 | 6 to 1 | 50 | 150 |
| 656 | 1.25 | E | 1.56 | 1.5 to 1 | 65 | 225 |
| 657 | 1.25 | E | 0.78 | 3 to 1 | 95 | 375 |
| 658 | 1.25 | E | 0.39 | 6 to 1 | 75 | 275 |
| 659 | 1.25 | V | 1.56 | 1.5 to 1 | 35 | 75 |
| 660 | 1.25 | V | 0.78 | 3 to 1 | 69 | 245 |
| 661 | 1.25 | V | 0.39 | 6 to 1 | 25 | 25 |
| 662 | 1.25 | W | 1.56 | 1.5 to 1 | 65 | 225 |
| 663 | 1.25 | W | 0.78 | 3 to 1 | 75 | 275 |
| 664 | 1.25 | W | 0.39 | 6 to 1 | 50 | 150 |
| 665 | 1.25 | X | 1.56 | 1.5 to 1 | 65 | 225 |
| 666 | 1.25 | X | 0.78 | 3 to 1 | 65 | 225 |
| 667 | 1.25 | X | 0.39 | 6 to 1 | 70 | 250 |
| 668 | 1.25 | Y | 1.56 | 1.5 to 1 | 50 | 150 |
| 669 | 1.25 | Y | 0.78 | 3 to 1 | 65 | 225 |
| 670 | 1.25 | Y | 0.39 | 6 to 1 | 20 | 0 |
| 671 | 1.25 | Z | 1.56 | 1.5 to 1 | 70 | 250 |
| 672 | 1.25 | Z | 0.78 | 3 to 1 | 30 | 50 |
| 673 | 1.25 | Z | 0.39 | 6 to 1 | 50 | 150 |
| 674 | 1.25 | AA | 1.56 | 1.5 to 1 | 80 | 300 |
| 675 | 1.25 | AA | 0.78 | 3 to 1 | 85 | 325 |

TABLE 23-continued

Control of Giant Foxtail (Evaluation After 14 Days)

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 676 | 1.25 | AA | 0.39 | 6 to 1 | 55 | 175 |

See footnote to Table 22 for identification of compounds.

EXAMPLE 16

Still additional glycol sulfonates were made up into sprayable comppositions and tested in a manner similar to that set forth in Example 7 except that in some instances a little dimethylsulfoxide was used to aid in preparing the emulsion concentrates and the glycol sulfonates were applied only in combination with atrazine. Also, AATRX 80W wettable powder was used as the source of atrazine and the atrazine compositions each contained 0.6 percent atrazine providing 1.5 lb/acre when applied.

The plant species tested were johnsongrass and giant foxtail, each at the 2 leaf stage. The extent of control obtained was evaluated after 7 days. The results upon johnsongrass are summarized in Table 24, and those upon giant foxtail are summarized in Table 25.

The glycol sulfonates employed are identified in the footnote to Table 24.

TABLE 24

Control of Johnsongrass

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 677 | 1.5 | — | — | — | 10 | — |
| 678 | 1.5 | AB | 1.56 | 2 to 1 | 40 | 300 |
| 679 | 1.5 | AB | 0.78 | 4 to 1 | 40 | 300 |
| 680 | 1.5 | AB | 0.39 | 8 to 1 | 40 | 300 |
| 681 | 1.5 | AC | 1.56 | 2 to 1 | 55 | 450 |
| 682 | 1.5 | AC | 0.78 | 4 to 1 | 40 | 300 |
| 683 | 1.5 | AC | 0.39 | 8 to 1 | 20 | 100 |
| 684 | 1.5 | AD | 1.56 | 2 to 1 | 40 | 300 |
| 685 | 1.5 | AD | 0.78 | 4 to 1 | 50 | 400 |
| 686 | 1.5 | AD | 0.39 | 8 to 1 | 40 | 300 |
| 687 | 1.5 | E | 1.56 | 2 to 1 | 50 | 400 |
| 688 | 1.5 | E | 0.78 | 4 to 1 | 40 | 300 |
| 689 | 1.5 | E | 0.39 | 8 to 1 | 20 | 100 |

Compound AB = 4,4,4-trichloro-2-(3,5-dichlorophenyl)-2-hydroxybutyl-1-(4-(1-methylethyl)-phenyl)sulfonate
Compound AC = 4,4,4-trichloro-2-(3,5-dichlorophenyl)-2-hydroxybutyl-1-(2-methyl-5-chloro-phenyl)sulfonate
Compound AD = 4,4,4-trichloro-2-(3,5-dichlorophenyl)-2-hydroxybutyl-1-(4-ethylphenyl)-sulfonate
Compound E = 4,4,4-trichloro-2-(3,5-dichlorophenyl)-2-hydroxybutyl-1-(4-methylphenyl)-sulfonate

TABLE 25

Control of Giant Foxtail

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 690 | 1.5 | — | — | — | 20 | — |
| 691 | 1.5 | AB | 1.56 | 2 to 1 | 80 | 300 |
| 692 | 1.5 | AB | 0.78 | 4 to 1 | 50 | 150 |
| 693 | 1.5 | AB | 0.39 | 8 to 1 | 50 | 150 |
| 694 | 1.5 | AC | 1.56 | 2 to 1 | 85 | 325 |
| 695 | 1.5 | AC | 0.78 | 4 to 1 | 75 | 275 |
| 696 | 1.5 | AC | 0.39 | 8 to 1 | 45 | 125 |
| 697 | 1.5 | AD | 1.56 | 2 to 1 | 50 | 150 |
| 698 | 1.5 | AD | 0.78 | 4 to 1 | 40 | 100 |
| 699 | 1.5 | AD | 0.39 | 8 to 1 | 40 | 100 |
| 700 | 1.5 | E | 1.56 | 2 to 1 | 85 | 325 |
| 701 | 1.5 | E | 0.78 | 4 to 1 | 75 | 275 |
| 702 | 1.5 | E | 0.39 | 8 to 1 | 40 | 100 |

See footnote to Table 24 for identification of compounds

EXAMPLE 17

A test was conducted to demonstrate the effect of varying the rate of atrazine with respective series of dilutions of an effective glycol sulfonate, 4,4,4-trichloro-2-(3,5-dichlorophenyl)-2-hydroxybutyl-1-(4-methylphenyl)sulfonate.

The compositions were made up and applied in a manner similar to that described in Example 7 except that no soil shielding was carried out, the glycol sulfonate was applied only in combination with atrazine, and the atrazine concentration was changed for each of three series of dilutions of the glycol sulfonate, providing 2, 1.5 and 1 lb/acre, respectively in the respective series, when sprayed.

The test compositions were applied to johnsongrass at the 2½ leaf stage, to barnyard grass green foxtail and yellow millet, each at the 3 leaf stage, and to giant foxtail at the 2½ to 3 leaf stage.

The extent of control of the weed plants under test was evaluated after 20 days and the results summarized in Tables 26 through 29 for tests upon johnsongrass, green foxtail, giant foxtail and yellow millet, respectively. Barnyardgrass was controlled 100% in each test of atrazine alone and the respective combinations.

TABLE 26

Control of Johnsongrass at Varied Atrazine Rates

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 703 | 2 | — | — | — | 10 | — |
| 704 | 2 | E | 1.56 | 2.5 to 1 | 90 | 800 |
| 705 | 2 | E | 0.78 | 5 to 1 | 40 | 300 |
| 706 | 2 | E | 0.39 | 10 to 1 | 20 | 100 |
| 707 | 1.5 | — | — | — | 0 | — |
| 708 | 1.5 | E | 1.56 | 2 to 1 | 60 | ∞ |
| 709 | 1.5 | E | 0.78 | 4 to 1 | 33 | ∞ |
| 710 | 1.5 | E | 0.39 | 8 to 1 | 20 | ∞ |
| 711 | 1 | — | — | — | 0 | — |
| 712 | 1 | E | 1.56 | 1.25 to 1 | 30 | ∞ |
| 713 | 1 | E | 0.78 | 2.5 to 1 | 30 | ∞ |
| 714 | 1 | E | 0.39 | 5 to 1 | 30 | ∞ |

Compound E = 4,4,4-trichloro-2-(3,5-dichlorophenyl)-2-hydroxybutyl-1-(4-methylphenyl)-sulfonate

TABLE 27

Control of Green Foxtail at Varied Atrazine Rates

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 715 | 2 | — | — | — | 100 | — |
| 716 | 2 | E | 1.56 | 2.5 to 1 | 100 | 0 |
| 717 | 2 | E | 0.78 | 5 to 1 | 100 | 0 |
| 718 | 2 | E | 0.39 | 10 to 1 | 100 | 0 |
| 719 | 1.5 | — | — | — | 95 | — |
| 720 | 1.5 | E | 1.56 | 2 to 1 | 100 | 5 |
| 721 | 1.5 | E | 0.78 | 4 to 1 | 100 | 5 |
| 722 | 1.5 | E | 0.39 | 8 to 1 | 100 | 5 |
| 723 | 1 | — | — | — | 48 | — |
| 724 | 1 | E | 1.56 | 1.25 to 1 | 100 | 108 |
| 725 | 1 | E | 0.78 | 2.5 to 1 | 100 | 108 |
| 726 | 1 | E | 0.39 | 5 to 1 | 100 | 108 |

Compound E = 4,4,4-trichloro-2-(3,5-dichlorophenyl)-2-hydroxybutyl-1-(4-methylphenyl)-sulfonate

TABLE 28

Control of Giant Foxtail at Varied Atrazine Rates

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 727 | 2 | — | — | — | 65 | — |
| 728 | 2 | E | 1.56 | 2.5 to 1 | 100 | 54 |
| 729 | 2 | E | 0.78 | 5 to 1 | 100 | 54 |
| 730 | 2 | E | 0.39 | 10 to 1 | 100 | 54 |
| 731 | 1.5 | — | — | — | 40 | — |
| 732 | 1.5 | E | 1.56 | 2 to 1 | 100 | 150 |
| 733 | 1.5 | E | 0.78 | 4 to 1 | 100 | 150 |
| 734 | 1.5 | E | 0.39 | 8 to 1 | 100 | 150 |
| 735 | 1 | — | — | — | 20 | — |
| 736 | 1 | E | 1.56 | 1.25 to 1 | 100 | 400 |
| 737 | 1 | E | 0.78 | 2.5 to 1 | 100 | 400 |
| 738 | 1 | E | 0.39 | 5 to 1 | 100 | 400 |

Compound E = 4,4,4-trichloro-2-(3,5-dichlorophenyl)-2-hydroxybutyl-1-(4-methylphenyl)-sulfonate

TABLE 29

Control of Yellow Millet at Varied Atrazine Rates

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 739 | 2 | — | — | — | 0 | — |
| 740 | 2 | E | 1.56 | 2.5 to 1 | 37 | ∞ |
| 741 | 2 | E | 0.78 | 5 to 1 | 57 | ∞ |
| 742 | 2 | E | 0.39 | 10 to 1 | 30 | ∞ |
| 743 | 1.5 | — | — | — | 0 | — |
| 744 | 1.5 | E | 1.56 | 2 to 1 | 10 | ∞ |
| 745 | 1.5 | E | 0.78 | 4 to 1 | 10 | ∞ |
| 746 | 1.5 | E | 0.39 | 8 to 1 | 10 | ∞ |
| 747 | 1 | — | — | — | 0 | — |
| 748 | 1 | E | 1.56 | 1.25 to 1 | 10 | ∞ |
| 749 | 1 | E | 0.78 | 2.5 to 1 | 10 | ∞ |
| 750 | 1 | E | 0.39 | 5 to 1 | 10 | ∞ |

Compound E = 4,4,4-trichloro-2-(3,5-dichlorophenyl)-2-hydroxybutyl-1-(4-methylphenyl)-sulfonate

EXAMPLE 18

A test was conducted to demonstrate the effect of applying atrazine alone preemergently and subsequently applying a series of respective glycol sulfonates alone postemergently to the plant pots treated with atrazine.

The glycol sulfonate and atrazine compositions were made up in a similar manner to that described in Example 7 except that no combinations were formulated.

Atrazine alone at a concentration of 0.4 percent by weight was applied preemergently to the soil at the rate of 1 lb/acre immediately after seeding of plant pots with giant foxtail and johnsongrass.

The glycol sulfonates were applied alone in serial dilutions when the emerged giant foxtail seedlings were at the 4 leaf stage 13 days after planting and the johnsongrass seedlings were at the 3 leaf stage.

The plant pots were top watered every day, except for a two day period following foliar applications when the pots were subirrigated daily, and maintained under good growing conditions until the extent of herbicidal control was determined for each weedy plant 16 days after foliar applications.

The results are tabulated in Table 30 for control of giant foxtail and in Table 31 for control of johnsongrass.

The glycol sulfonates used are identified in a footnote to Table 30.

TABLE 30

Control of Giant Foxtail - Separate Atrazine Application

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 751 | 1 | — | — | — | 30 | — |
| 752 | 1 | I | 1.56 | 1.25 to 1 | 100 | 233 |
| 753 | 1 | I | 0.78 | 2.5 to 1 | 100 | 233 |
| 754 | 1 | I | 0.39 | 5 to 1 | 90 | 200 |
| 755 | 1 | AB | 1.56 | 1.25 to 1 | 100 | 230 |
| 756 | 1 | AB | 0.78 | 2.5 to 1 | 98 | 193 |
| 757 | 1 | AB | 0.39 | 5 to 1 | 40 | 33 |
| 758 | 1 | AC | 1.56 | 1.25 to 1 | 70 | 133 |
| 759 | 1 | AC | 0.78 | 2.5 to 1 | 60 | 100 |
| 760 | 1 | AC | 0.39 | 5 to 1 | 40 | 33 |
| 761 | 1 | AA | 1.56 | 1.25 to 1 | 75 | 150 |
| 762 | 1 | AA | 0.78 | 2.5 to 1 | 80 | 167 |
| 763 | 1 | AA | 0.39 | 5 to 1 | 80 | 167 |
| 764 | 1 | E | 1.56 | 1.25 to 1 | 98 | 193 |
| 765 | 1 | E | 0.78 | 2.5 to 1 | 95 | 217 |
| 766 | 1 | E | 0.39 | 5 to 1 | 100 | 230 |

Compound E = 4,4,4-trichloro-2-(3,5-dichlorophenyl)-2-hydroxybutyl-1-(4-methylphenyl)-sulfonate
Compound I = 4,4,4-trichloro-2-(3,5-dichlorophenyl)-2-hydroxybutyl-1-(3-(trifluoromethyl)-phenyl)sulfonate
Compound AB = 4,4,4-trichloro-2-(3,5-dichlorophenyl)-2-hydroxybutyl-1-(4-(1-methyethyl)-phenyl)sulfonate
Compound AC = 4,4,4-trichloro-2-(3,5-dichlorophenyl)-2-hydroxybutyl-1-((5-chloro-2-methyl)-phenyl)sulfonate
Compound AA = 4,4,4-trichloro-2-(3,5-dichlorophenyl)-2-trifluoroacetyloxybutyl-1-(2,5-dichlorophenyl)sulfonate

TABLE 31

Control of Johnsongrass - Separate Atrazine Application

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 767 | 1 | — | — | — | 20 | — |
| 768 | 1 | I | 1.56 | 1.25 to 1 | 100 | 400 |
| 769 | 1 | I | 0.78 | 2.5 to 1 | 100 | 400 |

TABLE 31-continued
Control of Johnsongrass - Separate Atrazine Application

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 770 | 1 | I  | 0.39 | 5 to 1    | 95  | 375 |
| 771 | 1 | AB | 1.56 | 1.25 to 1 | 100 | 400 |
| 772 | 1 | AB | 0.78 | 2.5 to 1  | 98  | 390 |
| 773 | 1 | AB | 0.39 | 5 to 1    | 50  | 150 |
| 774 | 1 | AC | 1.56 | 1.25 to 1 | 90  | 350 |
| 775 | 1 | AC | 0.78 | 2.5 to 1  | 90  | 350 |
| 776 | 1 | AC | 0.39 | 5 to 1    | 65  | 225 |
| 777 | 1 | AA | 1.56 | 1.25 to 1 | 100 | 400 |
| 778 | 1 | AA | 0.78 | 2.5 to 1  | 100 | 400 |
| 779 | 1 | AA | 0.39 | 5 to 1    | 50  | 150 |
| 780 | 1 | E  | 1.56 | 1.25 to 1 | 100 | 400 |
| 781 | 1 | E  | 0.78 | 2.5 to 1  | 100 | 400 |
| 782 | 1 | E  | 0.39 | 5 to 1    | 98  | 390 |

See footnote to Table 30 for identification of compounds.

EXAMPLE 19

Additional glycol sulfonates were made up into sprayable compositions containing atrazine and tested against giant foxtail seedlings in a manner similar to that described in Example 7 except that a small amount of dimethylsulfoxide was used to bring the glycol sulfonates into solution in the concentrate, the glycol sulfonates were applied only in combination with atrazine, atrazine was applied alone and in the combination at a rate of 1.5 lb/acre, and the soil was not shielded with vermiculite.

The giant foxtail plants were at the 4 leaf stage and were 4 inches tall when sprayed. The extent of herbicidal control was obtained after 14 days. The results are summarized in Table 32, the compounds tested being identified in a footnote thereto.

TABLE 32
Control of Giant Foxtail

| Run Number | Atrazine Dosage lb/acre | Glycol Sulfonate Compound | Sulfonate Dosage, lb mol/acre × 1000 | Approx. Weight Ratio Atrazine to Sulfonate | Observed Control % | Percent Increase Over Control By Atrazine Alone |
|---|---|---|---|---|---|---|
| 783 | 1.5 | —  | —    | —       | 40  | —   |
| 784 | 1.5 | AE | 1.56 | 2 to 1  | 100 | 150 |
| 785 | 1.5 | AE | 0.78 | 4 to 1  | 90  | 125 |
| 786 | 1.5 | AE | 0.39 | 8 to 1  | 83  | 108 |
| 787 | 1.5 | AF | 1.56 | 2 to 1  | 50  | 25  |
| 788 | 1.5 | AF | 0.78 | 4 to 1  | 53  | 33  |
| 789 | 1.5 | AF | 0.39 | 8 to 1  | 40  | 0   |
| 790 | 1.5 | AG | 1.56 | 2 to 1  | 80  | 100 |
| 791 | 1.5 | AG | 0.78 | 4 to 1  | 50  | 25  |
| 792 | 1.5 | AG | 0.39 | 8 to 1  | 50  | 25  |
| 793 | 1.5 | AH | 1.56 | 2 to 1  | 94  | 135 |
| 794 | 1.5 | AH | 0.78 | 4 to 1  | 96  | 140 |
| 795 | 1.5 | AH | 0.39 | 8 to 1  | 93  | 133 |
| 796 | 1.5 | AI | 1.56 | 2 to 1  | 40  | 0   |
| 797 | 1.5 | AI | 0.78 | 4 to 1  | 40  | 0   |
| 798 | 1.5 | AI | 0.39 | 8 to 1  | 40  | 0   |
| 799 | 1.5 | E  | 1.56 | 2 to 1  | 100 | 150 |
| 800 | 1.5 | E  | 0.78 | 4 to 1  | 99  | 148 |
| 801 | 1.5 | E  | 0.39 | 8 to 1  | 99  | 148 |
| 802 | 1.5 | E  | 0.20 | 16 to 1 | 90  | 125 |
| 803 | 1.5 | E  | 0.10 | 32 to 1 | 60  | 50  |
| 804 | 1.5 | AB | 1.56 | 2 to 1  | 96  | 140 |
| 805 | 1.5 | AB | 0.78 | 4 to 1  | 96  | 140 |
| 806 | 1.5 | AB | 0.39 | 8 to 1  | 80  | 100 |

Compound E = 4,4,4-trichloro-2-(3,5-dichlorophenyl)-2-hydroxybutyl-1-(4-methylphenyl)sulfonate
Compound AB = 4,4,4-trichloro-2-(3,5-dichlorophenyl)-2-hydroxybutyl-1-(4-ethylphenyl)sulfonate
Compound AE = 4,4,4-trichloro-2-(3,5-dichlorophenyl)-2-hydroxybutyl-1-(β-styryl)sulfonate
Compound AF = 4,4,4-trichloro-2-(3,5-dichlorophenyl)-2-acetyloxybutyl-1-methylsulfonate
Compound AG = 4,4,4-trichloro-2-(3,5-dichlorophenyl)-2-propionyloxybutyl-1-methylsulfonate
Compound AH = 4,4,4-trichloro-2-(3,5-dichlorophenyl)-2-hydroxybutyl-1-(2-thienyl)sulfonate
Compound AI = 4,4,4-trichloro-2-(3,5-dichlorophenyl)-2-hydroxybutyl-1-(4-methylphenyl)sulfamate

EXAMPLE 20

In a further series of tests three glycol sulfonates previously tested were again applied in a manner similar to that described in Example 7 except that the application rates of the glycol sulfonates extended down to about 0.1 lb/acre and all glycol sulfonates were applied only in combination with atrazine. A small amount of dimethylsulfoxide was used to bring the glycol sulfonates into solution in making the concentrates.

All atrazine-containing compositions were applied at a rate of 1.5 lb/acre atrazine.

The test plants were giant foxtail seedlings one group of which was 3 inches tall and at the 3 leaf stage. The other group was 4½ inches tall and at the 4 leaf stage at the time of spraying.

The extent of control of the test plants was evaluated after 15 days and the results summarized in Tables 33 and 34, respectively, for results on the 4 leaf giant foxtail, and, 3 leaf giant foxtail.

The glycol sulfonates employed are identified in a footnote to Table 32.

TABLE 33

Control of Giant Foxtail at Three Leaf Stage

| Run Number | Atrazine Dosage lb/acre | Glycol Sulfonate Compound | Sulfonate Dosage, lb mol/acre × 1000 | Approx. Weight Ratio Atrazine to Sulfonate | Actual Control % | Percent Enhancement Over Control By Atrazine Alone |
|---|---|---|---|---|---|---|
| 837 | 1.5 | — | — | — | 50 | — |
| 838 | 1.5 | AE | 1.56 | 2 to 1 | 99 | 98 |
| 839 | 1.5 | AE | 0.78 | 4 to 1 | 80 | 60 |
| 840 | 1.5 | AE | 0.39 | 8 to 1 | 77 | 54 |
| 841 | 1.5 | AE | 0.20 | 16 to 1 | 93 | 86 |
| 842 | 1.5 | AH | 1.56 | 2 to 1 | 87 | 74 |
| 843 | 1.5 | AH | 0.78 | 4 to 1 | 93 | 86 |
| 844 | 1.5 | AH | 0.39 | 8 to 1 | 95 | 90 |
| 845 | 1.5 | AH | 0.20 | 16 to 1 | 98 | 96 |
| 846 | 1.5 | E | 1.56 | 2 to 1 | 100 | 100 |
| 847 | 1.5 | E | 0.78 | 4 to 1 | 100 | 100 |
| 848 | 1.5 | E | 0.39 | 8 to 1 | 100 | 100 |
| 849 | 1.5 | E | 0.20 | 16 to 1 | 100 | 100 |

See footnote to Table 32 for identification of compounds.

TABLE 34

Control of Giant Foxtail at Four Leaf Stage

| Run Number | Atrazine Dosage lb/acre | Glycol Sulfonate Compound | Sulfonate Dosage, lb mol/acre × 1000 | Approx. Weight Ratio Atrazine to Sulfonate | Actual Control % | Percent Enhancement Over Control By Atrazine Alone |
|---|---|---|---|---|---|---|
| 807 | 1.5 | — | — | — | 40 | — |
| 808 | 1.5 | AE | 1.56 | 2 to 1 | 53 | 33 |
| 809 | 1.5 | AE | 0.78 | 4 to 1 | 77 | 93 |
| 810 | 1.5 | AE | 0.39 | 8 to 1 | 53 | 33 |
| 811 | 1.5 | AE | 0.20 | 16 to 1 | 53 | 33 |
| 812 | 1.5 | AH | 1.56 | 2 to 1 | 50 | 25 |
| 813 | 1.5 | AH | 0.78 | 4 to 1 | 60 | 50 |
| 814 | 1.5 | AH | 0.39 | 8 to 1 | 43 | 58 |
| 815 | 1.5 | AH | 0.20 | 16 to 1 | 50 | 28 |
| 816 | 1.5 | E | 1.56 | 2 to 1 | 94 | 135 |
| 817 | 1.5 | E | 0.78 | 4 to 1 | 92 | 130 |
| 818 | 1.5 | E | 0.39 | 8 to 1 | 92 | 130 |
| 819 | 1.5 | E | 0.20 | 16 to 1 | 57 | 43 |

See footnote to Table 32 for identification of compounds.

EXAMPLE 21

A field test was conducted in which atrazine was applied preemergently and a combination of atrazine and a glycol sulfonate was applied over the top postemergently.

Shortly after seeding a field plot of sandy loam soil to corn, the soil containing an indigenous infestation of giant foxtail, the plot was divided into three zones. AATREX 4L brand of atrazine flowable concentrate was made up into an aqueous tank mix and sprayed on the first zone at a rate to provide 2 lbs/acre atrazine and on the second zone at a rate of 1 lb/acre atrazine, while no atrazine was applied to the third zone.

The entire plot then received one inch of irrigation water by sprinkler, a procedure repeated approximately every ten days during the course of the test.

AATREX 4L brand of atrazine was used along with a crop oil concentrate to make up aqueous tank mixes to provide, when sprayed at the rate of 30 gal/acre, 0.5 lb/acre atrazine and one quart/acre crop oil concentrate, and 1 lb/acre atrazine and one quart/acre crop oil concentrate, and respective portions of each zone were so sprayed 17 days after the preemergent treatment.

An emulsifiable concentrate was prepared containing by weight 12.9 percent of 4,4,4-trichloro-2-(3,5-dichlorophenyl)-2-hydroxybutyl-1-(4-methylphenyl)-sulfonate, 10.7 percent of a 50:50 mixture of ATLOX 3403F and ATLOX 3404 brands of surface-active agents and the balance xylene, resulting in a composition containing 1 lb/gal of the sulfonate compound. ATLOX 3403F surfactant is a proprietary blend about 75 percent of which is a mixture of calcium dodecylbenzene sulfonate with a polyoxyethylene nonyl phenol and a polyethoxylated $C_{12}$–$C_{18}$ ester and the balance about 13 percent methanol and about 15 percent of an aromatic solvent. ATLOX 3403F surfactant is a similar mixture not containing the polyethoxylated ester.

The emulsifiable concentrate and a crop oil concentrate were used to make up aqueous tank mixes which when sprayed at the rate of 30 gal/acre provided 0.125 lb/acre of the glycol sulfonate and 1 quart/acre crop oil concentrate, and, 0.25 lb/acre of the glycol sulfonate and 1 quart/acre dcrop oil concentrate and were also so sprayed upon additional respective portions of each zone 17 days after the preemergent treatment.

Additional tank mixes were made up according to the invention to contain the requisite amounts of atrazine and glycol sulfonate to provide, respectively, in each 30 gal, 0.5 lb atrazine and 0.125 lb glycol sulfonate; 0.5 lb atrazine and 0.25 lb glycol sulfonate; 1 lb atrazine and 0.125 lb glycol sulfonate; and 1 lb atrazine and 0.25 lb glycol sulfonate. Each tank mix was also made up to contain 1 quart crop oil concentrate for each 30 gal of tank mix. The resulting respective tank mixes were sprayed at the rate of 30 gal/acre upon additional respective portions of each of the three zones in accordance with the invention 17 days after the preemergent treatments.

Yet additional portions of the three zones remained without postemergent treatments. The giant foxtail weeds and the corn in these and the portions given postemergent treatments were each evaluated 35 days after the postemergent treatments for percent control of giant foxtail and of corn. Substantially no injury to corn was observed in any of these treatments. The observed control of giant foxtail is tabulated in the following table, Table 35.

TABLE 35

Control of Giant Foxtail With Split Applications

| No. | Treatments Postemergent Active | lbs/acre | Preemergent | lbs/acre Atrazine 0 % Control | 1 Giant | 2 Foxtail |
|---|---|---|---|---|---|---|
| 1. | none | — | | 0 | 10 | 50 |
| 2. | atrazine | 0.5 | | 7 | 23 | 72 |
| 3. | atrazine sulfonate | 0.5 | 0.125 | 10 | 83 | 93 |
| 4. | atrazine sulfonate | 0.5 | 0.25 | 13 | 77 | 89 |
| 5. | atrazine | 1 | | 3 | 50 | 75 |
| 6. | atrazine sulfonate | 1 | 0.125 | 17 | 82 | 96 |
| 7. | atrazine sulfonate | 1 | 0.25 | 23 | 93 | 99 |
| 8. | sulfonate | | 0.125 | 0 | 23 | 60 |
| 9. | sulfonate | | 0.25 | 0 | 43 | 68 |

The results of treatments 3, 4, 6 and 7 of combination pre- and postemergent applications according to the invention show enhanced effective control of giant foxtail, while treatments 8 and 9 wherein the glycol sulfonate alone is applied postemergently over the top of prior applications of atrazine likewise show greatly enhanced control of giant foxtail at lower control levels.

The glycol sulfonates and glycol sulfamates utilized according to the invention are also useful in enhancing the herbicidal activity of the following herbicides when applied together or sequentially in a similar manner to that described hereinabove: acetochlor, alachlor, barban, butachlor, butylate, CDAA, CDEC, cycloate, diallate, diethatyl ethyl, EPTC, metham, metolachlor, molinate, pebulate, propachlor, propanil, thiobencarb, triallate and vernolate.

Other specific suitable compounds that may be prepared according to the methods described above and utilized according ot the present invention included those identified in the following table:

$$R-SO_2-O-CH_2-\underset{\underset{\text{}}{|}}{\overset{\overset{OT}{|}}{C}}-CH_2-CR^1Cl_2$$

with phenyl substituted with X and Y

| R | T | X | Y | $R^1$ |
|---|---|---|---|---|
| 2-chlorophenyl | H | Cl | Cl | Cl |
| 2-nitrophenyl | H | Cl | Cl | Cl |
| 2,4-dichlorophenyl | H | Cl | Cl | Cl |
| 2,4,5-trichlorophenyl | H | Cl | Cl | Cl |
| 4-methylphenyl | $-\overset{O}{\underset{\|}{C}}-CH_3$ | Cl | Cl | Cl |
| 3-chloropropyl | H | Cl | Cl | Cl |
| β-naphthyl | H | Cl | Cl | Cl |
| 8-quinolinyl | H | Cl | Cl | Cl |
| α-naphthyl | H | Cl | Cl | Cl |
| 5,7-dimethyl(1,2,4)-triazolo-(5,1-a)-pyrimidine-2- | H | Cl | Cl | Cl |
| 5-(1,1-dimethylethyl)-1,2,4-triazol-3-yl- | H | Cl | Cl | Cl |
| methoxycarboxymethoxy | H | Cl | Cl | Cl |
| 1-methylethoxycarboxymethoxy | H | Cl | Cl | Cl |
| 4-methylphenyl | H | H | Cl | Cl |
| methyl | H | H | Cl | Cl |
| ethyl | H | H | Cl | Cl |
| 1-methylethyl | H | H | Cl | Cl |
| n-butyl | H | H | Cl | Cl |
| chloromethyl | H | H | Cl | Cl |
| 4-chlorophenyl | H | H | Cl | Cl |
| 2,5-dichlorophenyl | H | H | Cl | Cl |
| 4(1-methylethyl)phenyl | H | H | Cl | Cl |
| β-naphthyl | H | H | Cl | Cl |

-continued

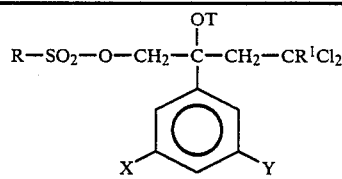

| R | T | X | Y | R¹ |
|---|---|---|---|---|
| α-naphthyl | H | H | Cl | Cl |
| 8-quinolinyl | H | H | Cl | Cl |
| 3-chloropropyl | H | H | Cl | Cl |
| 2-(trifluoromethyl)phenyl | H | Cl | Cl | Cl |
| 4-methylphenyl | H | F | Cl | Cl |
| 4-(1,1,-dimethylethyl)phenyl | H | Cl | Cl | Cl |
| 4-methylphenyl | H | $CF_3$ | Cl | Cl |
| 3,5-dichlorophenyl | H | Cl | Cl | Cl |
| 3-(trifluoromethyl)phenyl | H | H | Cl | Cl |
| 4-(1-methylethyl)phenyl | H | H | $CF_3$ | Cl |
| 2,5-dichlorophenyl | H | H | $CF_3$ | Cl |
| chloromethyl | H | H | $CF_3$ | Cl |
| 1-methylethyl | H | H | $CF_3$ | Cl |
| methyl | H | H | $CF_3$ | Cl |
| 4-methylphenyl | H | H | $CF_3$ | Cl |
| 2-(trifluromethyl)phenyl | H | F | Cl | Cl |
| 4-methylphenyl | H | Cl | Cl | F |
| 4-methylphenyl | H | Cl | Cl | Br |
| 4-methylphenyl | H | Cl | Cl | $CH_3$ |
| 4-methylphenyl | H | Cl | Cl | $-\overset{O}{\underset{\|}{C}}-NH_2$ |
| 4-(2,2-dimethylethyl)phenyl | $-\overset{O}{\underset{\|}{C}}-CH_3$ | Cl | Cl | Cl |
| 4-methylphenyl | $-\overset{O}{\underset{\|}{C}}-CH_2CH_3$ | Cl | Cl | Cl |
| 1-methylethyl | $-\overset{O}{\underset{\|}{C}}-CH_3$ | Cl | Cl | Cl |
| 4-methylphenylamino | H | Cl | Cl | Cl |
| 4-chlorophenylamino | H | Cl | Cl | Cl |
| 2,5-dichlorophemylamino | H | Cl | Cl | Cl |
| 4-methylphenylamino | H | F | Cl | Cl |
| 3-nitrophenyl | H | Cl | Cl | Cl |
| cyclopropyl | H | Cl | Cl | Cl |
| 4-(methylthio)phenyl | H | Cl | Cl | Cl |
| dimethylamino | H | Cl | Cl | Cl |
| 8-quinolinylamino | H | Cl | Cl | Cl |
| pyridin-2-ylamino | H | Cl | Cl | Cl |
| 3-chloro-5-trifluoropyridin-2-ylamino | H | Cl | Cl | Cl |
| phenylmethylamino | H | Cl | Cl | Cl |
| 3,5-dichlorophenylamino | H | Cl | Cl | Cl |

EXAMPLE 22

Preparation of 4,4,4-trichloro-2-(3,5-dichlorophenyl)-1,2-butanediol-1-acetate represented by the formula:

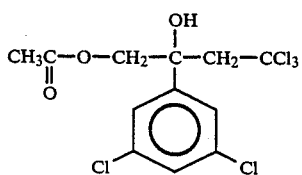

250 grams (g) of 2-(3,5-dichlorophenyl)-2-(2,2,2-trichloroethyl)oxirane was dissolved in 1.0 liter (l) of acetic acid in a 3.0 l three necked flask. 224 Grams of anhydrous sodium acetate was added to the solution which resulted in a slurry. The slurry was heated to about 85° C., becoming homogenous at about 65° C. The reaction was allowed to proceed for 36 hours (hr) at which time the reaction mixture was cooled. The reaction mixture was then heated to about 70° C., poured into a separatory funnel and diluted with 1500 milliliters (ml) of water and 1200 ml of methylene chloride. The resulting organic layer was separated from the aqueous layer and washed with water (1500 ml) and 5 percent sodium bicarbonate (1000 ml) and dried with sodium sulfate. Removal of the solvent in vacuo afforded 290.4 g (97.9 percent yield) of the desired product as a yellow oil which was shown to be 98.9 percent pure by gas chromatography analysis.

EXAMPLE 23

Preparation of 4,4,4-trichloro-2-(3,5-dichlorophenyl)-1,2-butanediol represented by the formula:

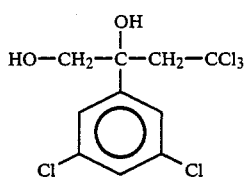

288.5 Grams of 4,4,4-trichloro-2-(3,5-dichlorophenyl)-1,2-butanediol-1-acetate was dissolved in 500 ml of methanol in a 1.0 liter round bottom flask. 2.9 Grams of p-toluenesulfonic acid monohydrate was added and the solution was heated at reflux for 18 hr and the cooled. The reaction mixture was then diluted with 750 ml of methylene chloride and washed three times with water (750 ml portions) and 5 percent sodium bicarbonate (750 ml). The organic layer was dried with sodium sulfate and the solvent was removed in vacuo, leaving 256.4 g of the desired product as a yellow oil.

EXAMPLE 24

Preparation of 4,4,4-trichloro-2-(3,5-dichlorophenyl)-1,2-butanediol-1-isopropyl-sulfonate ester represented by the formula:

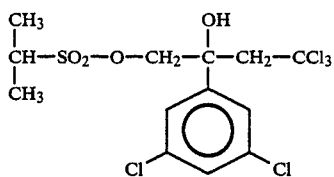

6.77 Grams of 4,4,4-trichloro-2-(3,5-dichlorophenyl)-1,2-butanediol was dissolved in 50 ml of benzene in a 250 ml flask. 2.99 Grams of isopropylsulfonyl chloride was added to the solution. The solution was cooled to about 10° C. in an ice bath and then a solution of 2.12 g of triethylamine in 25 ml of benzene was added dropwise over 15 minutes. The ice bath was then removed and the reaction mixture was stirred at room temperature for about 24 hr which resulted in precipitation of triethylamine hydrochloride from the reaction mixture. The reaction mixture was then diluted with about 25 ml of benzene and then washed with 100 ml of water followed by 100 ml of 10 percent of sodium bicarbonate followed by 100 ml of 3.7 percent hydrochloric acid. The organic layer was dried with sodium sulfate and then the solvent was removed in vacuo at 55° C. which resulted in a thick oil which crystallized upon standing at 55° C. Recrystallization was carried out with 20 ml of methylcyclohexane. On cooling, the desired product crystallized as a white product and was collected by filtration, then washed with 20 ml of hexane and then dried at 80° C. in vacuo. The yield was 5.63 g of the desired product identified by nuclear magnetic resonance analysis. Melting point was 105°-106.5° C.

|  | Weight Percent |
|---|---|
| Analysis calculated for $C_{13}H_{15}Cl_5O_4S$: | C 35.12, H 3.40 |
| Found: | C 35.3, H 3.44 |

EXAMPLE 25

Preparation of 4,4,4-trichloro-2-(3,5-dichlorophenyl)-1,2-butanediol-1-α-chloromethylsulfonate represented by the formula:

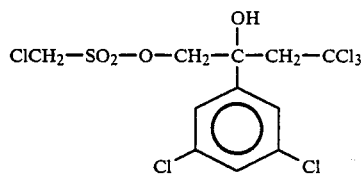

6.77 Grams of 4,4,4-trichloro-2-(3,5-chlorophenyl)-1,2-butanediol and 3.13 g of chloromethylsulfonyl chloride were dissolved in 50 ml of benzene in a 250 ml flask. The resulting solution was cooled in an ice bath to 10° C. and a solution of 2.12 g of triethylamine in 25 ml of benzene was added over 15 minutes. The ice bath was removed and then the mixture was stirred at room temperature for 5 hr during which time triethylamine hydrochloride precipitated. The reaction mixture was then washed with water (100 ml) followed by 10 percent sodium bicarbonate (100 ml) followed by two washings with 3.7 percent hydrochloric acid (100 ml portions). The organic layer was dried with sodium sulfate and the solvent was removed in vacuo at 55° C. which resulted in an oil. The oil was taken up in 20b ml of refluxing methylcyclohexane and cooled. Upon cooling the oil precipitated. The mixture was then placed in a refrigerator for several days. The mixture was the allowed to stir at room temperature for 2 days with 10 ml of methylcyclohexane added to facilitate stirring. During the 2 day stirring period a white solid crystallized out. The white solid was collected by filtration, washed twice with hexane (15 ml portions) and dried at 60° C. in vacuo, which yielded 5.36 g of the desired product, melting point 74°-76.5° C.

|  | Weight Percent |
|---|---|
| Analysis calculated for $C_{11}H_{10}Cl_6O_4S$: | C 29.29, H 2.24 |
| Found: | C 29.55, H 2.26 |

EXAMPLE 26

Preparation of 4,4,4-trichloro-2-(3,5-dichlorophenyl)-1,2-butanediol-1-p-toluenesulfonate represented by the formula:

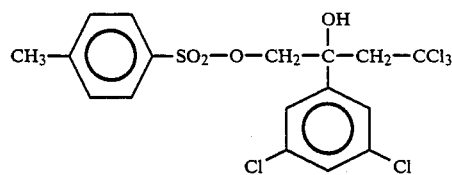

6.77 Grams of 4,4,4-trichloro-2-(3,5-dichlorophenyl)-1,2-butanediol was dissolved in 30 ml of benzene in 250 ml flask. To the solution was added 4.0 g of p-toluenesulfonyl chloride and the solution cooled to 10° C. in an ice bath. A solution of 2.12 g of triethylamine and 1.0 g of 4-dimethylaminopyridine in 25 ml of benzene was added dropwise to the solution over about 10 minutes.

The resulting reaction mixture was held at 10° C. for 15 minutes and then stirred at room temperature for 2.5 hr during which time triethylamine hydrochloride precipitated. The reaction mixture was then diluted with about 25 ml of benzene and washed with water (100 ml) followed by two washings with 3.7 percent hydrochloric acid (100 ml portions) and then dried with sodium sulfate. The solvent was removed in vacuo which resulted in a thick oil. The thick oil was allowed to stand several days at room temperature. The thick oil was then dissolved in 25 ml of methylcyclohexane, heated to reflux then placed in a refrigerator. After several days a white crystalline solid formed. The crystalline solid-methylcyclohexane mixture was stirred at room temperature overnight and the crystalline solid was collected by filtration. The crystalline solid was then washed with 25 ml of hexane and dried at 80° C. which yielded 7.0 g of the desired product, melting point 106°–108.5° C.

|  | Weight Percent |
|---|---|
| Analysis calculated for $C_{17}H_{15}Cl_5O_4S$: | C 41.44, H 3.07 |
| Found: | C 41.5, H 3.09 |

EXAMPLE 27

Preparation of 4,4,4-trichloro-2-(3,5-dichlorophenyl)-1,2-butanediol-1-(m-trifluoromethylbenzenesulfonate) represented by the formula:

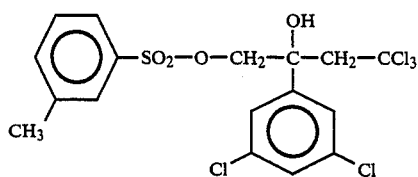

7.9 Grams of 4,4,4-trichloro-2-(3,5-dichlorophenyl)-1,2-butanediol was dissolved in 50 ml of benzene in a 250 ml three-necked flask. To the solution was added 6.0 g of m-trifluoromethylbenzenesulfonyl chloride and then the solution was cooled to about 10° C. in an ice bath. A solution of 1.0 g of 4-dimethylaminopyridine and 2.48 g of triethylamine in 25 ml of benzene was added dropwise to the solution over about 10 minutes during which time triethylamine hydrochloride precipitated. The ice bath was then removed and the reaction mixture was stirred at room temperature for 2.5 hr. The reaction mixture was then washed with water (100 ml) followed by two washings with 3.7 percent hydrochloric acid (100 ml portions) followed by a water wash (100 ml). The organic layer was dried with sodium sulfate and the solvent removed in vacuo at 55° C. which resulted in a yellow oil. The yellow oil failed to yield crystalline product from any of methylcyclohexane, benzene, hexane and methylene chloride. After a number of such attempts the yellow oil was then added to 20 ml of methylene chloride and purified by liquid chromatography. After removal of the solvents required during the chromatography procedure, 5.0 g of the desired product was obtained as a yellow oil.

|  | Weight Percent |
|---|---|
| Analysis calculated for $C_{17}H_{12}Cl_5F_3O_4S$: | C 37.35, H 2.21 |
| Found: | C 37.24, H 2.17 |

EXAMPLE 28

Preparation of 4,4,4-trichloro-2-(3,5-dichlorophenyl)-1,2-butanediol-1-(2,5-dichlorophenylsulfonate) represented by the formula:

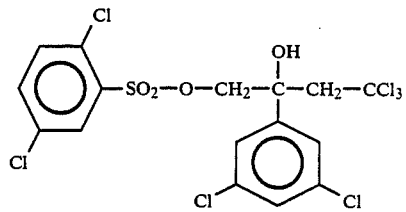

68.1 Grams of 4,4,4-trichloro-2-(3,5-dichlorophenyl)-1,2-butanediol was dissolved in 250 ml of pyridine in a 500 ml flask. To the solution was added 54.3 g of 2,5-dichlorobenzenesulfonyl chloride and 25 ml of pyridine. The reaction mixture was cooled to 25° C. in an ice bath and then removed from the ice bath and stirred at room temperature for about 21 hr. The reaction mixture was then diluted with 500 ml of benzene and washed twice with water (800 ml portions) followed by two washings with 7.4 percent hydrochloric acid (1 liter portions). The organic layer was treated with activated carbon and dried with sodium sulfate. The solvent was then removed in vacuo leaving a reddish orange oil which crystallized upon cooling and scratching the container. The crystallized product was dissolved in 150 ml of refluxing methylcyclohexane and upon cooling, the product recrystallized. The mixture was stirred overnight at room temperature, the crystalline product was collected by filtration, washed twice with hexane (75 ml) and dried at 70° C. in vacuo leaving 78.5 g of the desired product as an off white product, melting point 109°–110° C.

|  | Weight Percent |
|---|---|
| Analysis calculated for $C_{16}H_{11}Cl_7O_4S$: | C 35.10, H 2.03 |
| Found: | C 35.30, H 2.08 |

EXAMPLE 29

Preparation of 4,4,4-trichloro-2-(3-chloro-5-fluorophenyl)-2-hydroxybutyl-1-(4-methylphenyl)sulfonate represented by the formula:

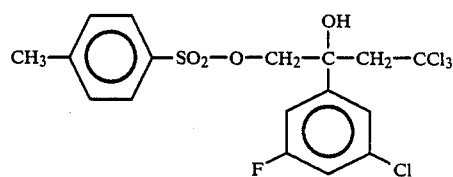

Into a 250 ml round bottom flask was placed 11.6 g (0.0609 mole) of p-toluenesulfonic acid monohydrate and 120 ml of benzene and slurried together. The slurry was heated at reflux with a Dean-Stark trap to remove the water of hydration. After about 1.2 hours, about 1.5 ml of water had collected and the anhydrous acid had become soluble in the benzene. The solution was cooled to 55° C. and 2.41 g (0.0305 mole) of pyridine and 0.3 ml additional benzene were added and then 8.44 g (0.0277 mole) of 2-(2,2,2-trichloroethyl)-2-(3-chloro-5-fluorophenyl)oxirane and yet 15 ml additional benzene. The cloudy reaction mixture was heated at reflux for 4.5 hours, becoming homogenous. The solution was allowed to stir at room temperature overnight with the pyridine salt of p-toluenesulfonic acid crystallizing out.

The slurry was diluted with about 75 ml of benzene and then washed three times with 150 ml portions of water, a 200 ml portions of 5 percent by weight aqueous NaHCO3 solution, and finally a 150 ml portion of 9.1 percent by weight hydrochloric acid. The organic layer was separated and dried with Na2SO4 and the solvent removed in vacuo leaving 11.9 grams of crystalline product.

The product was taken up in 25 ml of methylcyclohexane at reflux temperature. The solution was allowed to cool and then stirred at room temperature for about an hour, resulting in precipitation of a white crystalline product which was collected by filtration and washed twice with 15 ml portions of hexane and dried at 80° C. in vacuo. 10.5 g of white crystalline product melting at 112.5° to 114.5° C. and identified as 4,4,4-trichloro-2-(3-chloro-5-fluorophenyl)-2-hydroxybutyl)-1-(4-methylphenyl)sulfonate was obtained.

Elemental analysis showed the following: Calculated: %C, 42.8; % H, 3.18; Found: % C, 42.8; % H, 3.22.

EXAMPLE 30

Preparation of 4,4,4-trichloro-2-(3-chloro-5-(trifluoromethyl)phenyl)-2-hydroxybutyl-1-(4 -methylphenyl)sulfonate represented by the formula:

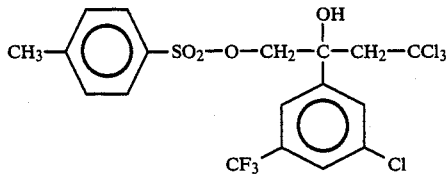

In a 250 ml round bottom flask was slurried 11.0 g (0.0579 mole) of p-toluenesulfonic acid monohydrate in 120 ml of benzene. The slurry was heated at reflux and a Dean-Stark trap was used to remove about 1.0 ml of water. After about 1.5 hours, the mixture was a homogeneous solution. The solution was cooled and a Dean-Stark trap removed from the system. When the flask and contents were at 55° C., there was added 2.29 g (0.0289 mole) of pyridine, 3 ml additional pyridine followed by 9.3 g (0.0263 mole) of 2-(3-chloro-5-trifluoromethylphenyl)-2-(2,2,2-trichloroethyl)oxirane in 15 ml of benzene. The cloudy mixture was heated at reflux for 4.5 hours becoming clear as the reaction proceeded. The reaction mixture was cooled to and stirred at room temperature overnight with the p-toluenesulfonic acid-pyridine salt precipitating.

The reaction mixture was diluted with about 100 ml of benzene and then washed twice with 200 ml portions of water, once with a 200 ml portion of 5 percent by weight aqueous NaHCO3 solution and then a 200 ml portion of 9.1 percent by weight hydrochloric acid. The organic layer was separated and dried with a mixture of anhydrous Na2SO4 plus powdered charcoal. The charcoal did not decolorize the orange colored solution.

The solvent was then removed from the product mixture in vacuo leaving an oil which was held at 55° C. under less than 3 mm Hg partial pressure for 1 hour, and on cooling and scratching, crystallization took place yielding 12.7 grams of crude solid.

The crude product was recrystallized from methylcyclohexane. This was done by taking up the solid initially in 25 ml of methylcyclohexane in reflux temperature. On cooling and scratching the receptacle, an oil initially separated but became crystalline and as crystallization proceeded the slurry became quite thick. Another 10 ml of methylcyclohexane was added and the slurry stirred at room temperature for about 1 hour after which the white crystalline product was collected by filtration and washed with 225 ml portions of hexane and air dried overnight, yielding 10 grams of material melting at 87° to 88° C. NMR analysis and elemental analysis confirmed the product to be 4,4,4-trichloro-2-(3-chloro-5-(trifluoromethyl)phenyl)-2-hydroxybutyl-1-(4-methylphenyl)sulfonate.

Calculated: % C, 41.08; % H, 2.87; Found: % C, 41.01; % H, 2.90.

EXAMPLE 31

Preparation of 2-(3-(trifluoromethylphenyl)-4,4,4-trichloro-2-hydroxybutyl-1-(4-methylphenyl)-sulfonate represented by the formula:

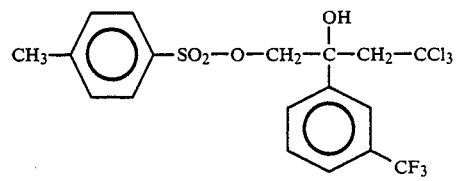

In a 250 ml, three-necked, round bottom flask equipped with a thermometer, a condenser and a Dean-Stark trap as placed a magnetic stirrer bar, 8.75 g (0.046 mole) of p-toluenesulfonic acid monohydrate and 50 ml of benzene. The thick slurry was heated and stirred at reflux for about 4 hours during which the theoretical amount of water of hydration was collected in the trap and the reaction mixture had become a solution. The flask and its contents were then cooled to about 30° C. and 1.74 g (0.0978 mole) of pyridine was added dropwise, the reaction mixture becoming turbid. Then 7.0 g (0.022 mole) of 4,4,4-trichloro-1,2-epoxy-2-(3-(trifluoromethyl)phenyl)butane was added to the flask and the reaction mixture was heated to reflux, the initial turbidity disappearing as the reaction mixture was heated to reflux, becoming homogeneous and a clear light yellow color. The reaction mixture was heated at reflux for 4 hours, cooled and poured into a separatory funnel. A white crystalline solid believed to be a pyridine salt of the sulfonic acid was observed.

The benzene layer was washed twice with 50 ml portions of water, once with a 50 ml portion of aqueous NaHCO3 solution and once with a 50 ml portion of dilute aqueous hydrochloric acid containing 25 ml of concentrated HCl per 100 ml of water. The organic layer was recovered and dried over Na2SO4. The solvent was then removed on a rotary evaporator at a temperature of 50° C. The residual oil was maintained at 50° C. while the last traces of solvent were removed under reduced pressure. The oil was then taken up in methylcyclohexane, brought to reflux, cooled and stirred, whereupon a white crystalline solid separated and was collected by filtration and washed with 210 ml portions of n-hexane, yielding 7.58 g of white crystalline solid having a melting point of 75° to 79° C. The product was subjected to elemental analysis, confirming that the product was 2-(3-trifluoromethylphenyl)-4,4,4-trichloro-2-hydroxybutyl-1-(4-methylphenyl)sulfonate.

Calculated: % C, 43.96; % H, 3.28 Found: % C, 44.0; % H, 3.37

What is claimed is:

1. A herbicidal composition for use in postemergent agricultural field operations which comprises, in admixture, an agriculturally acceptable carrier and an effective amount in the range of, by weight, from about 1 to about 20 parts of a herbicidal triazine or mixture of herbicidal triazines and as a second herbicidal component, 1 to 2 parts of a glycol sulfonate or sulfamate compound or mixture of such compounds each having the following formula:

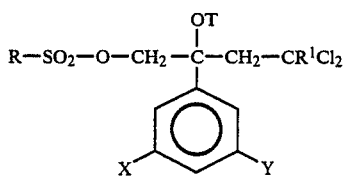

wherein:

R is $C_1$ to $C_{18}$ alkyl; $C_1$ to $C_4$ haloalkyl; $C_3$ to $C_6$ cycloalkyl; phenyl; naphthyl; benzyl; any of phenyl, naphthyl, or benzyl in which up to three hydrogens on the ring have been replaced by substituent groups which may be the same or different and are selected from the group consisting of methyl, methoxy, methylthio, chloro, bromo, $CF_3$ or nitro; or $NR^2R^3$;

$R^1$ is $CH_3$, Cl, Br, F or

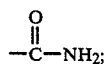

X and Y are the same or different and are Cl, Br, F, $CF_3$ or H, provided X and Y may not both be H; and $R^2$ is H or $C_1$ to $C_4$ alkyl;

$R^3$ is H; $C_1$ to $C_4$ alkyl; phenyl; naphthyl; benzyl; and any of phenyl, naphthyl, or benzyl in which up to two hydrogens on the ring have been replaced by substituent groups which may be the same or different and are selected from the group consisting of methyl, methoxy, methylthio, chloro, bromo, $CF_3$ or nitro, provided that when $R^2$ is $C_1$ to $C_4$ alkyl, $R^3$ must be H or $C_1$ to $C_4$ alkyl; and T is H,

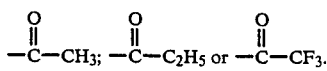

2. Composition of claim 1 wherein $R^1$ is chloro.
3. Composition of claim 1 wherein T is hydrogen.
4. Composition of claim 1 wherein X is hydrogen, and Y is selected from the group consisting of F, Cl, Br, or $CF_3$.
5. Composition of claim 1 wherein X is hydrogen and Y is chloro.
6. Composition of claim 1 wherein X and Y are both bromo.
7. The composition of claim 1 wherein X and Y are both chloro.
8. Composition of claim 1 wherein R is phenyl or substituted phenyl in which 1 or 2 hydrogens on the ring have been replaced by substituent groups which may be the same or different and are selected from the group consisting of methyl, methoxy, methylthio, chloro, bromo, $CF_3$ or nitro.
9. Composition of claim 8 wherein said substituted phenyl carries chlorine substituents at the 2 and 5 positions or only methyl at the 4-position.
10. The composition of claim 1 which contains additionally up to 2 parts by weight of crop oil or crop oil concentrated per part of total herbicidal components.
11. The composition as in claim 1 wherein the herbicidal triazine is selected from any one or more of the group consisting of ametryn, atrazine, cyanazine, cyprazine, desmetryn, dipropetryn, prometryn, propazine, simazine, symetryne, terbutryn, and metribuzin.
12. The composition as in claim 1 wherein the herbicidal triazine is selected from any one or more of the group consisting of ametryne, atrazine, cyanazine, metribuzin, propazine, simazine and symetryne.
13. The composition as in claim 1 wherein the herbicidal triazine is selected from the group consisting of atrazine and cyanazine and a co-mixture thereof.
14. The composition as in claim 1 wherein the second herbicidal composition is 4,4,4-trichloro-2-(3,5-dichlorophenyl)-2-hydroxybutyl-1-(4-methylphenyl)-sulfonate or 4,4,4-trichloro-2-(3,5-dibromophenyl)-2-hydroxybutyl-1-(4-methylphenyl)sulfonate.
15. The composition as in claim 1 which contains from about 1 to about 8 parts of herbicidal triazine per part of the second herbicidal component and up to 2 parts of crop oil or crop oil concentrate per part of total herbicidal components.
16. The composition of claim 1 which contains up to about 6 percent by weight of an agriculturally acceptable surfactant.
17. The composition of claim 9 in which the surfactant is compatible with the glycol sulfonate or sulfamate component in not promptly causing chemical conversion thereof to the corresponding epoxide.
18. The composition of claim 10 in the form of a water dispersible granular material.
19. The composition of claim 10 in the form of a wettable powder.
20. The composition of claim 10 in the form of a flowable composition in non-aqueous medium.
21. The method of controlling weeds which comprises applying to the locus of such weeds before they have reached about the 8 leaf stage a herbicidally effective amount of the composition of claim 1 in the range of about 0.625 to 3 lb/acre based upon the weight of active ingredients in the composition, utilizing sufficient composition to provide at least 0.125 lb/acre of glycol sulfonate or sulfamate compound of the formula set forth in claim 1.
22. The method of claim 21 wherein sufficient of the composition of claim 1 is utilized to provide about 0.25 to 0.5 lb/acre of glycol sulfonate or sulfamate compound.
23. The method of claim 21 wherein the said composition is applied in an effective amount in the range of about 1 to 2.5 lb/acre.

24. The method of claim 21 in which the herbicidal triazine is selected from the group consisting of any one or more of ametryne, atrazine, cyanazine, cyprazine, desmetryn, dipropetryn, prometryn, propazine, simazine, symetryne, terbutryn and metribuzin.

25. The method of claim 21 in which the herbicidal triazine employed is atrazine or cyanazine or a co-mixture thereof.

26. The method of claim 21 in which the at least one second herbicidal agent is at least one glycol (aryl)sulfonate selected from the compounds of the formula set forth in claim 1.

27. The method of claim 21 in which the second herbicidal agent is 4,4,4-trichloro-2-(3,5-dichlorophenyl)-2-hydroxybutyl-(4-methylphenyl)sulfonate.

28. The method of claim 21 in which the herbicidal triazine is admixed with crop oil or crop oil concentrate.

29. The method of claim 21 in which the composition is applied preemergently.

30. The method of claim 21 in which the composition is applied early postemergently.

31. The method of claim 30 in which the composition is applied when the weeds are between about the 2 and 6 leaf stages.

32. The method as in claim 30 in which the composition is applied wnen the weeds are in the 2 to 4 leaf stage.

33. The method of claim 21 in which both grassy and broadleafed weeds are controlled in the presence of corn or sorghum.

34. The method of claim 21 in which grassy weeds are controlled in the presence of corn or sorghum.

35. The method of controlling weeds which comprises applying concurrently to the locus of such weeds at least one herbicidal triazine and at least one second herbicidal component of the following formula:

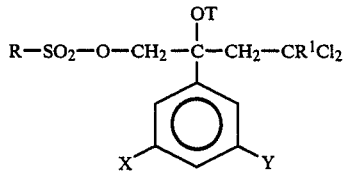

wherein:
R is $C_1$ to $C_{18}$ alkyl; $C_1$ to $C_4$ haloalkyl; $C_3$ to $C_7$ cycloalkyl; phenyl, naphthyl; benzyl; any of phenyl, naphthyl, or benzyl in which up to three hydrogens on the ring have been replaced by substituent groups which may be the same or different and are selected from the group consisting of methyl, methoxy, methylthio, chloro, bromo, $CF_3$ or nitro; or $NR^2R^3$;
$R^1$ is $CH_3$, Cl, Br, F or

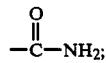

X and Y are the same or different and are Cl, Br, F, $CF_3$ or H, provided X and Y may not both be H; and
$R^2$ is H or $C_1$ to $C_4$ alkyl;
$R^3$ is H; $C_1$ to $C_4$ alkyl; phenyl; naphthyl; benzyl; and any of phenyl, naphthyl, or benzyl in which up to two hydrogens on the ring have been replaced by substituent groups which may be the same or different and are selected from the group consisting of methyl, methoxy, methylthio, chloro, bromo, $CF_3$ or nitro, provided that when $R^2$ is $C_1$ to $C_4$ alkyl, $R^3$ must be H or $C_1$ to $C_4$ alkyl; and
T is H,

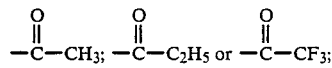

the amounts of at least one herbicidal triazine and of at least one second herbicidal component taken together being at least a herbicidally effective amount and the weight ratio of herbicidal triazine to second herbicidal component being i the range of about 1 to about 20 parts triazine per 1 go 2 parts of the second herbicidal component.

36. The method of claim 35 wherein at least the major portion of said triazine is applied separately and the second herbicidal component with up to a minor portion of said triazine is applied postemergently before said weeds have reached about the 8 leaf stage.

37. The method of claim 36 wherein the second herbicidal component and up to a minor portion of said triazine is applied postemergently before said weeds have reached about the 6 leaf stage.

38. The method of claim 35 wherein grassy weeds are controlled in the presence of corn or sorghum.

39. The method of claim 35 wherein both grassy and broadleafed weeds are controlled in the presence of corn or sorghum.

40. The composition as in claim 1 wherein the second herbicidal component is selected from the group consisting of
4,4,4-trichloro-2-(3,5-dichlorophenyl)-2-hydroxybutyl-1-methylsulfonate;
4,4,4-trichloro-2-(3,5-dichlorophenyl)-2-hydroxybutyl-1-ethylsulfonate;
4,4,4-trichloro-2-(3,5-dichlorophenyl)-2-hydroxybutyl-1-(1-methylethyl)sulfonate;
4,4,4-trichloro-2-(3,5-dichlorophenyl)-2-hydroxybutyl-1-(2-methoxycarbonylphenyl)sulfonate;
4,4,4-trichloro-2-(3,5-dichlorophenyl)-2-hydroxybutyl-1-(4-methylphenyl)sulfonate;
4,4,4-trichloro-2-(3,5-dichlorophenyl)-2-hydroxybutyl-1-phenylmethylsulfonate;
4,4,4-trichloro-2-(3,5-dichlorophenyl)-2-hydroxybutyl-1-chloromethylsulfonate;
4,4,4-trichloro-2-(3,5-dichlorophenyl)-2-hydroxybutyl-1-(1-methylethyl)sulfamate;
4,4,4-trichloro-2-(3,5-dichlorophenyl)-2-hydroxybutyl-1-(3-trifluoromethylphenyl)sulfonate;
4,4,4-trichloro-2-(3,5-dichlorophenyl)-2-hydroxybutyl-1-(4-chlorophenyl)sulfonate;
4,4,4-trichloro-2-(3,5-dichlorophenyl)-2-hydroxybutyl-1-(2,4,6-trimethylphenyl)sulfonate;
4,4,4-trichloro-2-(3,5-dichlorophenyl)-2-hydroxybutyl-1-(2,4,6-tri(1-methylethyl)phenyl)sulfonate;
4,4,4-trichloro-2-(3,5-dichlorophenyl)-2-hydroxybutyl-1-(2,5-dichlorophenyl)sulfonate;
4,4,4-trichloro-2-(3,5-dichlorophenyl)-2-hydroxybutyl-1-(4-methoxyphenyl)sulfonate;
4,4,4-trichloro-2-(3,5-dichlorophenyl)-2-hydroxybutyl-1-phenylsulfonate;
4,4,4-trichloro-2-(3,5-dichlorophenyl)-2-hydroxybutyl-1-(2,5-dimethylphenyl)sulfonate;

4,4,4-trichloro-2-(3,5-dichlorophenyl)-2-hydroxybutyl-1-(3,4-dichlorophenyl)sulfonate;
4,4,4-trichloro-2-(3,5-dichlorophenyl)-2-hydroxybutyl-1-(3,4-dimethylphenyl)sulfonate;
4,4,4-trichloro-2-(3,5-dichlorophenyl)-2-hydroxybutyl-1-n-butylsulfonate;
4,4,4-trichloro-2-(3,5-dichlorophenyl)-2-hydroxybutyl-1-(2,4-dimethylphenyl)sulfonate;
4,4,4-trichloro-2-(3,5-dichlorophenyl)-2-acetyloxybutyl-1-(1-methylethyl)sulfonate;
4,4,4-trichloro-2-(3,5-dichlorophenyl)-2-hydroxybutyl-1-(4-bromophenyl)sulfonate;
4,4,4-trichloro-2-(3,5-dichlorophenyl)-2-hydroxybutyl-1-hexadecylsulfonate;
4,4,4-trichloro-2-(3,5-dichlorophenyl)-2-hydroxybutyl-1-(4-fluorophenyl)sulfonate;
4,4,4-trichloro-2-(3,5-dichlorophenyl)-2-trifluoroacetyloxybutyl-1-(4-methylphenyl)sulfonate;
4,4,4-trichloro-2-(3,5-dichlorophenyl)-2-propionyloxybutyl-1-(4-methylphenyl)sulfonate;
4,4,4-trichloro-2-(3,5-dichlorophenyl)-2-trifluoroacetyloxybutyl-1-(2,5-dichlorophenyl)sulfonate;
4,4,4-trichloro-2-(3,5-dichlorophenyl)-2-hydroxybutyl-1-(4-(1-methylethyl)phenyl)sulfonate;
4,4,4-trichloro-2-(3,5-dichlorophenyl)-2-hydroxybutyl-1-(2-methyl-5-chlorophenyl)sulfonate;
4,4,4-trichloro-2-(3,5-dichlorophenyl)-2-hydroxybutyl-1-(4-ethylphenyl)sulfonate;
4,4,4-trichloro-2-(3,5-dichlorophenyl)-2-hydroxybutyl-1-(b-styryl)sulfonate;
4,4,4-trichloro-2-(3,5-dichlorophenyl)-2-acetyloxybutyl-1-methylsulfonate;
4,4,4-trichloro-2-(3,5-dichlorophenyl)-2-propionyloxybutyl-1-methylsulfonate
4,4,4-trichloro-2-(3,5-dichlorophenyl)-2-hydroxybutyl-1-(2-thienyl)sulfonate; and
4,4,4-trichloro-2-(3,5-dichlorophenyl-2-hydroxybutyl-1-(4-methylphenyl)sulfamate.

41. The composition as in claim 1 wherein the second herbicidal component is selected from the group consisting of
4,4,4-trichloro-2-(3,5-dichlorophenyl)-2-hydroxybutyl-1-methylsulfonate;
4,4,4-trichloro-2-(3,5-dichlorophenyl)-2-hydroxybutyl-1-ethylsulfonate;
4,4,4-trichloro-2-(3,5-dichlorophenyl)-2-hydroxybutyl-1-(1-methylethyl)sulfonate;
4,4,4-trichloro-2-(3,5-dichlorophenyl)-2-hydroxybutyl-1-(2-methoxycarbonylphenyl)sulfonate;
4,4,4-trichloro-2-(3,5-dichlorophenyl)-2-hydroxybutyl-1-(4-methylphenyl)sulfonate;
4,4,4-trichloro-2-(3,5-dichlorophenyl)-2-hydroxybutyl-1-phenylmethylsulfonate;
4,4,4-trichloro-2-(3,5-dichlorophenyl)-2-hydroxybutyl-1-chloromethylsulfonate;
4,4,4-trichloro-2-(3,5-dichlorophenyl)-2-hydroxybutyl-1-(1-methylethyl)sulfamate;
4,4,4-trichloro-2-(3,5-dichlorophenyl)-2-hydroxybutyl-1-(3-trifluoromethylphenyl)sulfonate;
4,4,4-trifluoro-2-(3,5-dichlorophenyl)-2-hydroxybutyl-1-(4-chlorophenyl)sulfonate;
4,4,4-trichloro-2-(3,5-dichlorophenyl)-2-hydroxybutyl-1-(2,4,6-trimethylphenyl)sulfonate;
4,4,4-trichloro-2-(3,5-dichlorophenyl)-2-hydroxybutyl-1-(2,4,6-tri(1-methylethyl)phenyl)sulfonate;
4,4,4-trichloro-2-(3,5-dichlorophenyl)-2-hydroxybutyl-1-(2,5-dichlorophenyl)sulfonate;
4,4,4-trichloro-2-(3,5-dichlorophenyl)-2-hydroxybutyl-1-(4-methoxyphenyl)sulfonate;

42. The composition as in claim 40 wherein the first herbicidal component is atrazine.
43. The composition as in claim 41 wherein the first herbicidal component is atrazine.
44. The method of claim 21 in which the second herbicidal agent is selected from the group consisting of
4,4,4-trichloro-2-(3,5-dichlorophenyl)-2-hydroxybutyl-1-methylsulfonate;
4,4,4-trichloro-2-(3,5-dichlorophenyl)-2-hydroxybutyl-1-ethylsulfonate;
4,4,4-trichloro-2-(3,5-dichlorophenyl)-2-hydroxybutyl-1-(1-methylethyl)sulfonate;
4,4,4-trichloro-2-(3,5-dichlorophenyl)-2-hyroxybutyl-1-(2-methoxycarbonylphenyl)sulfonate;
4,4,4-trichloro-2-(3,5-dichlorophenyl)-2-hydroxybutyl-1-(4-methylphenyl)sulfonate;
4,4,4-trichloro-2-(3,5-dichlorophenyl)-2-hydroxybutyl-1-phenylmethylsulfonate;
4,4,4-trichloro-2-(3,5-dichlorophenyl)-2-hydroxybutyl-1-chloromethylsulfonate;
4,4,4-trichloro-2-(3,5-dichlorophenyl)-2-hydroxybutyl-1-(1-methylethyl)sulfamate;
4,4,4-trichloro-2-(3,5-dichlorophenyl)-2-hydroxybutyl-1-(3-trifluoromethylphenyl)sulfonate;
4,4,4-trichloro-2-(3,5-dichlorophenyl)-2-hydroxybutyl-1-(4-chlorophenyl)sulfonate;
4,4,4-trichloro-2-(3,5-dichlorophenyl)-2-hydroxybutyl-1-(2,4,6-trimethylphenyl)sulfonate;
4,4,4-trichloro-2-(3,5-dichlorophenyl)-2-hydroxybutyl-1-(2,4,6-tri(1-methylethyl)phenyl)sulfonate;
4,4,4-trichloro-2-(3,5-dichlorophenyl)-2-hydroxybutyl-1-(2,5-dichlorophenyl)sulfonate;
4,4,4-trichloro-2-(3,5-dichlorophenyl)-2-hydroxybutyl-1-(4-methoxyphenyl)sulfonate;
4,4,4-trichloro-2-(3,5-dichlorophenyl)-2-hydroxybutyl-1-phenylsulfonate;
4,4,4-trichloro-2-(3,5-dichlorophenyl)-2-hydroxybutyl-1-(2,5-dimethylphenyl)sulfonate;
4,4,4-trichloro-2-(3,5-dichlorophenyl)-2-hydroxybutyl-1-(3,4-dichlorophenyl)sulfonate;
4,4,4-trichloro-2-(3,5-dichlorophenyl)-2-hydroxybutyl-1-(3,4-dimethylphenyl)sulfonate;
4,4,4-trichloro-2-(3,5-dichlorophenyl)-2-hydroxybutyl-1-n-butylsulfonate;
4,4,4-trichloro-2-(3,5-dichlorophenyl)-2-hydroxybutyl-1-(2,4-dimethylphenyl)sulfonate;
4,4,4-trichloro-2-(3,5-dichlorophenyl)-2-acetyloxybutyl-1-(1-methylethyl)sulfonate;
4,4,4-trichloro-2-(3,5-dichlorophenyl)-2-hydroxybutyl-1-(4-bromophenyl)sulfonate;
4,4,4-trichloro-2-(3,5-dichlorophenyl)-2-hydroxybutyl-1-hexadecylsulfonate;
4,4,4-trichloro-2-(3,5-dichlorophenyl)-2-hydroxybutyl-1-(4-fluorophenyl)sulfonate;
4,4,4-trichloro-2-(3,5-dichlorophenyl)-2-trifluoroacetyloxybutyl-1-(4-methylphenyl)sulfonate;
4,4,4-trifluoro-2-(3,5-dichlorophenyl)-2-propionyloxybutyl-1-(4-methylphenyl)sulfonate;
4,4,4-trichloro-2-(3,5-dichlorophenyl)-2-trifluoroacetyloxybutyl-1-(2,5-dichlorophenyl)sulfonate;
4,4,4-trichloro-2-(3,5-dichlorophenyl)-2-hydroxybutyl-1-(4-(1-methylethyl)phenyl)sulfonate;
4,4,4-trichloro-2-(3,5-dichlorophenyl)-2-hydroxybutyl-1-(2-methyl-5-chlorophenyl)sulfonate;

4,4,4-trichloro-2-(3,5-dichlorophenyl)-2-hydroxybutyl-1-(4-ethylphenyl)sulfonate;
4,4,4-trichloro-2-(3,5-dichlorophenyl)-2-hydroxybutyl-1-(b-styryl)sulfonate;
4,4,4-trichloro-2-(3,5-dichlorophenyl)-2-acetyloxybutyl-1-methylsulfonate;
4,4,4-trichloro-2-(3,5-dichlorophenyl)-2-propionyloxybutyl-1-methylsulfonate
4,4,4-trichloro-2-(3,5-dichlorophenyl)-2-hydroxybutyl-1-(2-thienyl)sulfonate; and
4,4,4-trichloro-2-(b 3,5-dichlorophenyl-2-hydroxybutyl-1-(4-methylphenyl)sulfamate.

45. The method of claim 21 in which the second herbicidal agent is selected from the group consisting of
4,4,4-trichloro-2-(3,5-dichlorophenyl)-2-hydroxybutyl-1-methylsulfonate;
4,4,4-trichloro-2-(3,5-dichlorophenyl)-2-hydroxybutyl-1-ethylsulfonate;
4,4,4-trichloro-2-(3,5-dichlorophenyl)-2-hydroxybutyl-1-(1-methylethyl)sulfonate;
4,4,4-trichloro-2-(3,5-dichlorophenyl)-2-hydroxybutyl-1-(2-methoxycarbonylphenyl)sulfonate;
4,4,4-trichloro-2-(3,5-dichlorophenyl)-2-hydroxybutyl-1-(4-methylphenyl)sulfonate;
4,4,4-trichloro-2-(3,5-dichlorophenyl)-2-hydroxybutyl-1-phenylmethylsulfonate;
4,4,4-trichloro-2-(3,5-dichlorophenyl)-2-hydroxybutyl-1-chloromethylsulfonate;
4,4,4-trichloro-2-(3,5-dichlorophenyl)-2-hydroxybutyl-1-(1-methylethyl)sulfamate;
4,4,4-trichloro-2-(3,5-dichlorophenyl)-2-hydroxybutyl-1-(3-trifluoromethylphenyl)sulfonate;
4,4,4-trichloro-2-(3,5-dichlorophenyl)-2-hydroxybutyl-1-(4-chlorophenyl)sulfonate;
4,4,4-trichloro-2-(3,5-dichlorophenyl)-2-hydroxybutyl-1-(2,4,6-trimethylphenyl)sulfonate;
4,4,4-trichloro-2-(3,5-dichlorophenyl)-2-hydroxybutyl-1-(2,4,6-tri(1-methylethyl)phenyl)sulfonate;
4,4,4-trichloro-2-(3,5-dichlorophenyl)-2-hydroxybutyl-1-(2,5-dichlorophenyl)sulfonate;
4,4,4-trichloro-2-(3,5-dichlorophenyl)-2-hydroxybutyl-1-(4-methoxyphenyl)sulfonate;

46. The method of claim 44 in which the first herbicidal agent is atrazine.
47. The method of claim 45 in which the first herbicidal agent is atrazine.

* * * * *